United States Patent
Zhuo et al.

(10) Patent No.: US 11,939,340 B2
(45) Date of Patent: Mar. 26, 2024

(54) CDK INHIBITORS AND THEIR USE AS PHARMACEUTICALS

(71) Applicant: Prelude Therapeutics Incorporated, Wilmington, DE (US)

(72) Inventors: Jincong Zhuo, Garnet Valley, PA (US); Xiaowei Wu, Wilmington, DE (US); Katarina Rohlfing, Conshohocken, PA (US); Andrew Combs, Kennett Square, PA (US)

(73) Assignee: Prelude Therapeutics Incorporated, Wilmington, DE (US)

(*) Notice: Subject to any disclaimer, the term of this patent is extended or adjusted under 35 U.S.C. 154(b) by 0 days.

(21) Appl. No.: 18/157,229

(22) Filed: Jan. 20, 2023

(65) Prior Publication Data
US 2023/0234964 A1    Jul. 27, 2023

Related U.S. Application Data

(60) Provisional application No. 63/301,682, filed on Jan. 21, 2022.

(51) Int. Cl.
| | | |
|---|---|---|
| *C07D 495/14* | (2006.01) | |
| *A61K 45/06* | (2006.01) | |
| *A61P 15/08* | (2006.01) | |
| *A61P 35/00* | (2006.01) | |
| *C07D 498/14* | (2006.01) | |

(52) U.S. Cl.
CPC ........... *C07D 495/14* (2013.01); *A61K 45/06* (2013.01); *A61P 15/08* (2018.01); *A61P 35/00* (2018.01); *C07D 498/14* (2013.01); *C07B 2200/05* (2013.01)

(58) Field of Classification Search
CPC ..... C07D 239/00; C07D 495/14; A61P 35/00; A61K 31/506
See application file for complete search history.

(56) References Cited

U.S. PATENT DOCUMENTS

| | | |
|---|---|---|
| 3,657,744 A | 4/1972 | Ersek |
| 4,739,762 A | 4/1988 | Palmaz |
| 4,992,445 A | 2/1991 | Lawter et al. |
| 5,001,139 A | 3/1991 | Lawter et al. |
| 5,023,252 A | 6/1991 | Hseih |
| 5,040,548 A | 8/1991 | Yock |
| 5,061,273 A | 10/1991 | Yock |
| 5,195,984 A | 3/1993 | Schatz |
| 5,292,331 A | 3/1994 | Boneau |
| 5,451,233 A | 9/1995 | Yock |
| 5,496,346 A | 3/1996 | Horzewski et al. |
| 5,674,278 A | 10/1997 | Boneau |
| 5,879,382 A | 3/1999 | Boneau |
| 6,344,053 B1 | 2/2002 | Boneau |
| 2019/0048014 A1 | 2/2019 | Lin et al. |
| 2019/0284193 A1 | 9/2019 | Luengo et al. |
| 2020/0115378 A1* | 4/2020 | Sokolsky ............. C07D 471/04 |
| 2020/0148692 A1 | 5/2020 | Lin et al. |

FOREIGN PATENT DOCUMENTS

| | | | | |
|---|---|---|---|---|
| WO | WO-2006044869 A1 * | 4/2006 | ........... | C07D 498/04 |
| WO | 2020180959 A1 | 9/2020 | | |
| WO | WO-2020180959 A1 * | 9/2020 | ........... | A61K 31/506 |

* cited by examiner

*Primary Examiner* — Theodore R. Howell
*Assistant Examiner* — George W Kosturko
(74) *Attorney, Agent, or Firm* — BakerHostetler

(57) ABSTRACT

The disclosure is directed to compounds of Formula I

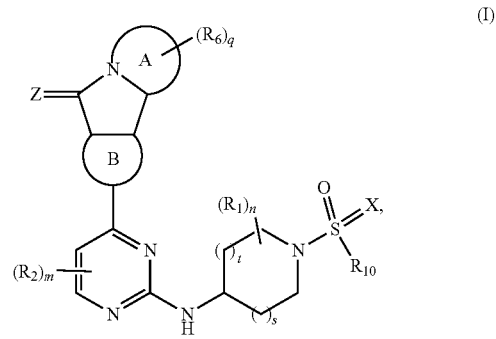

pharmaceutical compositions comprising compounds of Formula I, as well as methods of their use and preparation, are also described.

24 Claims, No Drawings

CDK INHIBITORS AND THEIR USE AS PHARMACEUTICALS

CROSS REFERENCE TO RELATED APPLICATIONS

This application claims the benefit of U.S. Provisional Application No. 63/301,682, filed Jan. 21, 2022, the entirety of which is incorporated by reference herein.

TECHNICAL FIELD

The disclosure is directed to CDK inhibitors and methods of their use.

BACKGROUND

Cyclin-dependent kinases (CDKs) are a family of conserved serine/threonine kinases that play critical roles in cell cycle and gene transcription regulation (Malumbres 2014). Among the cell cycle CDK subfamily, CDK4 and CDK6 are the master regulators that control entry of cells from the first gap phase (G1) to the DNA synthesis phase (S). During this process, cyclin D protein levels increase, complex with CDK4/6 and activate their kinase activities. Activated CDK4/6 complexes phosphorylate retinoblastoma protein (RB1) and other RB1-like proteins, reduce their binding affinities and release RB1-containing transcription repressor complexes from E2F transcription factors, resulting in activation of E2F controlled cell cycle genes and progression of cell cycle (Lapenna and Giordano 2009, Asghar, Witkiewicz et al. 2015).

Small molecule CDK2/4/6 inhibitors are needed.

SUMMARY OF THE INVENTION

The disclosure is directed to compounds of Formula I:

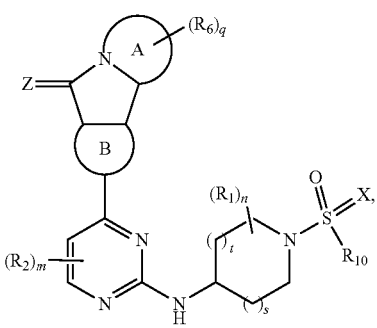

(I)

or a pharmaceutically acceptable salt thereof, wherein
or a pharmaceutically acceptable salt or solvate or N-oxide thereof, wherein
  ring A is a 4-9-membered cycloalkyl or heterocycloalkyl ring;
  ring B is a 5-membered heteroaryl selected from:

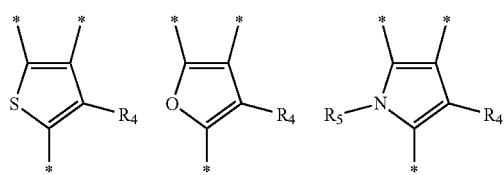

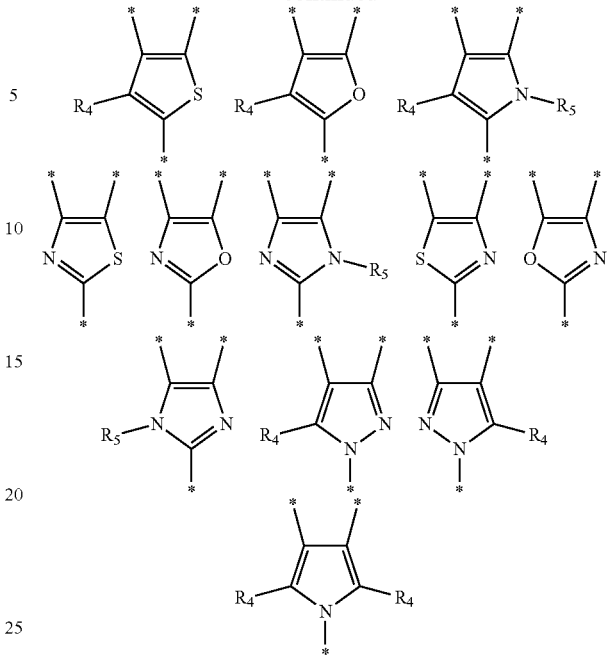

Z is O, S, $NR^b$, $NOR^b$ or N—CN,
m is 0, 1 or 2;
n is 0, 1, 2, 3, 4, 5, 6, 7, 8 or 9;
s is 0, 1, 2 or 3;
t is 0, 1, 2 or 3;
q is 0, 1, 2, 3, 4, 5, 6, 7, 8 or 9;
each $R_1$, when present, is independently H, D, halogen, —OH, —CN, —NO$_2$, oxo, —C$_1$-C$_6$alkyl, C$_{1-6}$alkoxide, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$;
or two $R^1$ together with the carbone atom(s) to which they are both attached at same carbon or different carbones, form a carbocyclic or heterocyclic group;
each $R_2$ is independently H, D, halogen, C$_1$-C$_8$ alkoxide, C$_1$-C$_8$ alkyl, haloalkoxide, SF$_5$, or CN, wherein the C$_{1-8}$alkyl may be optionally substituted with D, halogen, —OH, —CN, or cycloalkyl;
each $R_4$ is independently H, D, halogen, CN, —C$_2$-C$_6$alkenyl, —C$_2$-C$_6$alkynyl, C$_1$-C$_8$ alkoxide, C$_1$-C$_8$ alkyl, haloalkyl, C$_1$-C$_8$ hydroxylalkyl, C$_3$-C$_8$ cycloalkyl or C$_3$-C$_8$ heteroycloalkyl;
each $R^a$ is independently H, D, —C(O)R$^b$, —C(O)OR$^c$, —C(O)NR$^c$R$^d$, —C(=NR$^b$)NR$^b$R$^c$, —C(=NOR$^b$)NR$^b$R$^c$, —C(=NCN)NR$^b$R$^c$, —P(OR$^c$)$_2$, —P(O)OR$^c$OR$^b$, —S(O)$_2$R$^b$, —S(O)$_2$NR$^c$R$^d$, SiR$^b$$_3$, —C$_1$-C$_{10}$alkyl, —C$_2$-C$_{10}$ alkenyl, —C$_2$-C$_{10}$ alkynyl, C$_0$-C$_1$alk-aryl, cycloalkyl, cycloalkenyl, C$_0$-C$_1$alk-heteroaryl, heterocycloalkyl, or heterocycloalkenyl;
each $R^b$, is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl;
each $R^c$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

each $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

$R_5$ is H, D, $OR^b$, $C_{1-4}$alkyl, wherein the $C_{1-4}$alkyl may be optionally substituted with at least one of D, halogen, —OH, —CN or an amine, cycloalkyl, heterocycloalkyl; and each $R_6$, when present, is independently H, D, halogen, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$; wherein said that —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl is optionally substituted by 1-6 R groups selected from H, D, halogen, —OH, —CN, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$;

or two $R_6$ groups together with the atom(s) to which they attached (same atom or different atoms) can form a spirocyclic group, multicyclic heterocycloalkyl, or a multicyclic cycloalkyl group;

X is O or $NR^5$;

$R_{10}$ is H, D, —$NR^cR^d$, —$NR^aR^c$, $C_{1-6}$alkyl, $C_{3-7}$cycloalkyl, $C_{4-7}$heterocycloalkyl, $C_{3-7}$ cycloalkylalkyl, $C_{4-7}$heterocycloalkylalkyl, aryl, heteroaryl, arylalkyl, heteroarylalkyl, or haloalkyl; wherein said that $C_{1-6}$alkyl, $C_{3-7}$cycloalkyl, $C_{4-7}$heterocycloalkyl, $C_{3-7}$cycloalkylalkyl, $C_{4-7}$ heterocycloalkylalkyl, aryl, heteroaryl, arylalkyl and heteroarylalkyl is optionally substituted by 1-6 R selected from H, D, halogen, —OH, —CN, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$.

Stereoisomers of the compounds of Formula I, as well as the pharmaceutical salts, solvates, and N-oxides thereof, are also contemplated, described, and encompassed herein. Methods of using compounds of Formula I are described, as well as pharmaceutical compositions including the compounds of Formula I.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

At various places in the present specification, substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. "$C_0$ alkyl" refers to a covalent bond.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like. Alkyl groups of the disclosure can be unsubstituted or substituted. In those embodiments wherein the alkyl group is substituted, the alkyl group can be substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —$C(O)NH(C_1$-$C_6$alkyl), —$C(O)N(C_1$-$C_6$alkyl$)_2$, —$OC(O)NH(C_1$-$C_6$alkyl), —$OC(O)N(C_1$-$C_6$alkyl$)_2$, —$S(O)_2NH(C_1$-$C_6$alkyl), and —$S(O)_2N(C_1$-$C_6$alkyl$)_2$.

The term "alkoxide" refers to the conjugate base of an alcohol and includes an organic group bonded to a negatively charged oxygen atom.

The term "halo" or halogen, refers to chloro, fluoro, bromo, or iodo.

The term "haloalkyl" refers to any alkyl radical having one or more hydrogen atoms replaced by a halogen atom.

The term "cycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"). Cycloalkyl groups of the disclosure include monocyclic groups, as well as multicyclic groups such as bicyclic and tricyclic groups. In those embodiments having at least one multicyclic cycloalkyl group, the cyclic groups can share one common atom (i.e., spirocyclic). In other embodiments having at least one multicyclic cycloalkyl group, the cyclic groups share two common atoms. Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), spiro[3.3]heptanyl, bicyclo[3.3.0]octanyl, and the like. Cycloalkyl groups of the disclosure can be unsubstituted or substituted. In those embodiments wherein the cycloalkyl group is substituted, the cycloalkyl group can be substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "cycloalkenyl" refer to cyclic, non-aromatic hydrocarbon groups having from 3 to 10 carbon atoms ("$C_3$-$C_{10}$"), preferably from 3 to 6 carbon atoms ("$C_3$-$C_6$") and containing at least one carbon-carbon double bond. For example, cycloalkenyl groups include, but are not limited to cyclopropenyl, cyclobutenyl, and the like.

The term "heterocycloalkyl" when used alone or as part of a substituent group refers to any three to ten membered monocyclic or bicyclic, saturated ring structure containing at least one heteroatom selected from the group consisting of O, N and S. Heterocycloalkyl groups of the disclosure include monocyclic groups, as well as multicyclic groups such as bicyclic and tricyclic groups. In those embodiments having at least one multicyclic heterocycloalkyl group, the cyclic groups can share one common atom (i.e., spirocyclic). In other embodiments having at least one multicyclic heterocycloalkyl group, the cyclic groups share two common atoms. The term —$C_3$-$C_6$ heterocycloalkyl refers to a heterocycloalkyl group having between three and six carbon ring atoms. The term —$C_3$-$C_{10}$ heterocycloalkyl refers to a heterocycloalkyl group having between three and 10 ring atoms. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, azepanyl, diazepanyl, oxepanyl, dioxepanyl, azocanyl diazocanyl, oxocanyl, dioxocanyl, azaspiro[2.2]pentanyl, oxaazaspiro[3.3]heptanyl, oxaspiro[3.3]heptanyl, dioxaspiro[3.3]heptanyl, and the like. Heteroycloalkyl groups of the disclosure can be unsubstituted or substituted. In those embodiments wherein the heterocycloalkyl group is substituted, the heterocycloalkyl group can be substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heterocycloalkenyl" when used alone or as part of a substituent group refers to any three to ten membered monocyclic or bicyclic, partially saturated ring structure containing at least one heteroatom selected from the group consisting of O, N and S. Heterocycloalkenyl groups of the disclosure include monocyclic groups, as well as multicyclic groups such as bicyclic and tricyclic groups. In those embodiments having at least one multicyclic heterocycloalkyenyl group, the cyclic groups can share one common atom (i.e., spirocyclic). In other embodiments having at least one multicyclic heterocycloalkenyl group, the cyclic groups share two common atoms. The term —$C_3$-$C_6$ heterocycloalkenyl refers to a heterocycloalkenyl group having between three and six carbon atoms. The term —$C_3$-$C_{10}$ heterocycloalkenyl refers to a heterocycloalkenyl group having between three and ten ring atoms. The heterocycloalkenyl group may be attached at any heteroatom or carbon atom of the ring such that the result is a stable structure. Heteroycloalkenyl groups of the disclosure can be unsubstituted or substituted. In those embodiments wherein the heterocycloalkenyl group is substituted, the heterocycloalkenyl group can be substituted with 1, 2, or 3 substituents independently selected from D, —OH, —CN, amino, halo, oxo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heteroaryl" when used alone or as part of a substituent group refers to a mono- or bicyclic-aromatic ring structure including carbon atoms as well as up to five heteroatoms selected from nitrogen, oxygen, and sulfur. Heteroaryl rings can include a total of 5, 6, 7, 8, 9, or 10 ring atoms. The term —$C_5$-$C_{10}$ heteroaryl refers to a heteroaryl group containing five to ten ring atoms. Examples of heteroaryl groups include but are not limited to, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like. Heteroaryl groups of the disclosure can be unsubstituted or substituted. In those embodiments wherein the heteroaryl group is substituted, the heteroaryl group can be substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "aryl" when used alone or as part of a substituent group refers to a mono- or bicyclic-aromatic carbon ring structure. Aryl rings can include a total of 6, 7, 8, 9, or 10 ring atoms. Examples of aryl groups include but are not limited to, phenyl, napthyl, and the like. Aryl groups of the disclosure can be unsubstituted or substituted. In those embodiments wherein the aryl group is substituted, the aryl group can be substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "alkenyl" refers to $C_2$-$C_{12}$ alkyl group that contains at least one carbon-carbon double bond. In some embodiments, the alkenyl group is optionally substituted. In some embodiments, the alkenyl group is a $C_2$-$C_6$ alkenyl.

The term "alkynyl" refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

As used herein, "alkoxy" refers to an —O-alkyl group. Example alkoxy groups include methoxy, ethoxy, propoxy (e.g., n-propoxy and isopropoxy), t-butoxy, and the like.

As used herein, "hydroxylalkyl" refers to an alkyl group substituted by OH.

When a range of carbon atoms is used herein, for example, $C_1$-$C_6$, all ranges, as well as individual numbers of carbon atoms are encompassed, for example, "$C_{1-3}$" includes $C_{1-3}$, $C_{1-2}$, $C_{2-3}$, $C_1$, $C_2$, and $C_3$. The term "$C_{1-6}$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—$C_0$alk-" refers to a bond.

The term "$C_0$-$C_6$alk" when used alone or as part of a substituent group refers to an aliphatic linker having 0, 1, 2, 3, 4, 5 or 6 carbon atoms. The term "—$C_1$alk-", for example, refers to a —$CH_2$—. The term "—$C_0$alk-" refers to a bond.

Moieties of the disclosure, for example, —$C_1$-$C_6$alkyl, —$C_1$-$C_{10}$ alkyl, —$C_2$-$C_6$alkenyl, —$C_2$-$C_{10}$alkenyl, —$C_2$-$C_6$alkynyl, —$C_2$-$C_{10}$alkynyl, aryl, heteroaryl, cycloalkyl, cycloalkenyl, heterocycloalkenyl, and heterocycloalky,l can be optionally substituted with 1, 2, or 3 substituents independently selected from D, —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Geometric isomers of olefins, C═N double bonds, and the like can also be present in the compounds described herein, and all such stable isomers are contemplated in the present invention. Geometric isomers of the compounds of the present invention are described and may be isolated as a mixture of isomers or as separated isomeric forms.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

Compounds of the invention may also include tautomeric forms. All tautomeric forms are encompassed.

In some embodiments, the compounds of the present invention may exist as rotational isomers. In some embodiments, the compounds of the present invention exist as mixtures of rotational isomers in any proportion. In other embodiments, the compounds of the present invention exist as particular rotational isomers, substantially free of other rotational isomers.

In some embodiments, the compounds of the invention, and salts thereof, are substantially isolated. By "substantially isolated" is meant that the compound is at least partially or substantially separated from the environment in which was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes mammals, and in particular, humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I as described herein, as well as its subgenera, which expression includes the stereoisomers (e.g., enantiomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

Compounds of the invention can also include all isotopes of atoms occurring in the intermediates or final compounds. Isotopes include those atoms having the same atomic number but different mass numbers. For example, isotopes of hydrogen include tritium and deuterium.

The disclosure is directed to compounds of Formula I:

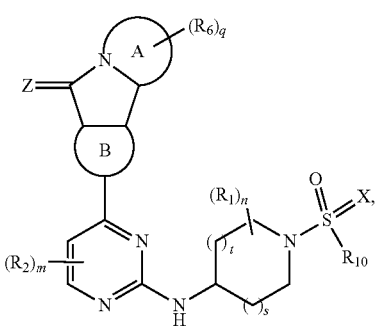

(I)

or a pharmaceutically acceptable salt or solvate or N-oxide thereof, wherein
ring A is a 4-9-membered cycloalkyl or heterocycloalkyl ring;
ring B is a 5-membered heteroaryl selected from:

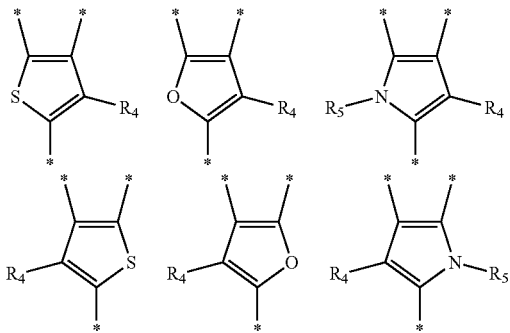

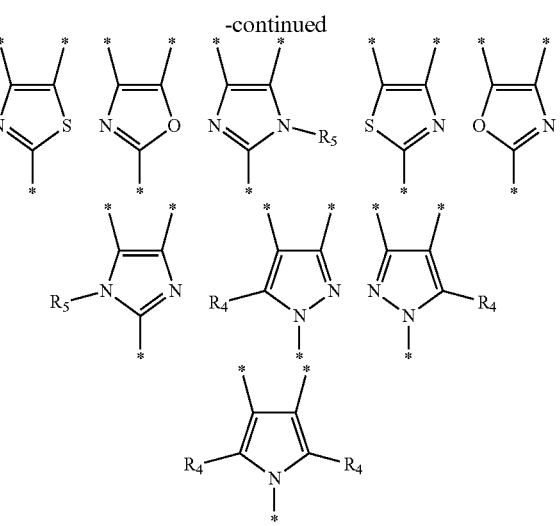

Z is O, S, $NR^b$, $NOR^b$ or N—CN,
m is 0, 1 or 2;
n is 0, 1, 2, 3, 4, 5, 6, 7, 8 or 9;
s is 0, 1, 2 or 3;
t is 0, 1, 2 or 3;
q is 0, 1, 2, 3, 4, 5, 6, 7, 8 or 9;
each $R_1$, when present, is independently H, D, halogen, —OH, —CN, —$NO_2$, oxo, —$C_1$-$C_6$alkyl, $C_{1-6}$alkoxide, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$;

or two $R^1$ together with the carbone atom(s) to which they are both attached at same carbon or different carbones, form a carbocyclic or heterocyclic group;

each $R_2$ is independently H, D, halogen, $C_1$-$C_8$ alkoxide, $C_1$-$C_8$ alkyl, haloalkoxide, $SF_5$, or CN, wherein the $C_{1-8}$alkyl may be optionally substituted with D, halogen, —OH, —CN, or cycloalkyl;

each $R_4$ is independently H, D, halogen, CN, —$C_2$-$C_6$alkenyl, —$C_2$-$C_6$alkynyl, $C_1$-$C_8$ alkoxide, $C_1$-$C_8$ alkyl, haloalkyl, $C_1$-$C_8$ hydroxylalkyl, $C_3$-$C_8$ cycloalkyl or $C_3$-$C_8$ heteroycloalkyl;

each $R^a$ is independently H, D, —$C(O)R^b$, —$C(O)OR^c$, —$C(O)NR^cR^d$, —$C(=NR^b)NR^bR^c$, —$C(=NOR^b)NR^bR^c$, —$C(=NCN)NR^bR^c$, —$P(OR^c)_2$, —$P(O)OR^cOR^b$, —$S(O)_2R^b$, —$S(O)_2NR^cR^d$, $SiR^b_3$, —$C_1$-$C_{10}$alkyl, —$C_2$-$C_{10}$ alkenyl, —$C_2$-$C_{10}$ alkynyl, $C_0$-$C_1$alk-aryl, cycloalkyl, cycloalkenyl, $C_0$-$C_1$alk-heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, $C_0$-$C_1$alk-aryl, cycloalkyl, cycloalkenyl, $C_0$-$C_1$alk-heteroaryl, heterocycloalkyl, or heterocycloalkenyl;

each $R^c$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

each $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

$R_5$ is H, D, $OR^b$, $C_{1-4}$alkyl, wherein the $C_{1-4}$alkyl may be optionally substituted with at least one of D, halogen, —OH, —CN or an amine, cycloalkyl, heterocycloalkyl; and each $R_6$, when present, is independently H, D, halogen, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^c R^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$; wherein said that —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl is optionally substituted by 1-6 R groups selected from H, D, halogen, —OH, —CN, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$;

or two $R_6$ groups together with the atom(s) to which they attached (same atom or different atoms) can form a spirocyclic group, multicyclic heterocycloalkyl, or a multicyclic cycloalkyl group;

X is O or $NR^5$; and $R_{10}$ is H, D, —$NR^cR^d$, —$NR^aR^c$, $C_{1-6}$alkyl, $C_{3-7}$cycloalkyl, $C_{4-7}$heterocycloalkyl, $C_{3-7}$ cycloalkylalkyl, $C_{4-7}$heterocycloalkylalkyl, aryl, heteroaryl, arylalkyl, heteroarylalkyl, or haloalkyl; wherein said that $C_{1-6}$alkyl, $C_{3-7}$cycloalkyl, $C_{4-7}$heterocycloalkyl, $C_{3-7}$cycloalkylalkyl, $C_{4-7}$ heterocycloalkylalkyl, aryl, heteroaryl, arylalkyl and heteroarylalkyl is optionally substituted by 1-6 R selected from H, D, halogen, —OH, —CN, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$.

In some embodiments, ring A in Formula (I) is a 4-9-membered cycloalkyl or heterocycloalkyl ring;

In some embodiments, ring A in Formula (I) is a 4-9-membered cycloalkyl ring. In some embodiments, ring A is a 4-membered cycloalkyl ring. In other embodiments, ring A is a 5-membered cycloalkyl ring. In yet other embodiments, ring A is a 6-membered cycloalkyl ring. In yet other embodiments, ring A is a 7-membered cycloalkyl ring. In yet other embodiments, ring A is an 8-membered cycloalkyl ring. In yet other embodiments, ring A is a 9-membered cycloalkyl ring.

In some embodiments, ring A in Formula (I) is a cyclobutane. In other embodiments, ring A in Formula (I) is a cyclopentane. In yet other embodiments, ring A in Formula (I) is a cyclohexane. In yet other embodiments, ring A in Formula (I) is a cycloheptane. In yet other embodiments, ring A in Formula (I) is a cyclooctane. In yet other embodiments, ring A in Formula (I) is a cyclononane.

In some embodiments, ring A in Formula (I) is a 4-9-membered heterocycloalkyl ring. In other embodiments, ring A is a 4-membered heterocycloalkyl ring. In other embodiments, ring A is a 5-membered heterocycloalkyl ring. In yet other embodiments, ring A is a 6-membered heterocycloalkyl ring. In yet other embodiments, ring A is a 7-membered heterocycloalkyl ring. In yet other embodiments, ring A is an 8-membered heterocycloalkyl ring. In yet other embodiments, ring A is a 9-membered heterocycloalkyl ring.

In some embodiments, ring A in Formula (I) is an oxetane or an azetidine. In other embodiments, ring A in Formula (I) is a tetrahydrofuran or a pyrrolidine. In yet other embodiments, ring A in Formula (I) is a tetrahydro-2H-pyran or a piperidine. In yet other embodiments, ring A in Formula (I) is an oxepane or an azepane. In yet other embodiments, ring A in Formula (I) is an oxocane or an azocane.

In some embodiments, ring B is a 5-membered heteroaryl selected from:

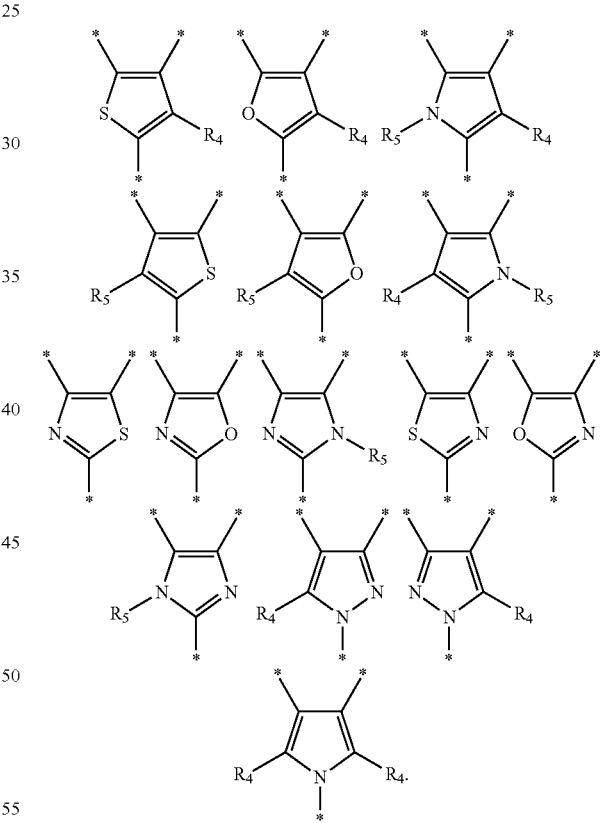

In some embodiments, ring B is

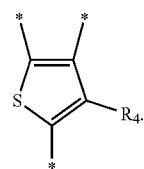

In other embodiments, ring B is

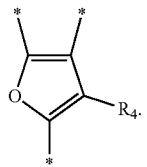

In yet other embodiments, ring B is

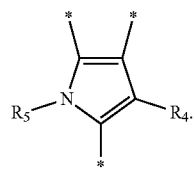

In yet other embodiments, ring B is

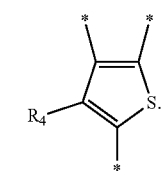

In yet other embodiments, ring B is

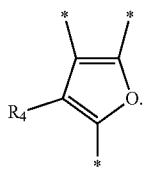

In yet other embodiments, ring B is

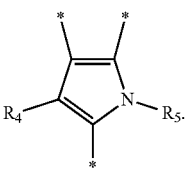

In yet other embodiments, ring B is

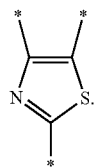

In yet other embodiments, ring B is

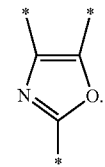

In yet other embodiments, ring B is

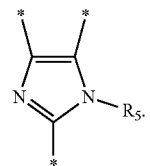

In yet other embodiments, ring B is

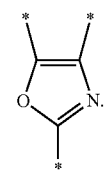

In yet other embodiments, ring B is

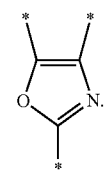

In yet other embodiments, ring B is

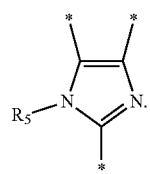

In yet other embodiments, ring B is

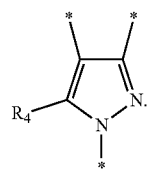

In yet other embodiments, ring B is

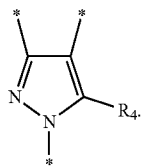

In yet other embodiments, ring B is

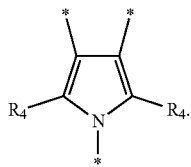

In some embodiments, each $R_4$, when present, in Formula I is independently H, D, halogen, —CN, —$C_2$-$C_6$alkenyl, —$C_2$-$C_6$alkynyl, $C_1$-$C_8$ alkoxide, $C_1$-$C_8$ alkyl, haloalkyl, $C_1$-$C_8$ hydroxylalkyl, $C_3$-$C_8$ cycloalkyl or $C_3$-$C_8$ heterocycloalkyl.

In some embodiments, $R_4$ in Formula I is independently H. In some embodiments, $R_4$ in Formula I is independently D. In some embodiments, $R_4$ in Formula I is independently halogen. In other embodiments, $R_4$ in Formula I is independently —CN. In other embodiments, $R_4$ in Formula I is independently —$C_2$-$C_6$ alkenyl. In other embodiments, $R_4$ in Formula I is independently $C_1$-$C_8$ alkoxide. In other embodiments, $R_4$ in Formula I is independently $C_1$-$C_8$ alkyl. In yet other embodiments, $R_4$ in Formula I is independently haloalkyl. In yet other embodiments, $R_4$ in Formula I is independently $C_1$-$C_8$ hydroxylalkyl. In yet other embodiments, $R_4$ in Formula I is independently $C_3$-$C_8$ cycloalkyl. In yet other embodiments, $R_4$ in Formula I is independently $C_3$-$C_8$ heteroycloalkyl.

In yet other embodiments, $R_4$ in Formula I is independently methyl. In yet other embodiments, $R_4$ is independently haloalkyl. In yet other embodiments, $R_4$ in Formula I is independently $C_1$-$C_8$ hydroxylalkyl. In some embodiments, Z in Formula (I) is O, S, $NR^b$, $NOR^b$ or N—CN. In some embodiments, Z is O. In some embodiments, Z is S. In some embodiments, Z is $NR^b$. In some embodiments, Z is $NOR^b$. In some embodiments, Z is N—CN.

In some embodiments, m in Formula (I) is 0, 1 or 2. In some embodiments, m is 0. In some embodiments, m is 1. In other embodiments, m is 2.

In some embodiments, n in Formula (I) is 0, 1, 2, 3, 4, 5, 6, 7, 8 or 9. In some embodiments, n is 0. In some embodiments, n is 1. In some embodiments, n is 2. In other embodiments, n is 3. In other embodiments, n is 4. In other embodiments, n is 5. In other embodiments, n is 6. In other embodiments, n is 7. In other embodiments, n is 8. In other embodiments, n is 9.

In some embodiments, s in Formula (I) is 0, 1, 2 or 3. In some embodiments, s is 0. In some embodiments, s is 1. In other embodiments, s is 2. In yet other embodiments, s is 3.

In some embodiments, t in Formula (I) is 0, 1, 2 or 3. In some embodiments, t is 0. In some embodiments, t is 1. In other embodiments, t is 2. In yet other embodiments, t is 3.

In some embodiments, q in Formula (I) is 0, 1, 2, 3, 4, 5, 6, 7, 8 or 9. In some embodiments, q is 0. In some embodiments, q is 1. In some embodiments, q is 2. In other embodiments, q is 3. In other embodiments, q is 4. In other embodiments, q is 5. In other embodiments, q is 6. In other embodiments, q is 7. In other embodiments, q is 8. In other embodiments, q is 8. In other embodiments, q is 9.

In some embodiments, each $R_1$, when present, in Formula I is independently H, D, halogen, —OH, —CN, —$NO_2$, oxo, —$C_1$-$C_6$alkyl, $C_{1-6}$alkoxide, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$.

In some embodiments, $R_1$ is independently H. In some embodiments, $R_1$ is independently D. In some embodiments, $R_1$ is independently halogen. In some embodiments, $R_1$ is independently —OH. In some embodiments, $R_1$ is independently —CN. In some embodiments, $R_1$ is independently $NO_2$. In some embodiments, $R_1$ is independently oxo. In some embodiments, $R_1$ is independently —$C_1$-$C_6$alkyl. In some embodiments, $R_1$ is independently $C_{1-6}$alkoxide. In some embodiments, $R_1$ is independently —$C_2$-$C_6$alkenyl. In some embodiments, $R_1$ is independently —$C_2$-$C_6$alkynyl. In some embodiments, $R_1$ is independently aryl. In some embodiments, $R_1$ is independently heteroaryl. In some embodiments, $R_1$ is independently cycloalkyl. In some embodiments, $R_1$ is independently cycloalkenyl. In some embodiments, each $R_1$ is independently heterocycloalkyl. In some embodiments, each $R_1$ is independently —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$, or —$S(O)_2R^b$.

In other embodiments, $R_1$ is independently heterocycloalkyl. In other embodiments, $R_1$ is independently a 6-membered heterocyclalkyl. In some embodiments, $R_1$ is independently a piperazine. In yet other embodiments, $R_1$ is independently a 7-membered heterocyclalkyl. In yet other embodiments, $R_1$ is independently a spiro-fused group. In yet other embodiments, $R_1$ is independently a diazaspiroheptane.

In other embodiments, two $R^1$ together with the carbon atom(s) to which they are both attached at same carbon or different carbones, form a carbocyclic or heterocyclic group.

In some embodiments, each $R_2$, when present, in Formula I is independently H, D, halogen, $C_1$-$C_8$ alkoxide, $C_1$-$C_8$ alkyl, haloalkyl, $SF_5$, or —CN; wherein the $C_{1-8}$ alkyl may be optionally substituted with D, halogen, —OH, —CN, or cycloalkyl. In some embodiments, $R_2$ is independently H. In some embodiments, $R_2$ is independently D. In other embodiments, $R_2$ is independently halogen. In other embodiments, $R_2$ is independently fluoro. In yet other embodiments, $R_2$ is independently $C_1$-$C_8$ alkoxide. In yet other embodiments, $R_2$ is independently $C_1$-$C_8$ alkyl. In yet other embodiments, $R_2$ is independently haloalkyl. In yet other embodiments, $R_2$ is independently $SF_5$. In yet other embodiments, $R_2$ is independently —CN. In yet other embodiments, each $R_2$ that is $C_{1-8}$alkyl is substituted with D, halogen, —OH, —CN, or cycloalkyl.

In some embodiments, each $R^a$ in Formula I is independently H, D, —$C(O)R^b$, —$C(O)OR^c$, —$C(O)NR^cR^d$, —$C(=NR^b)NR^bR^c$, —$C(=NOR^b)NR^bR^c$, —$C(=NCN)NR^bR^c$, —$P(OR^c)_2$, —$P(O)OR^cOR^b$, —$S(O)_2R^b$, —$S(O)_2NR^cR^d$, $SiR^b_3$, —$C_1$-$C_{10}$alkyl, —$C_2$-$C_{10}$ alkenyl, —$C_2$-$C_{10}$ alkynyl, $C_0$-$C_1$alk-aryl, cycloalkyl, cycloalkenyl, $C_0$-$C_1$alk-heteroaryl, heterocycloalkyl, or heterocycloalkenyl.

In some embodiments, $R^a$ is independently H. In some embodiments, $R^a$ is independently D. In some embodiments, $R^a$ is independently —C(O)$R^b$. In some embodiments, $R^a$ is independently —C(O)O$R^c$. In some embodiments, $R^a$ is independently —C(O)N$R^c R^d$. In some embodiments, $R^a$ is independently —C(=N$R^b$)N$R^b R^c$. In some embodiments, $R^a$ is independently C(=NO$R^b$)N$R^b R^c$. In some embodiments, $R^a$ is independently —C(=NCN)N$R^b R^c$.

In other embodiments, each $R^a$ is independently P(O$R^c$)$_2$, —P(O)O$R^c$O$R^b$, —S(O)$_2 R^b$, —S(O)$_2$N$R^c R^d$, or Si$R^b{}_3$. In yet other embodiments, each $R^a$ is independently —$C_1$-$C_{10}$alkyl, —$C_2$-$C_{10}$ alkenyl, —$C_2$-$C_{10}$ alkynyl, $C_0$-$C_1$alk-aryl, cycloalkyl, cycloalkenyl, $C_0$-$C_1$alk-heteroaryl, heterocycloalkyl, or heterocycloalkenyl.

In some embodiments, each $R^b$ in Formula I is independently H, D, —$C_1$-$C_6$ alkyl, —$C_2$-$C_6$ alkenyl, —$C_2$-$C_6$ alkynyl, $C_0$-$C_1$alk-aryl, cycloalkyl, cycloalkenyl, $C_0$-$C_1$alk-heteroaryl, heterocycloalkyl, or heterocycloalkenyl. In some embodiments, $R^b$ is independently H. In some embodiments, $R^b$ is independently D. In some embodiments, $R^b$ is independently —$C_1$-$C_6$ alkyl. In some embodiments, $R^b$ is independently —$C_2$-$C_6$ alkenyl. In some embodiments, $R^b$ is independently —$C_2$-$C_6$ alkynyl. In other embodiments, $R^b$ is independently $C_0$-$C_1$alk-aryl. In other embodiments, $R^b$ is independently cycloalkyl. In other embodiments, $R^b$ is independently cycloalkenyl. In other embodiments, $R^b$ is independently $C_0$-$C_1$alk-heteroaryl. In other embodiments, $R^b$ is independently heterocycloalkyl. In other embodiments, $R^b$ is independently heterocycloalkenyl.

In some embodiments, each $R^c$ in Formula I is independently H, D, —$C_1$-$C_6$ alkyl, —$C_2$-$C_6$ alkenyl, —$C_2$-$C_6$ alkynyl, aryl, $C_1$alk-aryl, cycloalkyl, cycloalkenyl, $C_1$alk-heteroaryl, heteroaryl, heterocycloalkyl, or heterocycloalkenyl. In some embodiments, $R^c$ is independently H. In some embodiments, $R^c$ is independently D. In some embodiments, $R^c$ is independently —$C_1$-$C_{10}$ alkyl. In some embodiments, $R^c$ is independently —$C_2$-$C_6$ alkenyl. In some embodiments, $R^c$ is independently —$C_2$-$C_6$ alkynyl. In other embodiments, $R^c$ is independently —O$C_1$-$C_6$alkyl. In other embodiments, $R^c$ is independently —O-cycloalkyl. In other embodiments, $R^c$ is independently aryl. In other embodiments, $R^c$ is independently $C_1$alk-aryl. In other embodiments, $R^c$ is independently cycloalkyl. In other embodiments, $R^c$ is independently cycloalkenyl. In other embodiments, $R^c$ is independently $C_1$alk-heteroaryl. In other embodiments, $R^c$ is independently heteroaryl. In other embodiments, $R^c$ is independently heterocycloalkyl. In other embodiments, $R^c$ is independently heterocycloalkenyl.

In some embodiments, each $R^d$ in Formula I is independently H, D, —$C_1$-$C_6$ alkyl, —$C_2$-$C_6$ alkenyl, —$C_2$-$C_6$ alkynyl, aryl, $C_1$alk-aryl, cycloalkyl, cycloalkenyl, $C_1$alk-heteroaryl, heteroaryl, heterocycloalkyl, or heterocycloalkenyl. In some embodiments, $R^d$ is independently H. In some embodiments, $R^d$ is independently D. In some embodiments, $R^d$ is independently —$C_1$-$C_{10}$ alkyl. In some embodiments, $R^d$ is independently —$C_2$-$C_6$ alkenyl. In some embodiments, $R^d$ is independently —$C_2$-$C_6$ alkynyl. In other embodiments, $R^d$ is independently —O$C_1$-$C_6$alkyl. In other embodiments, $R^d$ is independently —O-cycloalkyl. In other embodiments, $R^d$ is independently aryl. In other embodiments, $R^d$ is independently $C_1$alk-aryl. In other embodiments, $R^d$ is independently cycloalkyl. In other embodiments, $R^c$ or $R^d$ is independently cycloalkenyl. In other embodiments, $R^d$ is independently $C_1$alk-heteroaryl. In other embodiments, $R^d$ is independently heteroaryl. In other embodiments, $R^d$ is independently heterocycloalkyl. In other embodiments, $R^d$ is independently heterocycloalkenyl.

In yet other embodiments, $R^c$ and $R^d$, together with the atoms to which they are both attached, form a monocyclic or multicyclic heterocycloalkyl, or a monocyclic or multicyclic heterocyclo-alkenyl group. In yet other embodiments, $R^c$ and $R^d$, together with the atoms to which they are both attached, form a monocyclic heterocycloalkyl. In yet other embodiments, $R^c$ and $R^d$, together with the atoms to which they are both attached, form a multicyclic heterocycloalkyl. In yet other embodiments, $R^c$ and $R^d$, together with the atoms to which they are both attached, form a monocyclic heterocyclo-alkenyl group. In yet other embodiments, $R^c$ and $R^d$, together with the atoms to which they are both attached, form a multicyclic heterocyclo-alkenyl group.

In some embodiments, each $R_5$ in Formula I is independently H, —O$R^b$, $C_{1-4}$alkyl, wherein the $C_{1-4}$alkyl may be optionally substituted with at least one of D, halogen, —OH, —CN, an amine, cycloalkyl or heterocycloalkyl. In some embodiments, $R_5$ is H. In some embodiments, $R_5$ is —O$R^b$. In some embodiments, $R_5$ is $C_{1-4}$alkyl. In other embodiments, the $C_{1-4}$alkyl group of $R_5$ is substituted with at least one D. In other embodiments, the $C_{1-4}$alkyl group of $R_5$ is substituted with at least one halogen. In other embodiments, the $C_{1-4}$alkyl group of $R_5$ is substituted with at least one —OH. In other embodiments, the $C_{1-4}$alkyl group of $R_5$ is substituted with at least one —CN. In other embodiments, the $C_{1-4}$alkyl group of $R_5$ is substituted with at least one amine. In other embodiments, the $C_{1-4}$alkyl group of $R_5$ is substituted with cycloalkyl. In other embodiments, the $C_{1-4}$alkyl group of $R_5$ is substituted with heterocycloalkyl.

In some embodiments, each $R_6$ in Formula I is independently H, D, halogen, —OH, —CN, —NO$_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —O$R^a$, —S$R^a$, —N$R^c R^d$, —N$R^a R^c$, —C(O)$R^b$, —OC(O)$R^b$, —C(O)O$R^b$, —C(O)N$R^c R^d$, —S(O)$R^b$, —S(O)$_2$N$R^c R^d$, —S(O)(=N$R^b$)$R^b$, —SF$_5$, —P(O)$R^b R^b$, —P(O)(O$R^b$)(O$R^b$), —B(O$R^c$)(O$R^d$) or —S(O)$_2 R^b$.

In some embodiments, $R_6$ is H. In some embodiments, $R_6$ is D. In some embodiments, $R_6$ is halogen. In some embodiments, $R_6$ is —OH. In some embodiments, $R_6$ is —CN. In some embodiments, $R_6$ is NO$_2$. In some embodiments, $R_6$ is —$C_1$-$C_6$alkyl. In some embodiments, $R_6$ is —$C_2$-$C_6$alkenyl. In some embodiments, $R_6$ is —$C_2$-$C_6$alkynyl. In other embodiments, $R_6$ is aryl. In other embodiments, $R_6$ is heteroaryl. In other embodiments, $R_6$ is cycloalkyl. In other embodiments, $R_6$ is cycloalkenyl. In other embodiments, $R_6$ is heterocycloalkyl. In other embodiments, $R_6$ is heterocycloalkenyl. In other embodiments, $R_6$ is —O$R^a$, —S$R^a$, —N$R^c R^d$, —N$R^a R^c$, —C(O)$R^b$, —OC(O)$R^b$, —C(O)O$R^b$, —C(O)N$R^c R^d$, —S(O)$R^b$, —S(O)$_2$N$R^c R^d$, —S(O)(=N$R^b$)$R^b$, —SF$_5$, —P(O)$R^b R^b$, —P(O)(O$R^b$)(O$R^b$), —B(O$R^c$)(O$R^d$) or —S(O)$_2 R^b$.

In some embodiments, two $R_6$ groups together with the atom(s) to which they attached (same atom or different atoms) can form a spirocyclic group, multicyclic heterocycloalkyl, or a multicyclic cycloalkyl group;

In some embodiments, X in Formula I is O or N$R^5$. In some embodiments, X in Formula I is O. In other embodiments, X in Formula I is N$R^5$.

In some embodiments, $R_{10}$ in Formula I is H, D, —N$R^c R^d$, —N$R^a R^c$, $C_{1-6}$alkyl, $C_{3-7}$cycloalkyl, $C_{4-7}$heterocycloalkyl, $C_{3-7}$cycloalkylalkyl, $C_{4-7}$heterocycloalkylalkyl, aryl, heteroaryl, arylalkyl, heteroarylalkyl, or haloalkyl; wherein said that $C_{1-6}$alkyl, $C_{3-7}$cycloalkyl, $C_{4-7}$heterocycloalkyl, $C_{3-7}$ cycloalkylalkyl, $C_{4-7}$heterocycloalkylalkyl, aryl, heteroaryl, arylalkyl and heteroarylalkyl is optionally substituted by 1-6 R selected from H, D, halogen, —OH, —CN, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$.

In some embodiments, $R_{10}$ in Formula I is $C_{1-6}$alkyl. In some embodiments, $R_{10}$ is methyl. In other embodiments, $R_{10}$ is ethyl. In other embodiments, $R_{10}$ is propyl. In yet other embodiments, $R_{10}$ is isopropyl. In yet other embodiments, $R_{10}$ is butyl. In yet other embodiments, $R_{10}$ is t-butyl. In yet other embodiments, $R_{10}$ is pentyl. In yet other embodiments, $R_{10}$ is neopentyl. In yet other embodiments, $R_{10}$ is hexyl.

In some embodiments, the compounds of Formula (I) are the pharmaceutically acceptable salts. In some embodiments, the compounds of Formula (I) are solvates. In some embodiments, the compounds of Formula (I) are N-oxides of the compounds of Formula (I).

In some embodiments, the compounds of Formula (I) are represented by compounds of Formula II

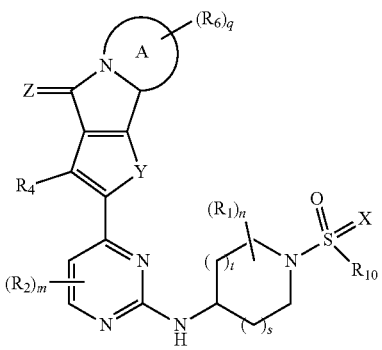

(II)

or a pharmaceutically acceptable salt or solvate or N-oxide thereof; wherein Y=S, O, NR$^5$; and wherein each $(R_1)_n$, $(R_2)_m$, $R_4$, $R_5$, $(R_6)_q$, $R_{10}$, X, Z, ring A, s and t are defined with respect to Formula (I).

In some embodiments, Y in Formula (II) is S, O, NR$^5$. In other embodiments, Y in Formula (II) is S. In other embodiments, Y in Formula (II) is O. In yet other embodiments, Y in Formula (II) is NR$^5$.

In some embodiments, the compounds of Formula (I) are represented by compounds of Formula III

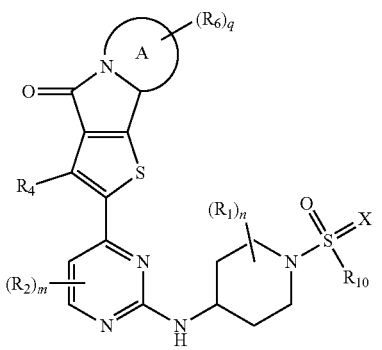

(III)

or a pharmaceutically acceptable salt or solvate or N-oxide thereof; wherein each $(R_1)_n$, $(R_2)_m$, $R_4$, $(R_6)_q$, $R_{10}$, X, and ring A are defined with respect to Formula (I).

In some embodiments, the compounds of Formula (I) are represented by compounds of Formula IV:

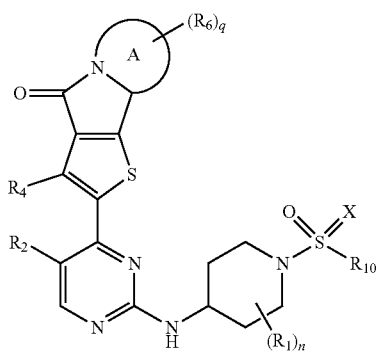

(IV)

or a pharmaceutically acceptable salt or solvate or N-oxide thereof; wherein each $(R_1)_n$, $R_2$, $R_4$, $(R_6)_q$, $R_{10}$, X, and ring A are defined with respect to Formula (I).

In some embodiments, the compounds of Formula (I) are represented by compounds of Formula V:

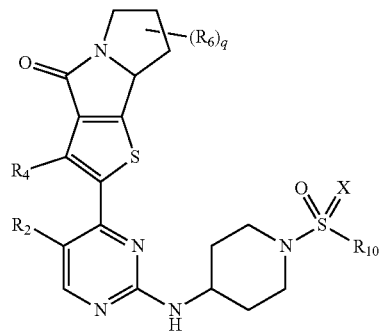

(V)

or a pharmaceutically acceptable salt or solvate or N-oxide thereof; wherein each $R_2$, $R_4$, $(R_6)_q$, X and $R_{10}$ are defined with respect to Formula (I).

In some embodiments, the compounds of Formula (I) are represented by compounds of Formula VI:

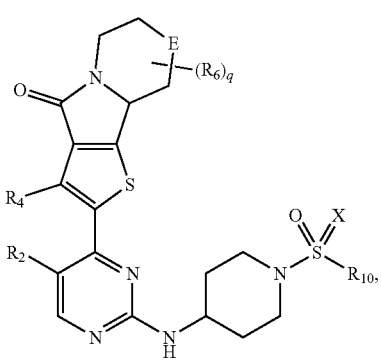

(VI)

or a pharmaceutically acceptable salt or solvate or N-oxide thereof; wherein each $R_2$, $R_4$, $(R_6)_q$, X and $R_{10}$ are defined with respect to Formula (I); and wherein E is bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$.

In some embodiments, E in Formula VI is a bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$. In some embodiments, E in Formula VI is a bond. In some embodiments, E in Formula VI is C(R$^a$)$_2$. In some embodiments, E in Formula VI is NR$^a$. In some embodiments, E in Formula VI is —O—. In some embodiments, E in Formula VI is —S—. In some embodiments, E in Formula VI is —SO—. In some embodiments, E in Formula VI is —SO$_2$—. In some embodiments, E in Formula VI is SO$_2$NR$^a$—. In some embodiments, E in Formula VI is —C(=O)NR$^a$—. In some embodiments, E in Formula VI is NR$^a$C(=O)NR$^a$. In some embodiments, E in Formula VI is NR$^a$S(O)$_2$NR$^a$.

In some embodiments, the compounds of Formula (I) are represented by compounds of Formula VII:

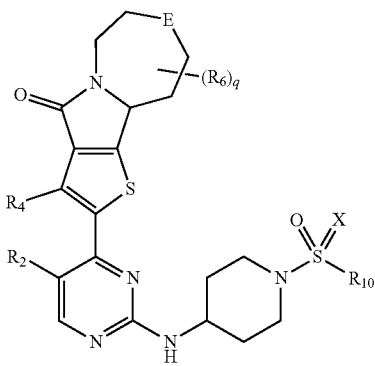

(VII)

or a pharmaceutically acceptable salt or solvate or N-oxide thereof; wherein each R$_2$, R$_4$, (R$_6$)$_q$, X and R$_{10}$ are defined with respect to Formula (I); and wherein E is bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$.

In some embodiments, E in Formula VII is a bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$. In some embodiments, E in Formula VII is a bond. In some embodiments, E in Formula VII is C(R$^a$)$_2$. In some embodiments, E in Formula VII is NR$^a$. In some embodiments, E in Formula VII is —O—. In some embodiments, E in Formula VII is —S—. In some embodiments, E in Formula VII is —SO—. In some embodiments, E in Formula VII is —SO$_2$—. In some embodiments, E in Formula VII is SO$_2$NR$^a$—. In some embodiments, E in Formula VII is —C(=O)NR$^a$—. In some embodiments, E in Formula VII is NR$^a$C(=O)NR$^a$. In some embodiments, E in Formula VII is NR$^a$S(O)$_2$NR$^a$.

In some embodiments, the compounds of Formula (I) are represented by compounds of Formula VIII:

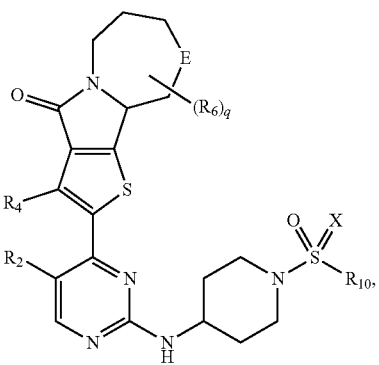

(VIII)

or a pharmaceutically acceptable salt or solvate or N-oxide thereof; wherein each R$_2$, R$_4$, (R$_6$)$_q$, X and R$_{10}$ are defined with respect to Formula (I); and wherein E is bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$.

In some embodiments, E in Formula VIII is a bond, C(R$^a$)$_2$, NR$^a$, —O—, —S—, SO, SO$_2$, SO$_2$NR$^a$, —C(=O)NR$^a$—, NR$^a$C(=O)NR$^a$, or NR$^a$S(O)$_2$NR$^a$. In some embodiments, E in Formula VIII is a bond. In some embodiments, E in Formula VIII is C(R$^a$)$_2$. In some embodiments, E in Formula VIII is NR$^a$. In some embodiments, E in Formula VIII is —O—. In some embodiments, E in Formula VIII is —S—. In some embodiments, E in Formula VIII is —SO—. In some embodiments, E in Formula VIII is —SO$_2$—. In some embodiments, E in Formula VIII is SO$_2$NR$^a$—. In some embodiments, E in Formula VIII is —C(=O)NR$^a$—. In some embodiments, E in Formula VIII is NR$^a$C(=O)NR$^a$. In some embodiments, E in Formula VIII is NR$^a$S(O)$_2$NR$^a$.

In some embodiments, the compounds of Formula (I) are represented by compounds of Formula IX:

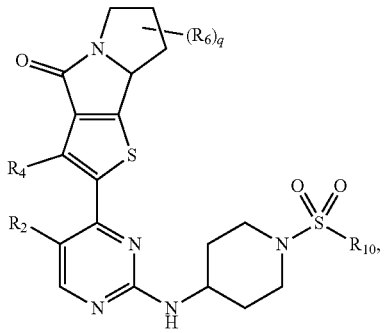

(IX)

or a pharmaceutically acceptable salt or solvate or N-oxide thereof; wherein each R$_2$, R$_4$, (R$_6$)$_q$ and R$_{10}$ are defined with respect to Formula (I).

In some embodiments, the compounds of Formula (I) are represented by compounds of Formula X:

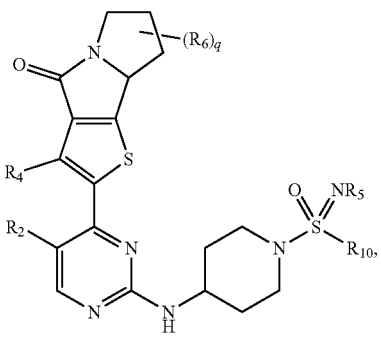

(X)

or a pharmaceutically acceptable salt or solvate or N-oxide thereof; wherein each R$_2$, R$_4$, (R$_6$)$_q$, R$_5$ and R$_{10}$ are defined with respect to Formula (I).

In some embodiments, the compounds of Formula (I) are represented by compounds of Formula XI:

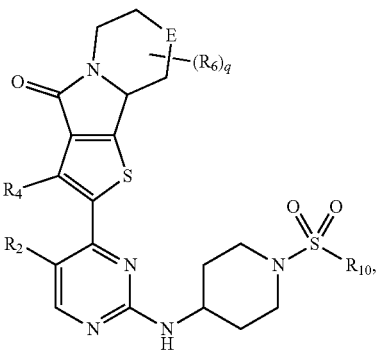

(XI)

or a pharmaceutically acceptable salt or solvate or N-oxide thereof; wherein each $R_2$, $R_4$, $(R_6)_q$, and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XI is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XI is a bond. In some embodiments, E in Formula XI is $C(R^a)_2$. In some embodiments, E in Formula XI is $NR^a$. In some embodiments, E in Formula XI is —O—. In some embodiments, E in Formula XI is —S—. In some embodiments, E in Formula XI is —SO—. In some embodiments, E in Formula XI is —$SO_2$—. In some embodiments, E in Formula XI is $SO_2NR^a$. In some embodiments, E in Formula XI is —C(=O)$NR^a$—. In some embodiments, E in Formula XI is $NR^aC(=O)NR^a$. In some embodiments, E in Formula XI is $NR^aS(O)_2NR^a$.

In some embodiments, the compounds of Formula (I) are represented by compounds of Formula XII:

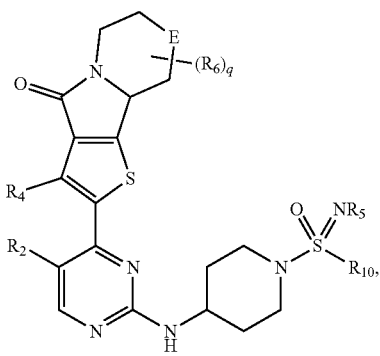

(XII)

or a pharmaceutically acceptable salt or solvate or N-oxide thereof; wherein each $R_2$, $R_4$, $(R_6)_q$, $R_5$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XII is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XII is a bond. In some embodiments, E in Formula XII is $C(R^a)_2$. In some embodiments, E in Formula XII is $NR^a$. In some embodiments, E in Formula XII is —O—. In some embodiments, E in Formula XII is —S—. In some embodiments, E in Formula XII is —SO—. In some embodiments, E in Formula XII is —$SO_2$—. In some embodiments, E in Formula XII is $SO_2NR^a$. In some embodiments, E in Formula XII is —C(=O)$NR^a$—. In some embodiments, E in Formula XII is $NR^aC(=O)NR^a$. In some embodiments, E in Formula XII is $NR^aS(O)_2NR^a$.

In some embodiments, the compounds of Formula (I) are represented by compounds of Formula XIII:

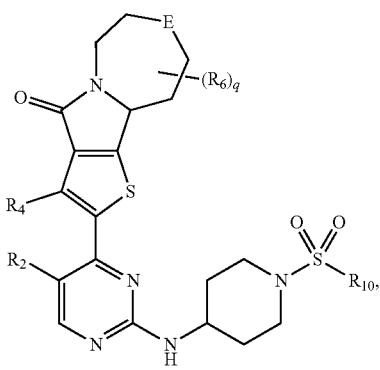

(XIII)

or a pharmaceutically acceptable salt or solvate or N-oxide thereof; wherein each $R_2$, $R_4$, $(R_6)_q$, and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XIII is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XIII is a bond. In some embodiments, E in Formula XIII is $C(R^a)_2$. In some embodiments, E in Formula XIII is $NR^a$. In some embodiments, E in Formula XIII is —O—. In some embodiments, E in Formula XIII is —S—. In some embodiments, E in Formula XIII is —SO—. In some embodiments, E in Formula XIII is —$SO_2$—. In some embodiments, E in Formula XIII is $SO_2NR^a$. In some embodiments, E in Formula XIII is —C(=O)$NR^a$—. In some embodiments, E in Formula XIII is $NR^aC(=O)NR^a$. In some embodiments, E in Formula XIII is $NR^aS(O)_2NR^a$.

In some embodiments, the compounds of Formula (I) are represented by compounds of Formula XIV:

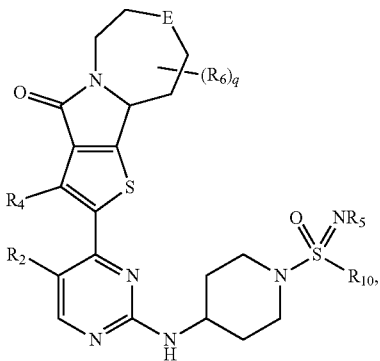

(XIV)

or a pharmaceutically acceptable salt or solvate or N-oxide thereof; wherein each $R_2$, $R_4$, $(R_6)_q$, $R_5$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XIV is a bond, C(R$^a$)$_2$, NR$^a$, —O—, —S—, SO, SO$_2$, SO$_2$NR$^a$, —C(═O)NR$^a$—, NR$^a$C(═O)NR$^a$, or NR$^a$S(O)$_2$NR$^a$. In some embodiments, E in Formula XIV is a bond. In some embodiments, E in Formula XIV is C(R$^a$)$_2$. In some embodiments, E in Formula XIV is NR$^a$. In some embodiments, E in Formula XIV is —O—. In some embodiments, E in Formula XIV is —S—. In some embodiments, E in Formula XIV is —SO—. In some embodiments, E in Formula XIV is —SO$_2$—. In some embodiments, E in Formula XIV is SO$_2$NR$^a$—. In some embodiments, E in Formula XIV is —C(═O)NR$^a$—. In some embodiments, E in Formula XIV is NR$^a$C(═O)NR$^a$. In some embodiments, E in Formula XIV is NR$^a$S(O)$_2$NR$^a$.

In some embodiments, the compounds of Formula (I) are represented by compounds of Formula XV:

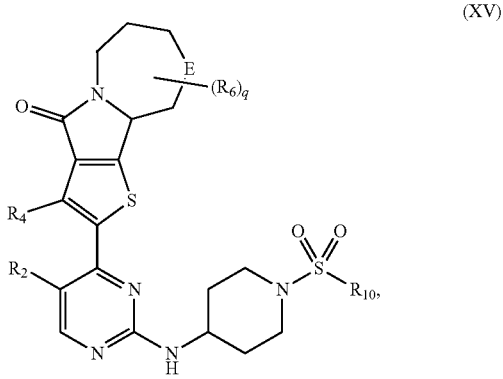

(XV)

or a pharmaceutically acceptable salt or solvate or N-oxide thereof; wherein each R$_2$, R$_4$, (R$_6$)$_q$, and R$_{10}$ are defined with respect to Formula (I); and wherein E is bond, C(R$^a$)$_2$, NR$^a$, —O—, —S—, SO, SO$_2$, SO$_2$NR$^a$, —C(═O)NR$^a$—, NR$^a$C(═O)NR$^a$, or NR$^a$S(O)$_2$NR$^a$.

In some embodiments, E in Formula XV is a bond, C(R$^a$)$_2$, NR$^a$, —O—, —S—, SO, SO$_2$, SO$_2$NR$^a$, —C(═O)NR$^a$—, NR$^a$C(═O)NR$^a$, or NR$^a$S(O)$_2$NR$^a$. In some embodiments, E in Formula XV is a bond. In some embodiments, E in Formula XV is C(R$^a$)$_2$. In some embodiments, E in Formula XV is NR$^a$. In some embodiments, E in Formula XV is —O—. In some embodiments, E in Formula XV is —S—. In some embodiments, E in Formula XV is —SO—. In some embodiments, E in Formula XV is —SO$_2$—. In some embodiments, E in Formula XV is SO$_2$NR$^a$—. In some embodiments, E in Formula XV is —C(═O)NR$^a$—. In some embodiments, E in Formula XV is NR$^a$C(═O)NR$^a$. In some embodiments, E in Formula XV is NR$^a$S(O)$_2$NR$^a$.

In some embodiments, the compounds of Formula (I) are represented by compounds of Formula XVI:

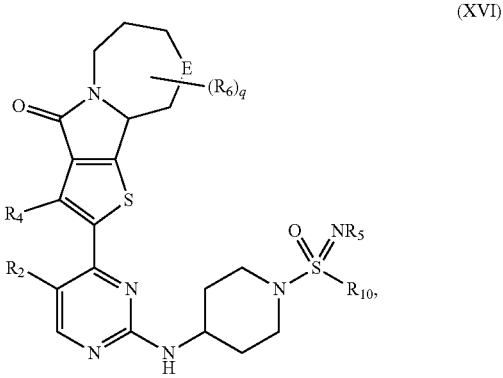

(XVI)

or a pharmaceutically acceptable salt or solvate or N-oxide thereof; wherein each R$_2$, R$_4$, (R$_6$)$_q$, R$_5$ and R$_{10}$ are defined with respect to Formula (I); and wherein E is bond, C(R$^a$)$_2$, NR$^a$, —O—, —S—, SO, SO$_2$, SO$_2$NR$^a$, —C(═O)NR$^a$—, NR$^a$C(═O)NR$^a$, or NR$^a$S(O)$_2$NR$^a$.

In some embodiments, E in Formula XVI is a bond, C(R$^a$)$_2$, NR$^a$, —O—, —S—, SO, SO$_2$, SO$_2$NR$^a$, —C(═O)NR$^a$—, NR$^a$C(═O)NR$^a$, or NR$^a$S(O)$_2$NR$^a$. In some embodiments, E in Formula XVI is a bond. In some embodiments, E in Formula XVI is C(R$^a$)$_2$. In some embodiments, E in Formula XVI is NR$^a$. In some embodiments, E in Formula XVI is —O—. In some embodiments, E in Formula XVI is —S—. In some embodiments, E in Formula XVI is —SO—. In some embodiments, E in Formula XVI is —SO$_2$—. In some embodiments, E in Formula XVI is SO$_2$NR$^a$—. In some embodiments, E in Formula XVI is —C(═O)NR$^a$—. In some embodiments, E in Formula XVI is NR$^a$C(═O)NR$^a$. In some embodiments, E in Formula XVI is NR$^a$S(O)$_2$NR$^a$.

In some embodiments, the compounds of Formula (I) are represented by compounds of Formula XVII:

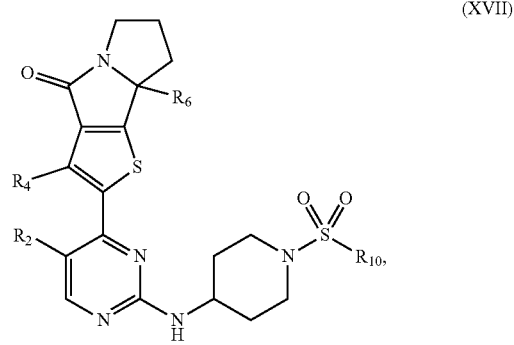

(XVII)

or a pharmaceutically acceptable salt or solvate or N-oxide thereof; wherein each R$_2$, R$_4$, R$_6$ and R$_{10}$ are defined with respect to Formula (I).

In some embodiments, the compounds of Formula (I) are represented by compounds of Formula XVIII:

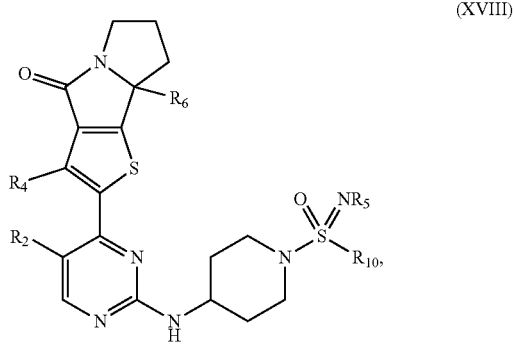

(XVIII)

or a pharmaceutically acceptable salt or solvate or N-oxide thereof; wherein each R$_2$, R$_4$, R$_6$, R$_5$ and R$_{10}$ are defined with respect to Formula (I).

In some embodiments, the compounds of Formula (I) are represented by compounds of Formula XIX:

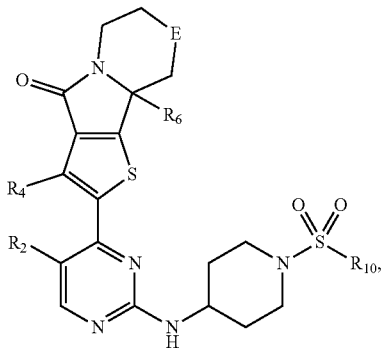

(XIX)

or a pharmaceutically acceptable salt or solvate or N-oxide thereof; wherein each $R_2$, $R_4$, $R_6$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XIX is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XIX is a bond. In some embodiments, E in Formula XIX is $C(R^a)_2$. In some embodiments, E in Formula XIX is $NR^a$. In some embodiments, E in Formula XIX is —O—. In some embodiments, E in Formula XIX is —S—. In some embodiments, E in Formula XIX is —SO—. In some embodiments, E in Formula XIX is —$SO_2$—. In some embodiments, E in Formula XIX is $SO_2NR^a$—. In some embodiments, E in Formula XIX is —C(=O)$NR^a$—. In some embodiments, E in Formula XIX is $NR^aC(=O)NR^a$. In some embodiments, E in Formula XIX is $NR^aS(O)_2NR^a$.

In some embodiments, the compounds of Formula (I) are represented by compounds of Formula XX:

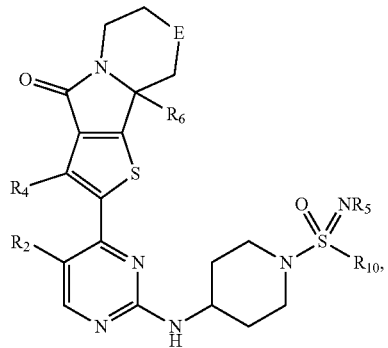

(XX)

or a pharmaceutically acceptable salt or solvate or N-oxide thereof; wherein each $R_2$, $R_4$, $R_6$, $R_5$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XX is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XX is a bond. In some embodiments, E in Formula XX is $C(R^a)_2$. In some embodiments, E in Formula XX is $NR^a$. In some embodiments, E in Formula XX is —O—. In some embodiments, E in Formula XX is —S—. In some embodiments, E in Formula XX is —SO—. In some embodiments, E in Formula XX is —$SO_2$—. In some embodiments, E in Formula XX is $SO_2NR^a$—. In some embodiments, E in Formula XX is —C(=O)$NR^a$—. In some embodiments, E in Formula XX is $NR^aC(=O)NR^a$. In some embodiments, E in Formula XX is $NR^aS(O)_2NR^a$.

In some embodiments, the compounds of Formula (I) are represented by compounds of Formula XXI:

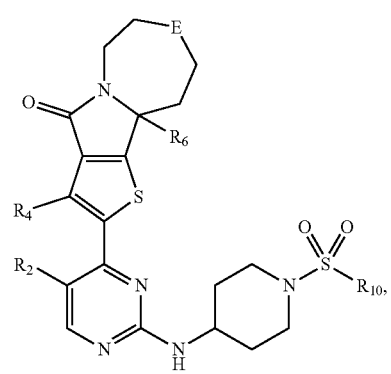

(XXI)

or a pharmaceutically acceptable salt or solvate or N-oxide thereof; wherein each $R_2$, $R_4$, $R_6$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XXI is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XXI is a bond. In some embodiments, E in Formula XXI is $C(R^a)_2$. In some embodiments, E in Formula XXI is $NR^a$. In some embodiments, E in Formula XXI is —O—. In some embodiments, E in Formula XXI is —S—. In some embodiments, E in Formula XXI is —SO—. In some embodiments, E in Formula XXI is —$SO_2$—. In some embodiments, E in Formula XXI is $SO_2NR^a$—. In some embodiments, E in Formula XXI is —C(=O)$NR^a$—. In some embodiments, E in Formula XXI is $NR^aC(=O)NR^a$. In some embodiments, E in Formula XXI is $NR^aS(O)_2NR^a$.

In some embodiments, the compounds of Formula (I) are represented by compounds of Formula XXII:

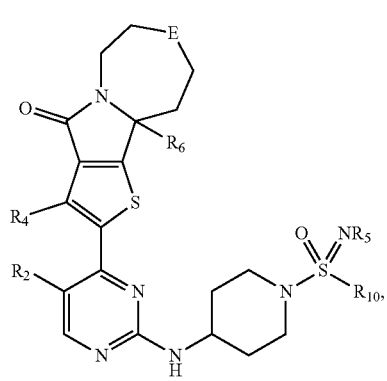

(XXII)

or a pharmaceutically acceptable salt or solvate or N-oxide thereof; wherein each $R_2$, $R_4$, $R_6$, $R_5$ and $R_{10}$ are defined with respect to Formula (I); and wherein E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$.

In some embodiments, E in Formula XXII is a bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$. In some embodiments, E in Formula XXII is a bond. In some embodiments, E in Formula XXII is $C(R^a)_2$. In some embodiments, E in Formula XXII is $NR^a$. In some embodiments, E in Formula XXII is —O—. In some embodiments, E in Formula XXII is —S—. In some embodiments, E in Formula XXII is —SO—. In some embodiments, E in Formula XXII is —$SO_2$—. In some embodiments, E in Formula XXII is $SO_2NR^a$—. In some embodiments, E in Formula XXII is —C(=O)$NR^a$—. In some embodiments, E in Formula XXII is $NR^aC(=O)NR^a$. In some embodiments, E in Formula XXII is $NR^aS(O)_2NR^a$.

In yet further embodiments, the compounds of Formula (I) are:

9a-isopropyl-2-(2-((1-(methylsulfonyl)piperidin-4-yl) amino)-5-(trifluoromethyl) pyrimidin-4-yl)-7,8,9,9a-tetrahydrothieno[2,3-a]indolizin-4(6H)-one;

(9aS)-9a-isopropyl-2-(2-((1-(methylsulfonyl)piperidin-4-yl) amino)-5-(trifluoro-methyl) pyrimidin-4-yl)-7,8,9,9a-tetrahydrothieno[2,3-a]indolizin-4(6H)-one;

(9aR) 9a-Isopropyl-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;

9a-(3-hydroxypropyl)-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;

9a-(2-hydroxyethyl)-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;

2-(5-fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one;

(9aS)-2-(5-Fluoro-2-((1-(methylsulfonyl)piperidin-4-yl) amino)pyrimidin-4-yl)-9a-methyl-7,8,9,9a-tetrahydrothieno[2,3-a]indolizin-4(6H)-one;

(9aR)-2-(5-Fluoro-2-((1-(methylsulfonyl)piperidin-4-yl) amino)pyrimidin-4-yl)-9a-methyl-7,8,9,9a-tetrahydrothieno[2,3-a]indolizin-4(6H)-one;

2-(5-Fluoro-2-((1-(methylsulfonyl)piperidin-4-yl)amino) pyrimidin-4-yl)-9a-isopropyl-7,8,9,9a-tetrahydrothieno [2,3-a]indolizin-4(6H)-one;

10a-Isopropyl-2-(2-((1-(methylsulfonyl)piperidin-4-yl) amino)-5-(trifluoromethyl) pyrimidin-4-yl)-6,7,10,10a-tetrahydrothieno[2',3':3,4]pyrrolo[1,2-d][1,4]oxazepin-4 (9H)-one;

8a-Isopropyl-2-(2-((1-(methylsulfonyl)piperidin-4-yl) amino)-5-(trifluoromethyl) pyrimidin-4-yl)-6,7,8,8a-tetrahydro-4H-thieno[2,3-a]pyrrolizin-4-one;

(8aS)-8a-Isopropyl-2-(2-((1-(methylsulfonyl)piperidin-4-yl)amino)-5-(trifluoro-methyl) pyrimidin-4-yl)-6,7,8,8a-tetrahydro-4H-thieno[2,3-a]pyrrolizin-4-one;

(8aR)-8a-Isopropyl-2-(2-((1-(methylsulfonyl)piperidin-4-yl)amino)-5-(trifluoro-methyl) pyrimidin-4-yl)-6,7,8,8a-tetrahydro-4H-thieno[2,3-a]pyrrolizin-4-one;

8a-Ethyl-2-[2-[(1-methylsulfonylpiperidin-4-yl)amino]-5-(trifluoromethyl) pyrimidin-4-yl]-7,8-dihydro-6H-thieno [2,3-a]pyrrolizin-4-one;

8a-Ethyl-2-[5-fluoro-2-[(1-methylsulfonylpiperidin-4-yl) amino]pyrimidin-4-yl]-7,8-dihydro-6H-thieno[2,3-a]pyrrolizin-4-one;

8a-Ethyl-2-[5-methyl-2-[(1-methylsulfonylpiperidin-4-yl) amino]pyrimidin-4-yl]-7,8-dihydro-6H-thieno[2,3-a]pyrrolizin-4-one;

or a pharmaceutically acceptable salt thereof.

In yet further embodiments, the compounds of Formula (I) are:

8a-(Hydroxymethyl)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-(Fluoromethyl)-2-(2-((1-(methylsulfonyl)piperidin-4-yl) amino)-5-(trifluoromethyl) pyrimidin-4-yl)-6,7,8,8a-tetrahydro-4H-thieno[2,3-a]pyrrolizin-4-one;

8a-(2-Fluoroethyl)-2-(2-((1-(methylsulfonyl)piperidin-4-yl) amino)-5-(trifluoromethyl) pyrimidin-4-yl)-6,7,8,8a-tetrahydro-4H-thieno[2,3-a]pyrrolizin-4-one;

8a-Methyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

2-(2-((1-(Methylsulfonyl)piperidin-4-yl)amino)-5-(trifluoromethyl)pyrimidin-4-yl)-6,7,8,8a-tetrahydro-4H-thieno [2,3-a]pyrrolizin-4-one;

8a-Cyclopropyl-2-(2-((1-(methylsulfonyl)piperidin-4-yl) amino)-5-(trifluoromethyl) pyrimidin-4-yl)-6,7,8,8a-tetrahydro-4H-thieno[2,3-a]pyrrolizin-4-one;

8a-Cyclobutyl-2-(2-((1-(methylsulfonyl)piperidin-4-yl) amino)-5-(trifluoromethyl)pyrimidin-4-yl)-6,7,8,8a-tetrahydro-4H-thieno[2,3-a]pyrrolizin-4-one;

8a-(3,3-Difluorocyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-(3-Hydroxycyclobutyl)-2-(2-((1-(methylsulfonyl)piperidin-4-yl)amino)-5-(trifluoromethyl)pyrimidin-4-yl)-6,7, 8,8a-tetrahydro-4H-thieno[2,3-a]pyrrolizin-4-one;

8a-(3-Fluorocyclobutyl)-2-(2-((1-(methylsulfonyl)piperidin-4-yl)amino)-5-(trifluoromethyl)pyrimidin-4-yl)-6,7, 8,8a-tetrahydro-4H-thieno[2,3-a]pyrrolizin-4-one;

2-(5-Chloro-2-((1-(methylsulfonyl)piperidin-4-yl)amino) pyrimidin-4-yl)-8a-ethyl-6,7,8,8a-tetrahydro-4H-thieno [2,3-a]pyrrolizin-4-one;

8a-Ethyl-2-(2-((1-(methylsulfonyl)piperidin-4-yl)amino) pyrimidin-4-yl)-6,7,8,8a-tetrahydro-4H-thieno[2,3-a]pyrrolizin-4-one;

7-Hydroxy-8a-isopropyl-2-(2-((1-(methylsulfonyl)piperidin-4-yl)amino)-5-(trifluoromethyl) pyrimidin-4-yl)-6,7, 8,8a-tetrahydro-4H-thieno[2,3-a]pyrrolizin-4-one;

8a-Isopropyl-7-methoxy-2-(2-((1-(methylsulfonyl)piperidin-4-yl)amino)-5-(trifluoromethyl) pyrimidin-4-yl)-6,7, 8,8a-tetrahydro-4H-thieno[2,3-a]pyrrolizin-4-one;

7-(Hydroxymethyl)-8a-isopropyl-2-(2-((1-(methylsulfonyl) piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7,7-difluoro-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-hydroxy-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-hydroxy-7-methyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7,7-difluoro-2-(2-((1-((1-methyl-1H-pyrazol-4-yl) sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7-hydroxy-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7-(methylamino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-(Dimethylamino)-8a-ethyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-Amino-8a-ethyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-(ethylamino)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-((methyl-d3)amino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-(((3R,4S)-3-methyl-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-(((3R,4S)-3-methyl-1-((1-methyl-1H-pyrazol-4-yl)sulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

7-Amino-8a-ethyl-2-(2-(((3R,4S)-3-methyl-1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-Amino-8a-ethyl-2-(2-(((3R,4S)-3-methyl-1-((1-methyl-1H-pyrazol-4-yl)sulfonyl) piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-(((3R,4R)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-(((3R,4S)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-((1-((1-methyl-1H-pyrazol-4-yl)sulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

7-(Dimethylamino)-8a-ethyl-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

or a pharmaceutically acceptable salt thereof.

It will be apparent that the compounds of Formula I, including all subgenera described herein, may have multiple stereogenic centers. As a result, there exist multiple stereoisomers (enantiomers and diastereomers) of the compounds of Formula I (and subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

Pharmaceutical Compositions and Methods of Administration

In some embodiments, the disclosure is directed to pharmaceutical compositions comprising compounds of Formula I, or a pharmaceutically acceptable salt or solvate thereof.

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof, carnitine fatty acid ester salts; salts of alkylsulfates; fatty acid salts; sodium docusate; acyl lactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10leate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (etherester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a CDK inhibitor with an IC50 value of about or less than a predetermined value, as ascertained in an in vitro assay. In some embodiments, the CDK inhibitor inhibits CDK a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the CDK inhibitor selectively inhibits CDK a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other CDKs.

In some embodiments, the CDK inhibitor selectively inhibits CDK a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other CDKs.

The subject methods are useful for treating a disease condition associated with CDK. Any disease condition that results directly or indirectly from an abnormal activity or expression level of CDK can be an intended disease condition.

Different disease conditions associated with CDK have been reported. CDK has been implicated, for example, auto-immune diseases, neurodegeneration (such as Parkinson's disease, Alzheimer's disease and ischaemia), inflammatory diseases, viral infections and cancer such as, for example, colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS) or epidermoid cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In some embodiments, the disclosure is directed to methods for treating a CDK4-mediated and a CDK6-mediated disorder in a patient in need thereof, comprising administering to said patient a compound of Formula I, including all subgenera described herein, or a pharmaceutically acceptable salt thereof, or a pharmaceutical composition comprising the compound of Formula I, including all subgenera described herein.

In some embodiments, the CDK4-mediated and CDK6-mediated disorder is a cancer. In some embodiments, the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

In some embodiments, the cancer is breast cancer. In some embodiments, the cancer is malignant brain tumors. In some embodiments, the cancer is colon cancer. In some embodiments, the cancer is small-cell lung cancer. In some embodiments, the cancer is non-small-cell lung cancer. In some embodiments, the cancer is bladder cancer. In some embodiments, the cancer is ovarian cancer.

In some embodiments, the cancer is prostate cancer. In some embodiments, the cancer is chronic lymphoid leukemia. In some embodiments, the cancer is lymphoma. In some embodiments, the cancer is myeloma. In some embodiments, the cancer is acute myeloid leukemia. In some embodiments, the cancer is secondary pancreatic cancer. In some embodiments, the cancer is secondary brain metastases.

In some embodiments, the breast cancer is HR+/HER2− or HR+/HER2+ advanced or metastatic breast cancer. In some embodiments, the breast cancer is HR+/HER2− advanced breast cancer. In some embodiments, the breast cancer is HR+/HER2− metastatic breast cancer. In some embodiments, the breast cancer is HR+/HER2+ advanced breast cancer. In some embodiments, the breast cancer is HR+/HER2+ metastatic breast cancer.

In some embodiments, the malignant brain tumors are glioblastoma, astrocytoma, or pontine glioma. In some embodiments, the malignant brain tumors are a glioblastoma. In some embodiments, the malignant brain tumors are an astrocytoma. In some embodiments, the malignant brain tumors are a pontine glioma.

In some embodiments, the patient is administered a pharmaceutical composition comprising a compound of Formula I, including all subgenera described herein, or a pharmaceutically acceptable salt thereof. In some embodiments, the administration is oral administration.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

In some embodiments, the disclosure is directed to methods described herein, further comprising administering an additional therapeutic agent to the patient. In some embodiments, the additional therapeutic agent is a PRMT5 inhibitor, a HER2 kinase inhibitor, an aromatase inhibitor, an estrogen receptor antagonist or an alkylating agent.

In some embodiments, the additional therapeutic agent is a PRMT5 inhibitor. In some embodiments, the additional therapeutic agent is a HER2 kinase inhibitor. In other embodiments, the additional therapeutic agent is an aromatase inhibitor. In other embodiments, the additional therapeutic agent is an estrogen receptor antagonist. In yet other embodiments, the additional therapeutic agent is an alkylating agent.

In some embodiments, the aromatase inhibitor is letrozole. In some embodiments, the estrogen receptor antagonist is fulvestrant. In other embodiments, the alkylating agent is temozolomide.

In yet other embodiments, the PRMT5 inhibitor is a compound disclosed in US Published Patent Application No. 2020/0148692 (filed Jan. 16, 2020); US Published Patent Application No. 2019/0284193 (filed Apr. 5, 2019); and US Published Patent Application No. 2019/0048014 (filed Aug. 9, 2018); each of which is hereby incorporated herein in its entirety.

In some embodiments, the PRMT5 inhibitor is:
(2R,3R,4S,5S)-2-(4-amino-7H-pyrrolo[2,3-d]pyrimidin-7-yl)-5-((R)-6-chloroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-7-chloroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-5-chloroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-6,7-difluoroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-5,6-difluoroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-6-chloro-5-fluoroisochroman-1-yl)tetrahydrofuran-3,4-diol, or a pharmaceutically acceptable salt or solvate thereof;

(2R,3R,4S,5S)-2-(4-amino-5-fluoro-7H-pyrrolo[2,3-d]
pyrimidin-7-yl)-5-((R)-6-chloroisochroman-1-yl)tetra-
hydrofuran-3,4-diol, or a pharmaceutically acceptable
salt or solvate thereof;

(2R,3R,4S,5S)-2-(4-amino-7H-pyrrolo[2,3-d]pyrimidin-
7-yl)-5-((R)-6,7-dichloroisochroman-1-yl)tetrahydro-
furan-3,4-diol, or a pharmaceutically acceptable salt or
solvate thereof;

(2S,3S,4R,5R)-2-((R)-6-chloroisochroman-1-yl)-5-(4-
methyl-7H-pyrrolo[2,3-d]pyrimidin-7-yl)tetrahydro-
furan-3,4-diol, or a pharmaceutically acceptable salt or
solvate thereof;

(2S,3S,4R,5R)-2-((R)-6,7-difluoroisochroman-1-yl)-5-
(4-methyl-7H-pyrrolo[2,3-d]pyrimidin-7-yl)tetrahy-
drofuran-3,4-diol, or a pharmaceutically acceptable salt
or solvate thereof;

(2S,3S,4R,5R)-2-((R)-5,6-difluoroisochroman-1-yl)-5-
(4-methyl-7H-pyrrolo[2,3-d]pyrimidin-7-yl)tetrahy-
drofuran-3,4-diol, or a pharmaceutically acceptable salt
or solvate thereof;

(2S,3S,4R,5R)-2-((R)-6-chloroisochroman-1-yl)-5-(5-
fluoro-4-methyl-7H-pyrrolo[2,3-d]pyrimidin-7-yl)tet-
rahydrofuran-3,4-diol, or a pharmaceutically accept-
able salt or solvate thereof;

(2S,3S,4R,5R)-2-((R)-6,7-dichloroisochroman-1-yl)-5-
(4-methyl-7H-pyrrolo[2,3-d]pyrimidin-7-yl)tetrahy-
drofuran-3,4-diol, or a pharmaceutically acceptable salt
or solvate thereof.

In some embodiments, the PRMT5 inhibitor is (2S,3S,
4R,5R)-2-((R)-6-chloroisochroman-1-yl)-5-(4-methyl-7H-
pyrrolo[2,3-d]pyrimidin-7-yl)tetrahydrofuran-3,4-diol, or a
pharmaceutically acceptable salt or solvate thereof.

Synthesis

Compounds of the invention, including salts thereof, can
be prepared using known organic synthesis techniques and
can be synthesized according to any of numerous possible
synthetic routes.

The reactions for preparing compounds of the invention
can be carried out in suitable solvents which can be readily
selected by one of skill in the art of organic synthesis.
Suitable solvents can be substantially nonreactive with the
starting materials (reactants), the intermediates, or products
at the temperatures at which the reactions are carried out,
e.g., temperatures which can range from the solvent's freez-
ing temperature to the solvent's boiling temperature. A given
reaction can be carried out in one solvent or a mixture of
more than one solvent. Depending on the particular reaction
step, suitable solvents for a particular reaction step can be
selected by the skilled artisan.

Preparation of compounds of the invention can involve
the protection and deprotection of various chemical groups.
The need for protection and deprotection, and the selection
of appropriate protecting groups, can be readily determined
by one skilled in the art. The chemistry of protecting groups
can be found, for example, in T. W. Greene and P. G. M.
Wuts, Protective Groups in Organic Synthesis, 3rd. Ed.,
Wiley & Sons, Inc., New York (1999), which is incorporated
herein by reference in its entirety.

Reactions can be monitored according to any suitable
method known in the art. For example, product formation
can be monitored by spectroscopic means, such as nuclear
magnetic resonance spectroscopy (e.g., $^1$H or $^{13}$C), infrared
spectroscopy, spectrophotometry (e.g., UV-visible), or mass
spectrometry, or by chromatography such as high perfor-
mance liquid chromatography (HPLC) or thin layer chro-
matography.

The expressions, "ambient temperature," "room tempera-
ture," and "r.t." as used herein, are understood in the art, and
refer generally to a temperature, e.g. a reaction temperature,
that is about the temperature of the room in which the
reaction is carried out, for example, a temperature from
about 20° C. to about 30° C.

Compounds of the invention can be prepared using
numerous preparatory reactions known in the literature. The
Schemes below provide general guidance in connection with
preparing the compounds of the invention. One skilled in the
art would understand that the preparations shown in the
Schemes can be modified or optimized using general knowl-
edge of organic chemistry to prepare various compounds of
the invention. Example synthetic methods for preparing
compounds of the invention are provided in the Schemes
below.

The following Examples are provided to illustrate some of
the concepts described within this disclosure. While the
Examples are considered to provide an embodiment, it
should not be considered to limit the more general embodi-
ments described herein.

EXAMPLES

General Synthetic Procedures

Compounds of Formula (I) can be prepared from option-
ally protected compounds 1-1 where $W^1$ is halogen (e.g., Cl,
Br, or I) or pseudohalogen (e.g., OTf or OMs) as shown in
Scheme 1. Compounds 1-1 can be coupled with compounds
1-2 where $M^1$ is a boronic acid, boronate ester, potassium
trifluoroborate, or an appropriately substituted metal, such as
Sn(Bu)$_3$, Sn(Me)$_3$, or ZnCl, under standard Suzuki condi-
tions (e.g., in the presence of a palladium catalyst, such as
[1,1'-bis(diphenyl-phosphino)ferrocene]dichloropalladium
(II) and a base, such as K$_3$PO$_4$) or standard Stille conditions
(e.g., in the presence of a palladium(0) catalyst, such as
tetrakis(triphenyl-phosphine)palladium(0)) or standard
Negishi conditions (e.g., in the presence of a palladium
catalyst, such as tetrakis (triphenylphosphine)palladium(0)
or [1,1'-bis(diphenylphosphino) ferrocene]dichloropalladiu-
m(II)), to give compounds 1-3 where $W^2$ is halogen (e.g., Cl,
Br, or I) or pseudohalogen (e.g., OTf or OMs). Coupling of
compounds 1-3 with amines 1-4 under standard Buchwald-
Hartwig amination conditions (e.g., in the presence of a
palladium catalyst, such as XPhos Pd G3, and a base, such
as Cs$_2$CO$_3$ or K$_3$PO$_4$) can provide compounds of Formula
(I).

Alternatively, compounds 1-1 can be converted to the
appropriate compounds 1-5 (e.g., $M^2$ is B(OH)$_2$, Bpin,
BF$_3$K, Sn(Me)$_3$, Sn(Bu)$_3$, or ZnCl) and then coupled to
compounds 1-6 where $W^3$ is halogen (e.g., Cl, Br, or I) or
pseudohalogen (e.g., OTf or OMs) under standard Suzuki
conditions (e.g., in the presence of a palladium catalyst, such
as [1,1'-bis(diphenylphosphino) ferrocene] dichloropalla-
dium(II), and a base, such as K$_3$PO$_4$) or standard Stille
conditions (e.g., in the presence of a palladium(0) catalyst,
such as tetrakis(triphenylphosphine)palladium(0)) or stan-
dard Negishi conditions (e.g., in the presence of a palladium
catalyst, such as tetrakis (triphenylphosphine) palladium(0)
or [1,1'-bis(diphenylphosphino)ferrocene]dichloropalla-
dium(II)) to give compounds 1-3, which can be used to
synthesize compound of Formula (I).

Scheme 1

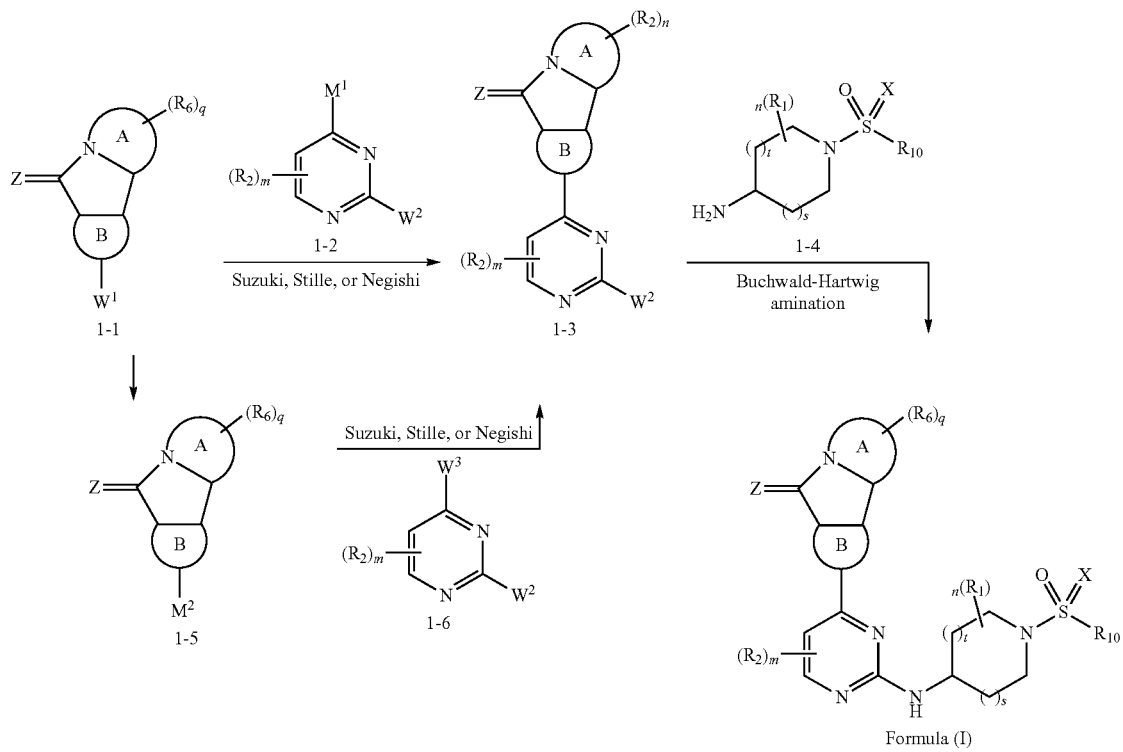

Intermediates for the synthesis of compounds of Formula (I) can be prepared as described in Scheme 2. Compounds 2-1 can be halogenated with suitable reagents, such as N-bromosuccinimide or N-iodosuccinimide, to provide compounds 1-1. Alternatively, compounds 2-1 can be metalated in the presence of a strong base, such as lithium diisopropylamide or butyllithium, and an appropriate reagent (e.g., 2-isopropoxy-4,4,5,5-tetramethyl-1,3,2-dioxaborolane, hexamethylditin, trimethyltin chloride, or zinc chloride) to afford compounds 1-5.

Scheme 2

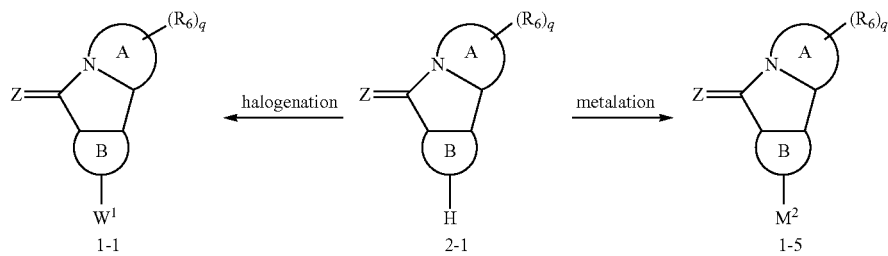

Compounds of Formula (II) can be prepared from optionally protected compounds 3-1 where $W^1$ is halogen (e.g., Cl, Br, or I) or pseudohalogen (e.g., OTf or OMs) as shown in Scheme 3. Compounds 3-1 can be coupled with compounds 3-2 where $M^1$ is a boronic acid, boronate ester, potassium trifluoroborate, or an appropriately substituted metal, such as $Sn(Bu)_3$, $Sn(Me)_3$, or ZnCl under standard Suzuki conditions (e.g., in the presence of a palladium catalyst, such as [1,1'-bis (diphenylphosphino)ferrocene]dichloropalladium (II) and a base, such as $K_3PO_4$) or standard Stille conditions (e.g., in the presence of a palladium(0) catalyst, such as tetrakis(triphenylphosphine) palladium(0)) or standard Negishi conditions (e.g., in the presence of a palladium catalyst, such as tetrakis(triphenylphosphine)palladium(0) or [1,1'-bis(diphenylphosphino)ferrocene]dichloro-palladium(II)), to give compounds 3-3 where $W^2$ is halogen (e.g., Cl, Br, or I) or pseudohalogen (e.g., OTf or OMs). Coupling of compounds 3-3 with amines 3-4 under standard Buchwald-Hartwig amination conditions (e.g., in the presence of a palladium catalyst, such as XPhos Pd G3, and a base, such as $Cs_2CO_3$ or $K_3PO_4$) can provide compounds of Formula (II).

Alternatively, compounds 3-1 can be converted to the appropriate compounds 3-5 (e.g., $M^2$ is $B(OH)_2$, Bpin, $BF_3K$, $Sn(Me)_3$, $Sn(Bu)_3$, or ZnCl) and then coupled to 5-6 where $W^3$ is halogen (e.g., Cl, Br, or I) or pseudohalogen (e.g., OTf or OMs) under standard Suzuki conditions (e.g., in the presence of a palladium catalyst, such as [1,1'-bis (diphenylphosphino)ferrocene]dichloro-palladium(II), and a base, such as $K_3PO_4$) or standard Stille conditions (e.g., in the presence of a palladium(0) catalyst, such as tetrakis (triphenylphosphine)palladium(0)) or standard Negishi conditions (e.g., in the presence of a palladium catalyst, such as tetrakis(triphenylphosphine) palladium(0) or [1,1'-bis(diphenylphosphino)ferrocene]dichloropalladium(II)) to give compounds 3-3, which can be used to synthesize compound of Formula (II).

Scheme 3

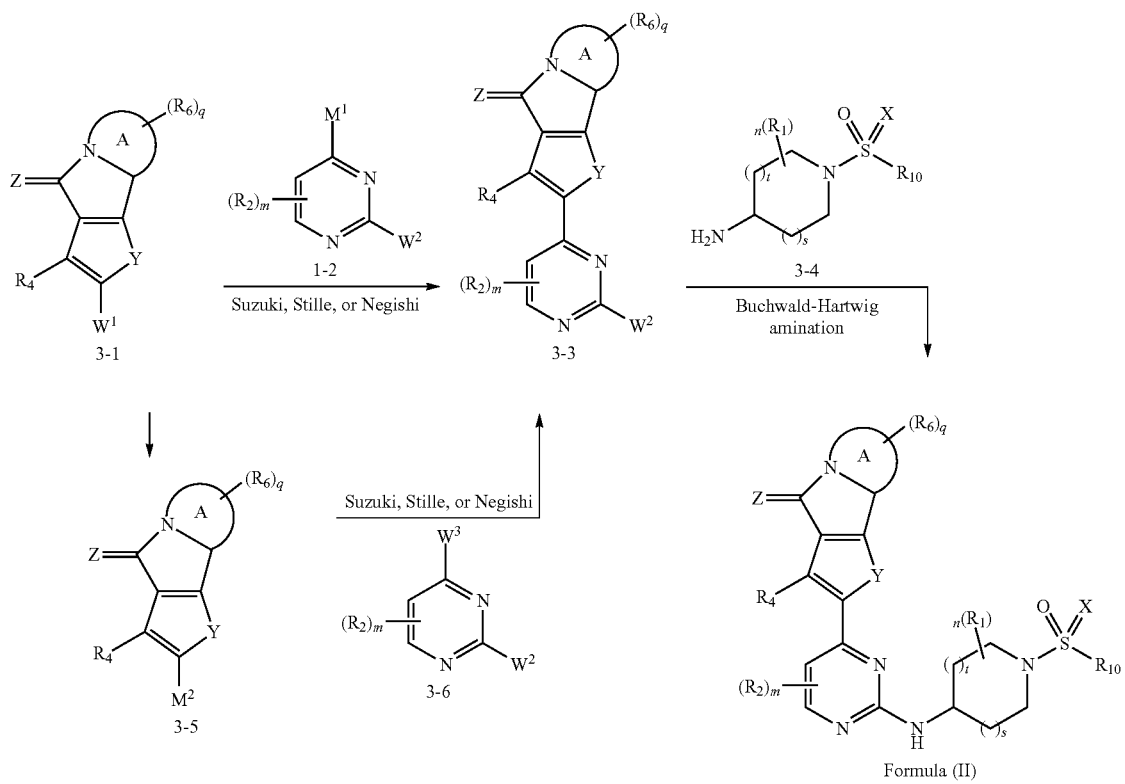

Intermediates for the synthesis of compounds of Formula (II) can be prepared as described in Scheme 4. Compounds 4-1 can be halogenated with suitable reagents, such as N-bromosuccinimide or N-iodosuccinimide, to provide compounds 4-2. Alternatively, compound 6-1 can be metalated in the presence of a strong base, such as lithium diisopropylamide or butyllithium, and an appropriate reagent (e.g., 2-isopropoxy-4,4,5,5-tetramethyl-1,3,2-dioxaborolane, hexamethylditin, trimethyltin chloride, or zinc chloride) to afford compounds 4-3.

Scheme 4

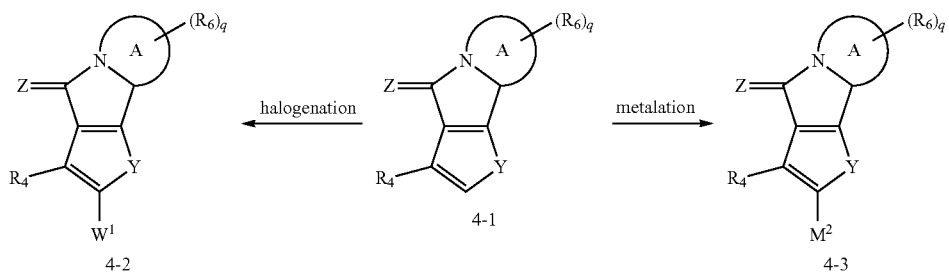

Compounds of Formula (IA) can be prepared by the methods described in Scheme 5. Optionally protected 5-1 where $W^1$ is halogen (e.g., Cl, Br, or I) or pseudohalogen (e.g., SO$_2$Me, OTs, OTf or OMs) can be coupled with compounds 5-2 where $M^1$ is a boronic acid, boronate ester, potassium trifluoroborate, or an appropriately substituted metal, such as Sn(Bu)$_3$ or ZnCl under standard Suzuki conditions (e.g., in the presence of a palladium catalyst, such as [1,1'-bis(diphenyl-phosphino)ferrocene]dichloropalladium(II) and a base, such as K$_3$PO$_4$) or standard Stille conditions (e.g., in the presence of a palladium(0) catalyst, such as tetrakis(triphenyl-phosphine)palladium(0)) or standard Negishi conditions (e.g., in the presence of a palladium catalyst, such as tetrakis(tri-phenylphosphine)palladium(0) or [1,1'-bis(diphenylphosphino)ferrocene]dichloropalladium(II)), to give compounds 5-3 where $W^2$ is halogen (e.g., Cl, Br, or I) or pseudohalogen (e.g., SO$_2$Me, OTs, OTf or OMs). Coupling of compounds 5-3 with amines 5-4 under standard Buchwald-Hartwig amination conditions (e.g., in the presence of a palladium catalyst, such as XPhos Pd G2, and a base, such as K$_3$PO$_4$) can provide compounds of Formula (IA).

Alternatively, compounds 5-1 can be converted to the appropriate compounds 5-5 (e.g., $M^2$ is B(OH)$_2$, Bpin, BF$_3$K, Sn(Me)$_3$, Sn(Bu)$_3$, or ZnCl) and then coupled to 5-6 where $W^3$ is halogen (e.g., Cl, Br, or I) or pseudohalogen (e.g., SO$_2$Me, OTs, OTf or OMs) under standard Suzuki conditions (e.g., in the presence of a palladium catalyst, such as [1,1'-bis(diphenylphosphino) ferrocene]dichloro-palladium(II), and a base, such as K$_3$PO$_4$) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis (triphenylphosphine) palladium (0) or [1,1'-bis(diphenylphosphino)ferrocene] dichloropalladium(II)) to give compounds 5-3, which can be used to synthesize compound of Formula (IA).

In a similar manner, compounds 5-6 can react with amines 5-4 to provide compounds 5-7 under amination conditions (e.g., in the presence of a Zn catalyst, such as ZnCl$_2$, and a base, such as Et$_3$N) can provide compounds of 5-7 which then can be converted to the compound of Formula (IA) by reactions with 5-1 or 5-5 under standard Suzuki, Stille or Negishi conditions described above.

Scheme 5

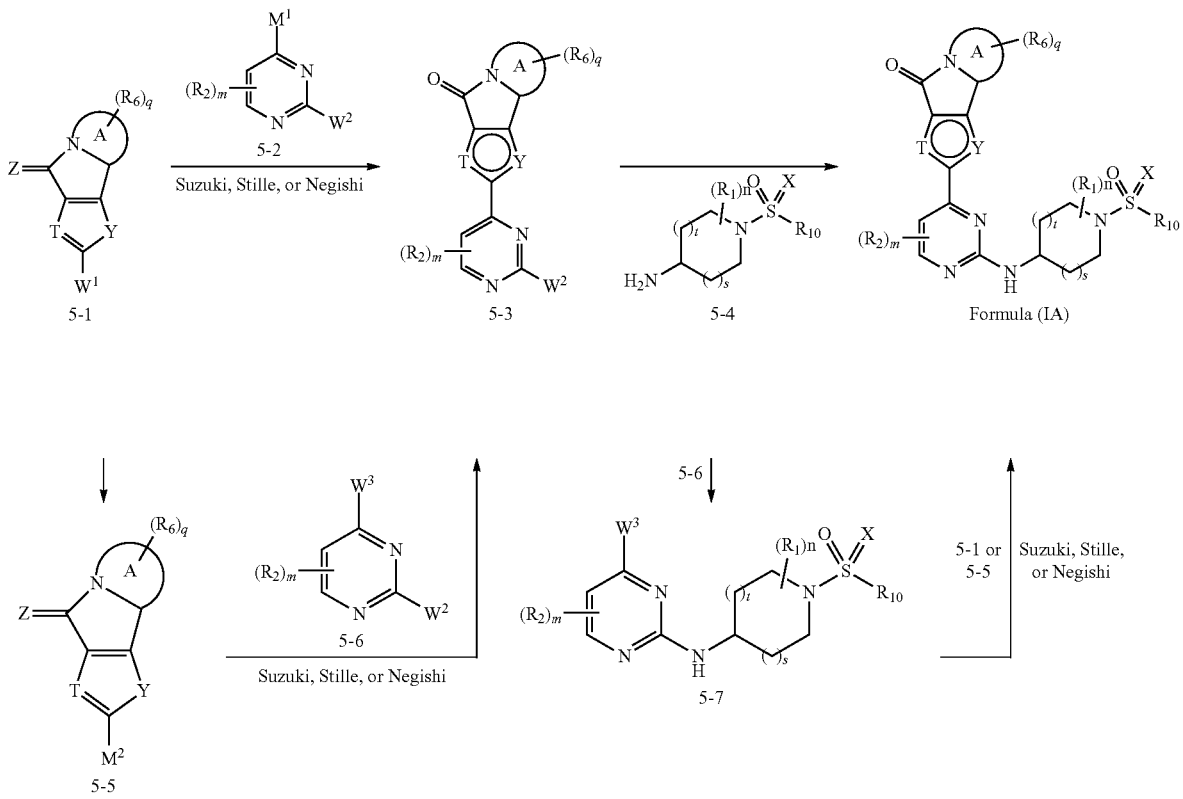

Compounds of Formula (IB) can be prepared by the methods described in Scheme 6. Coupling of compounds 6-1 with intermediates 6-2 under standard Buchwald-Hartwig amination conditions (e.g., in the presence of a palladium catalyst, such as XPhos Pd G2, and a base, such as K$_3$PO$_4$) can provide compounds of Formula (IB).

Alternatively, compounds 6-1 can be converted to the appropriate compounds 6-4 by reactions with compounds 6-3 where $W^3$ is halogen (e.g., Cl, Br, or I) or pseudohalogen (e.g., $SO_2Me$, OTs, OTf or OMs) under amination replacement conditions (e.g., in the presence of a base, such as $Et_3N$ or hunig's base). Compounds 6-4 can be used to synthesize compound of Formula (IB) under standard Buchwald-Hartwig amination conditions.

Scheme 6

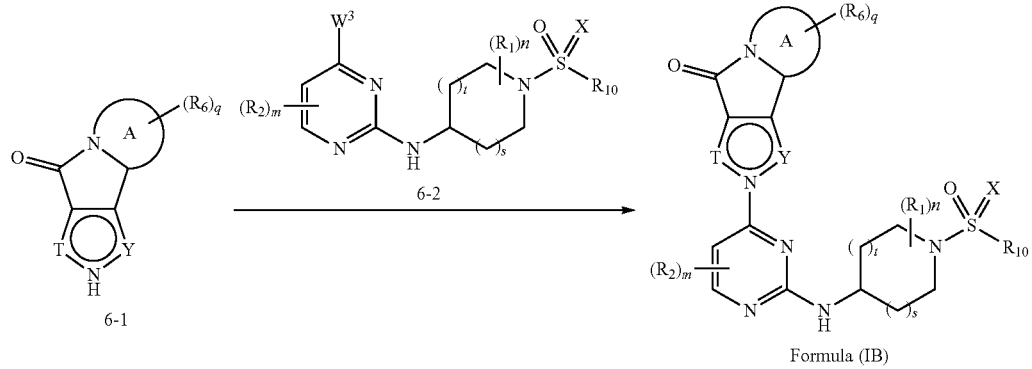

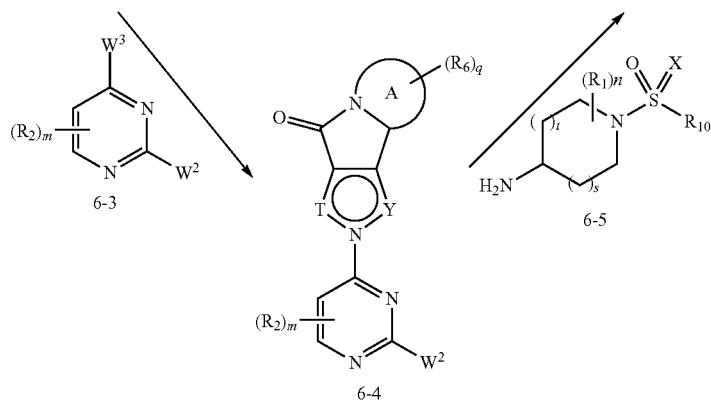

Compounds of Formula (II) can be prepared by the methods described in Scheme 7. Coupling of compounds 7-1 where Y is S, O, or $NR^9$ with pyrimidines 7-2 where $W^2$ is halogen (e.g., Cl, Br, or I) or pseudohalogen (e.g., $SO_2Me$, OTs, OTf or OMs) in the presence of a strong base (such as LDA, BuLi etc.) and subsequent addition DDQ can provide the appropriate intermediates 7-3 which can be converted to the compounds of formula (II) by reaction with the amines 7-4 under standard Buchwald-Hartwig amination conditions.

Scheme 7

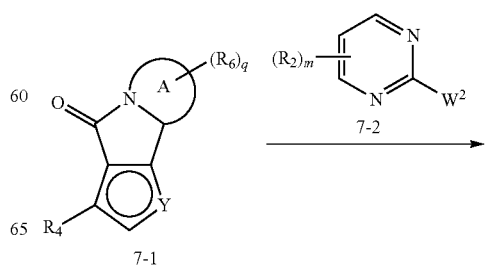

-continued

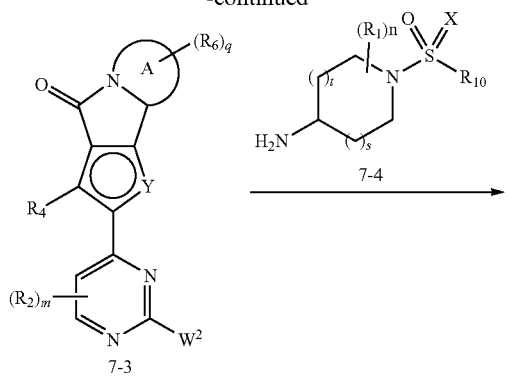

7-3

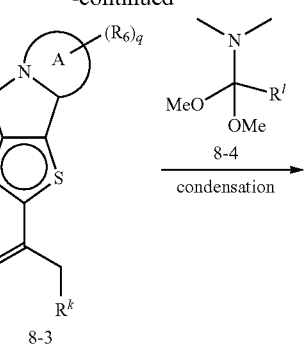

7-4

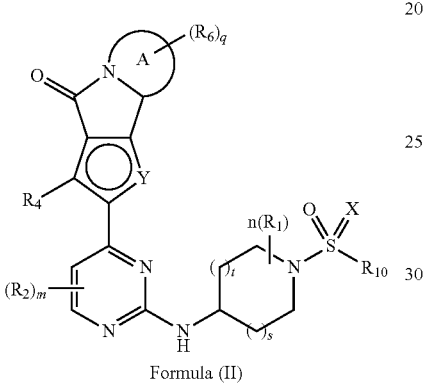

Formula (II)

Compounds of Formula (III) can be prepared as described in Scheme 8. Friedel-Crafts acylation of compounds 8-1 with acid halides 8-2 where $R^k$ is H, D, F, $C_1$-$C_8$ alkoxide, —$C_1$-$C_8$ alkyl, fluoroalkyl, or CN and $Y^9$ is a halogen (e.g., Cl or Br) under standard conditions, such as in the presence of a Lewis acid (e.g., $AlCl_3$), can afford ketones 8-3. Condensation of compounds 8-2 with acetal 8-4 where $R^1$ is H, D, —$C_1$-$C_8$ alkoxide, —$C_1$-$C_8$ alkyl, fluoroalkyl, or CN can afford compounds 8-5. Subsequent condensation of compounds 8-5 with guanidine 8-6 or one of its salts (e.g., guanidine hydrochloride) optionally in the presence of a base (e.g., $K_2CO_3$) can afford amino pyrimidines of Formula (III).

Scheme 8

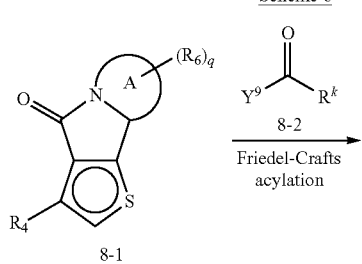

-continued

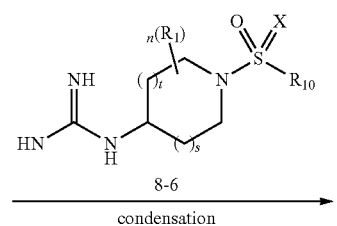

8-3

8-4
condensation

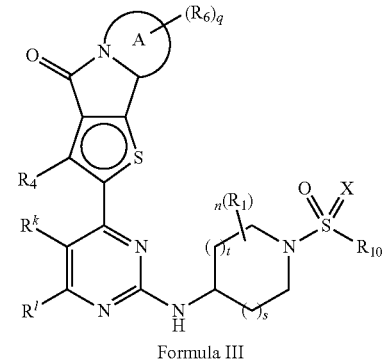

8-5

8-6
condensation

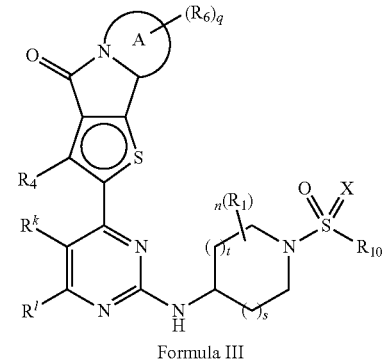

Formula III

Intermediates 10-7 for the synthesis of compounds of Formula (IA-C) can be prepared as the methods described in Scheme 10. Lithiation of thiophene acids 10-1 ($W^4$ is H, Br, or I) with a strong base, such as butyllithium, and subsequent addition N-alkyl-2-methylpropane-2-sulfinamides 10-2 can provide the corresponding thiophen acids 10-3 which can be converted to the lactams 10-4 under the amide coupling conditions in the presence of a coupling reagent (e.g., N,N'-dicyclohexylcarbodiimide or HATU, etc.). Removal of the sulfinamide group can yield lactams 10-5 which can be converted to Intermediates 10-7 by alkylation with dihalide 10-6 in the presence of a base, such as sodium hydride, NaHMDS, KHMDS or lithium diisopropylamide.

Scheme 10

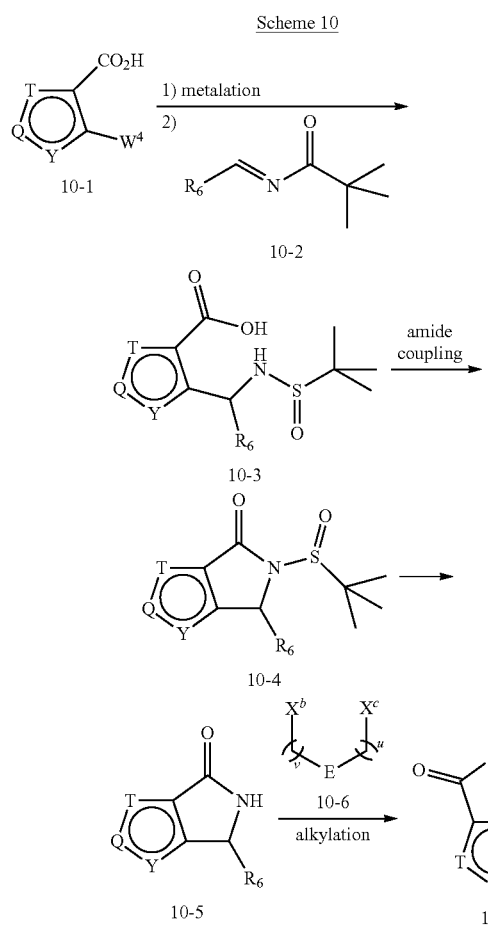

Intermediates 11-8 can be prepared as the methods described in Scheme 11. Esterification of carboxylate acids 11-1 ($W^4$ is H, Br, or I) with a suitable alcohol such as MeOH or EtOH can afford the corresponding thiophene esters 11-2. Lithiation of the acids 11-2 with a strong base, such as butyllithium, and subsequent addition into a formyl transfer reagent such as N,N-dimethylformamide, N-methoxy-N-methylformamide or N-formylmorpholine can afford aldehydes 11-3 which can be directly converted to lactams 11-4 by reaction with an amine $PG-NH_2$ (e.g., $PGNH_2$ is 4-methoxybenzylamine ($PMBNH_2$), 2,4-dimethoxybenzylamine ($DMB-NH_2$) or benzylamine ($Bn-NH_2$)) under reductive amination conditions (e.g., $NaBH(OAc)_3$ in DCM or DCE, optionally an acid such as acetic acid or TFA) and follow the ring closure under temperature enhancement. Removal of the protecting group in 11-4 can be achieved by treatment with acid such as TFA or by hydrogenation in the presence of a palladium catalyst such as Pd/C to afford Intermediates 11-5 which then can be converted to the Intermediates 11-8 by consequential alkylation with dihalides 11-7 and halide $R_6X$ in the presence of a base, such as NaH, NaHMDS, KHMDS or lithium diisopropylamide.

Alternatively, the lactams 11-4 can be prepared from amides 11-9. Amide coupling of thiophene acids 11-1 ($W^4$ is H, Br, or I) with a suitable amines $PGNH_2$ in the presence of a coupling reagent (e.g., N,N'-dicyclohexylcarbodiimide or HATU) and optionally an additive (e.g., 1-hydroxybenzotriazole or 4-dimethylaminopyridine) and optionally a base (e.g., pyridine or N,N-diisopropylethylamine) can provide amides 11-9 which can be converted to aldehydes 11-10 by the lithiation and the formyl transfer reagent as described above for formation of 11-3. Reduction of aldehydes 11-10 under standard conditions, such as in the presence of a reducing agent (e.g., sodium borohydride, lithium aluminumhydride, or borane tetrahydrofuran complex), can provide alcohols 11-11 which can be halogenated with suitable reagents, such as thionyl chloride or phosphorus tribromide or triphenylphosphine and iodine, to provide compounds 11-12 where $X^e$ is a halogen (e.g., Cl, Br, or I). Ring closure reaction of compounds 11-12 under basic conditions (e.g., in the presence of sodium hydride or lithium bis(trimethylsilyl)amide) can afford lactams 11-4.

Scheme 11

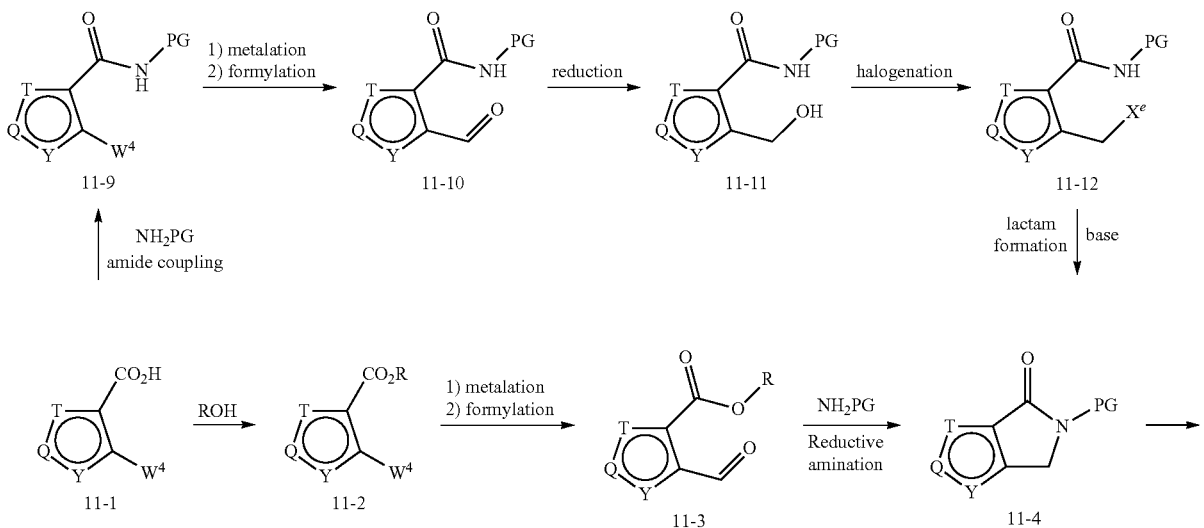

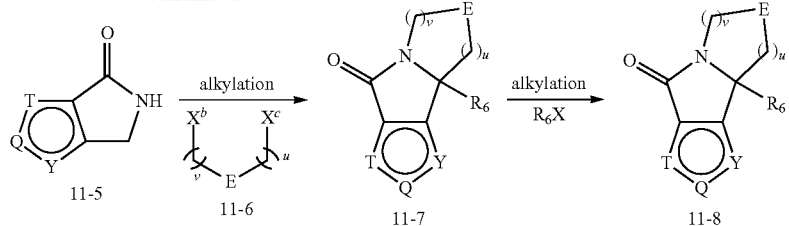

Alternatively, Intermediates 12-4 for the synthesis of compounds of Formula (I) can be prepared as the methods described in Scheme 12. Halogenation of carboxylates 12-1 with NBS, NCS or NIS under radical induced assistant conditions such as BPO [(PhCO$_2$)$_2$] or AIBN can afford halides 12-2 where X$^e$ is a halogen (e.g., Cl, Br, or I). The halides 12-2 can be directly converted to lactams 12-3 by reaction with an amine PGNH$_2$ (e.g., PGNH$_2$ is 4-methoxybenzylamine (PMBNH$_2$), 2,4-dimethoxybenzylamine (DMB-NH$_2$) or benzylamine (Bn-NH$_2$)) under reductive amination conditions (e.g., NaBH(OAc)$_3$ in DCM or DCE, optionally an acid such as acetic acid or TFA) and follow the ring closure under temperature enhancement. Removal of the protecting group in 12-3 can afford Intermediates 12-4 as description above Scheme 12

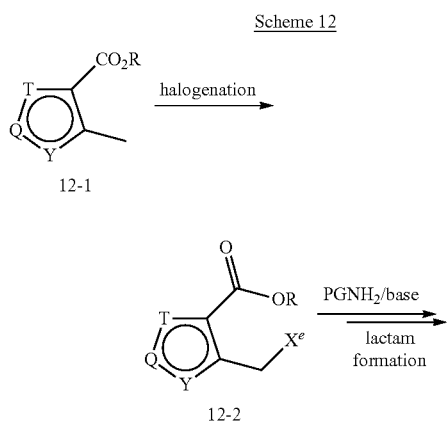

Intermediate aldehyde-carboxylate esters 13-3 can be prepared as the methods described in Scheme 13. Compounds 13-1 where W$^4$ is halogen (e.g., Cl, Br, or I) or pseudohalogen (e.g., OTf or OMs) can be converted to the corresponding vinyl derivatives 13-2 by reaction with vinyl boronic ester under standard Suzuki conditions (e.g., in the presence of a palladium catalyst, such as [1,1'-bis(diphenylphosphino)ferrocene]dichloro-palladium(II), and a base, such as K$_3$PO$_4$) or by reaction with vinyl tributyltin or vinyl zinc chloride under standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine) palladium(0) or [1,1'-bis(diphenylphosphino)ferrocene]dichloropalladium(II)). Oxidation of the vinyl in 13-2 either by ozonation or by reaction with NaIO$_4$/OsO$_4$ can give compounds 13-3.

Alternatively, compounds 13-1 can be converted to the corresponding cyano-derivatives 13-4. The cyano group in 13-4 then can be reduced to the aldehyde in 13-3 either by hydrogenation in the presence of a Ni catalyst or by reductive reagent such as AlH(Bu-i)$_2$ or SnCl$_2$.

Scheme 13

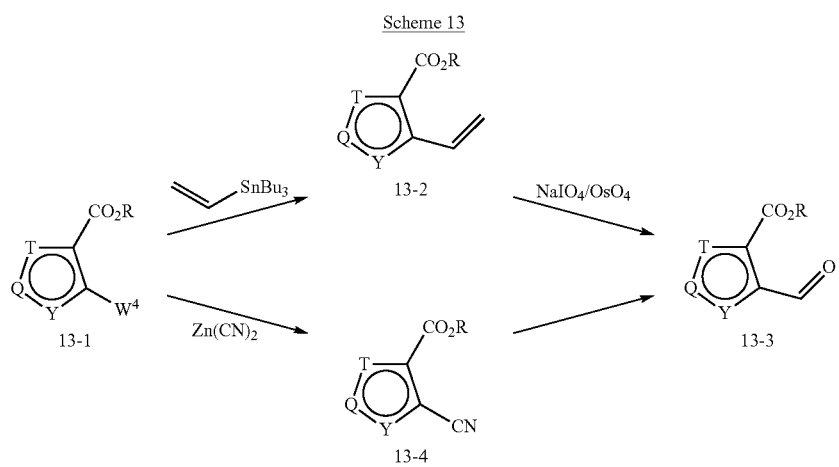

Intermediates 14-4, 14-5 and 14-6 for the synthesis of compounds of Formula (II) can be prepared as the methods described in Scheme 14. Alkylation of lactams 14-1 with dihalides 14-2, in the presence of a base, such as NaH, NaHMDS, KHMDS or lithium diisopropylamide (LDA), can provide intermediates 14-3. Further alkylation of 14-3 under same reaction conditions with $R_6X$ can afford Intermediates 14-4. Treatment of Intermediates 14-3 with strong base such as LDA or LiHMDS follows reaction with aldehydes $R_{6a}$CHO can yield Intermediates 14-5 which can be converted to the corresponding amine derivatives by treatment with MsCl or TfCl in the presence of a base such as Hunig's base and then with an amine $R_{6b}R_{6c}$NH to provide Intermediates 14-6.

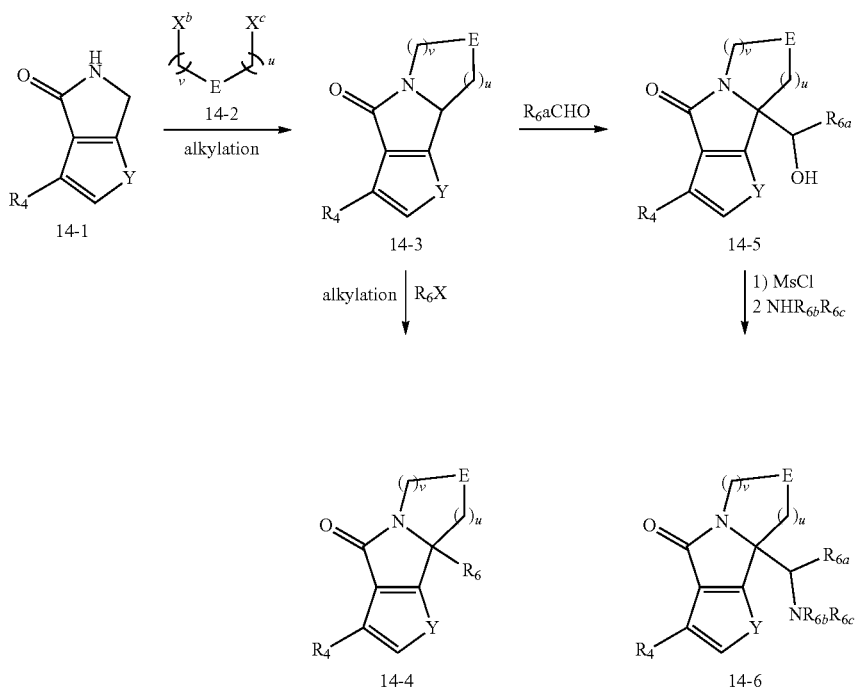

Intermediates 15-8 for the synthesis of compounds of Formula (III) can be prepared as the methods described in Scheme 15. Esterification of thiophene acid 15-1 with a suitable alcohol such as MeOH or EtOH can afford the corresponding thiophene ester 15-2. Lithiation of thiophenes 15-2 with a strong base, such as butyllithium, and subsequent addition into a formyl transfer reagent such as N,N-dimethylformamide, N-methoxy-N-methylformamide or N-formylmorpholine can afford aldehydes 15-3 which can be directly converted to lactams 15-4 by reaction with an amine $PGNH_2$ (e.g., $PGNH_2$ is 4-methoxybenzylamine ($PMBNH_2$), 2,4-dimethoxybenzylamine ($DMB-NH_2$) or benzylamine ($Bn-NH_2$)) under reductive amination conditions (e.g., $NaBH(OAc)_3$ in DCM or DCE, optionally an acid such as acetic acid or TFA). Removal of the protecting group in 15-4 as description in Scheme 11 can afford intermediates 15-5 which can be converted to intermediates 15-8 by consequential alkylation with dihalides 15-6 and $R_6X$ in the presence of a base, such as sodium hydride or lithium diisopropylamide as description in Scheme 11.

Alternatively, the lactams 15-4 can be prepared from amides 15-9. Amide coupling of thiophene acid 15-1 with a suitable amines PGNH$_2$ in the presence of a coupling reagent (e.g., N,N'-dicyclohexylcarbodiimide or HATU) and optionally an additive (e.g., 1-hydroxybenzotriazole or 4-dimethylaminopyridine) and optionally a base (e.g., pyridine or N,N-diisopropylethylamine) can provide amides 15-9. Lithiation of thiophene amides 15-9 with a strong base, such as butyllithium, and subsequent addition into a formyl transfer reagent such as N,N-dimethylformamide, N-methoxy-N-methylformamide or N-formylmorpholine can afford aldehydes 15-10. Reduction of aldehydes 15-10 under standard conditions, such as in the presence of a reducing agent (e.g., sodium borohydride, lithium aluminumhydride, or borane tetrahydrofuran complex), can provide alcohols 15-11 which can be halogenated with suitable reagents, such as thionyl chloride or phosphorus tribromide or triphenylphosphine and iodine, to provide compounds 15-12 where $X^e$ is a halogen (e.g., Cl, Br, or I). Ring closure reaction of compound 15-12 under basic conditions (e.g., in the presence of sodium hydride or lithium bis(trimethylsilyl)amide) can afford lactams 15-4.

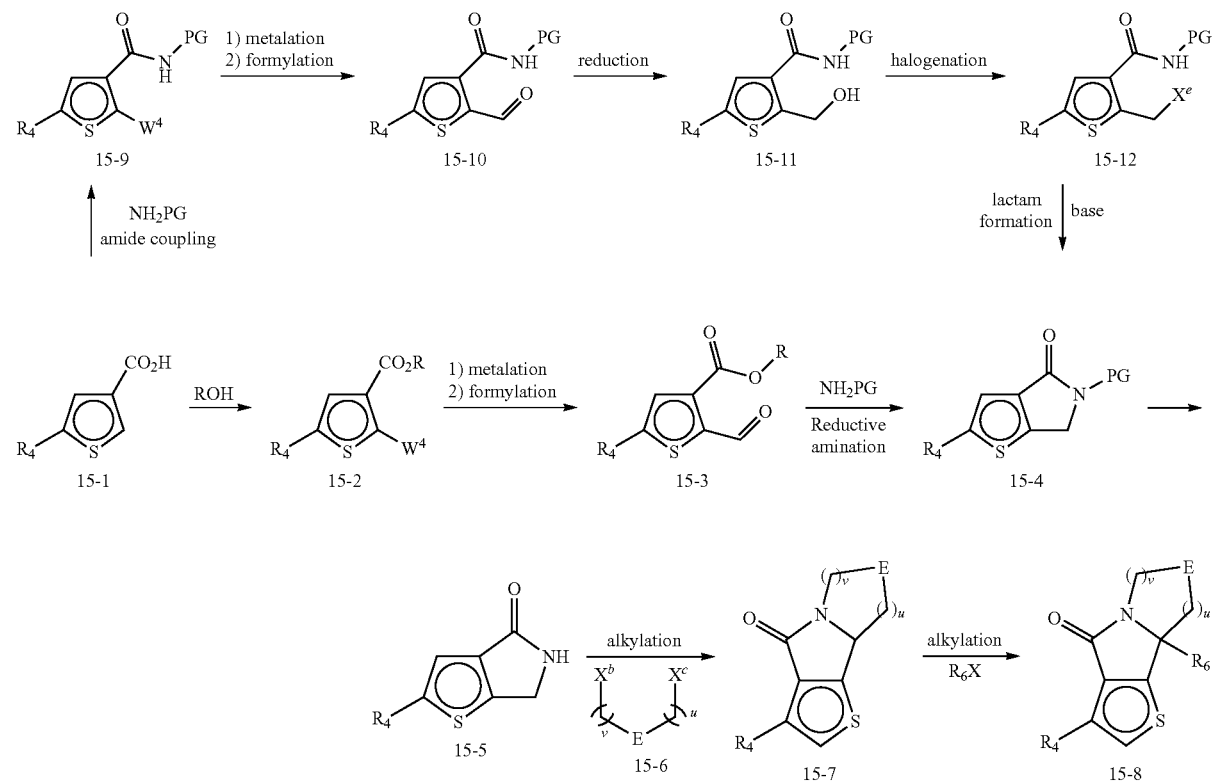

Scheme 15

Intermediates 16-10 and 16-11 for the synthesis of compounds of Formula (II) can be prepared as the methods described in Scheme 16. Claisen condensation of tert-butyl acetate 16-1 with an acid 16-2 can be achieved by treatment with LDA at low temperature to afford beta-keto ester 16-3. Mannish type reaction of 16-3 with 2-chloroacetaldehyde can directly provide 16-4 which can be further protected by treatment with TsCl in the presence of a base such as NatOBu to afford 16-5. Removal of the tert-Butyl and Boc-groups in 16-5 can be achieved under acid conditions, such as TFA/DCM, HCl in dioxane etc., to produce amino acid 16-6. Ring closure of 16-6 under amide coupling conditions can provide the lactam 16-7 which can be converted to Intermediates 16-10 and 16-11 by alkylation, deprotection and alkylation with $R_5X$ in the presence of a base as described previous Schemes.

Scheme 16

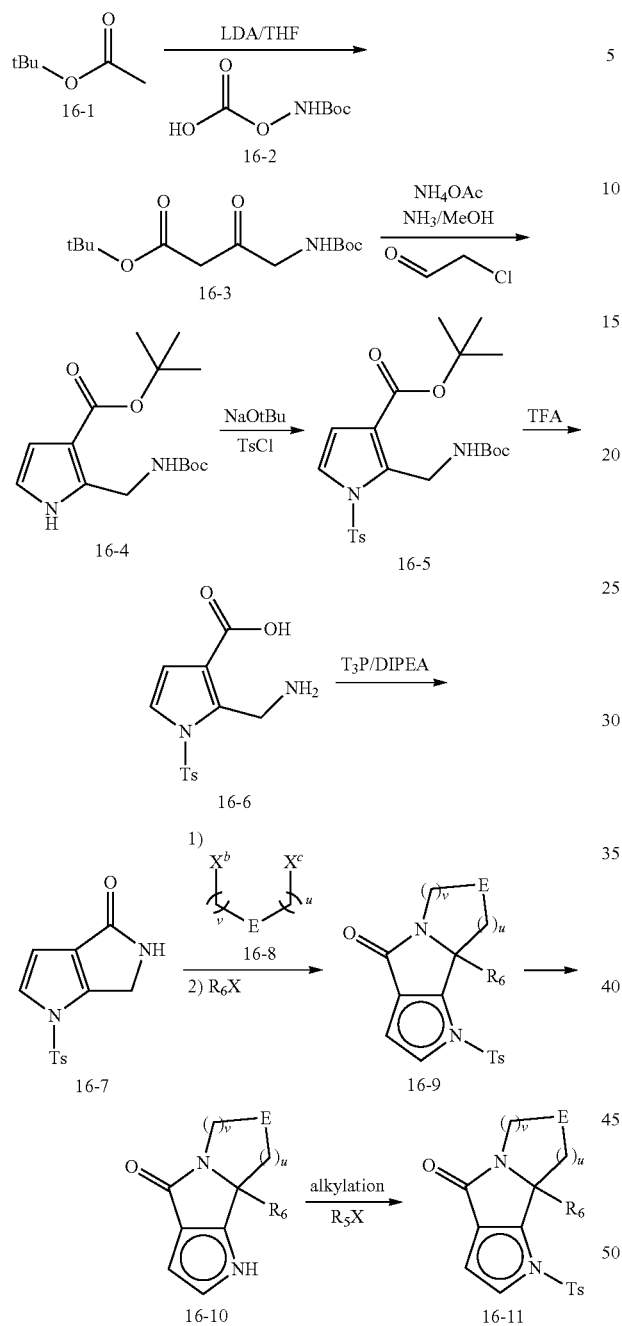

Scheme 17

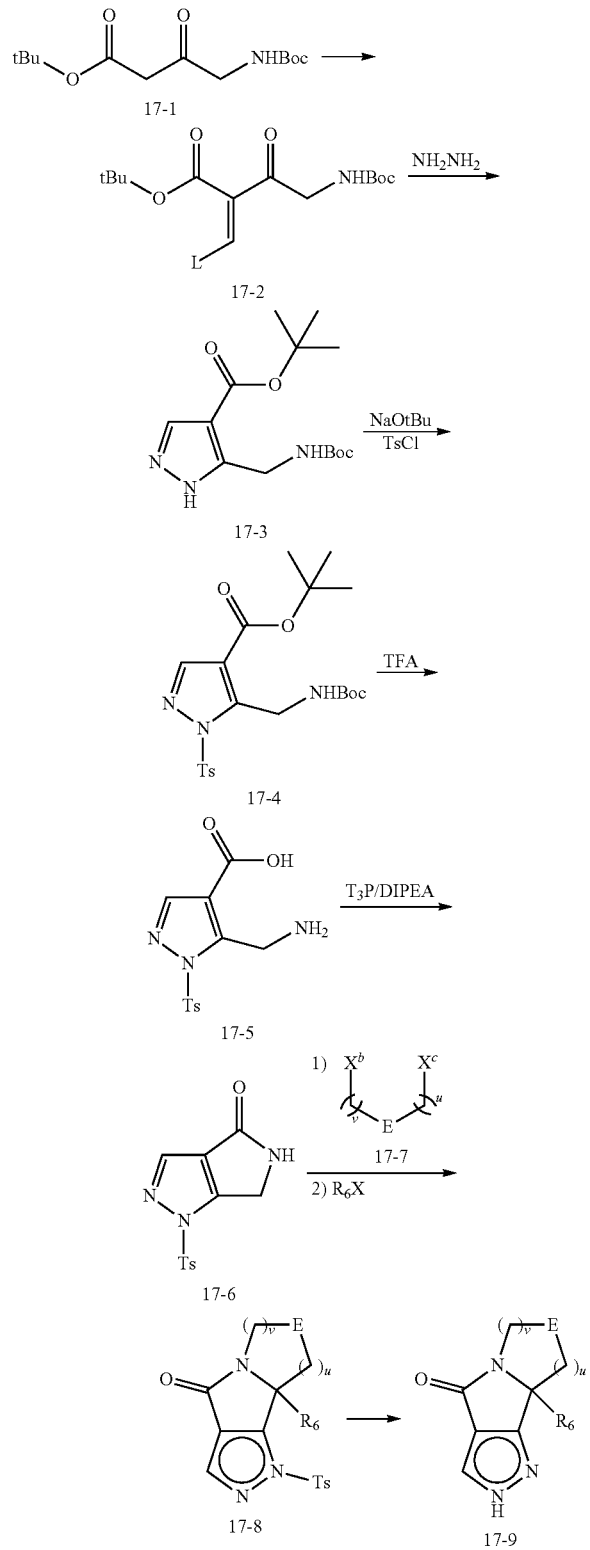

Intermediate 17-9 for the synthesis of compounds of Formula (I) can be prepared as the methods described in Scheme 17. Treatment of the beta-keto ester 17-1 with trialkyl orthoformate, such as trimethyl orthoformate or triethyl orthoformate, or with N,N-dimethylformamide dimethyl acetal or N,N-dimethylformamide diethyl acetal, can afford compound 17-2 where L=OMe, OEt, or $NMe_2$. 17-2 can react with hydrazine to provide pyrazole 17-3 which then can be converted to the Lactam 17-6 as the above described for the conversion of 16-4 to 16-7 in Scheme 16. Lactam 17-6 can be converted to the Intermediate 17-9 by alkylation and deprotection as described previous Schemes.

Intermediates 18-3 for the synthesis of compounds of Formula (I) can be prepared as the methods described in Scheme 18. Commercially available lactam 18-1 can react with trimethyl orthoformate, triethyl orthoformate, N,N- dimethylformamide dimethyl acetal or N,N-dimethylformamide diethyl acetal to provide compound 18-2 where L=OMe, OEt, or NMe$_2$. Reaction of 18-2 with 4-methylbenzenesulfonohydrazide can yield pyrazole 18-3.

Scheme 18

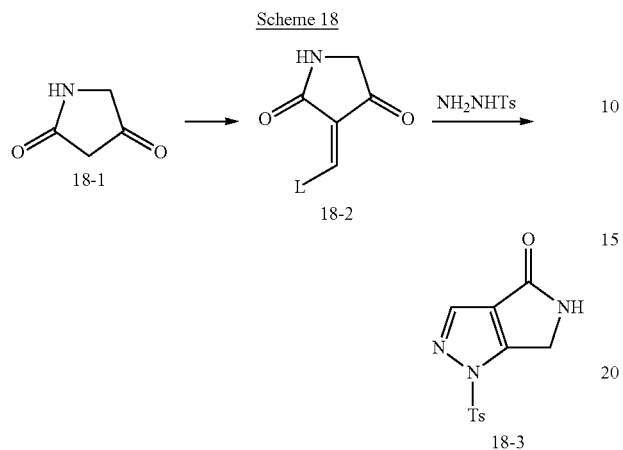

Intermediate 19-10 for the synthesis of compounds of Formula (I) can be prepared as the methods described in Scheme 19. Condensation of alpha-keto esters 19-1 with hydrazinecarboxamide can produce adducts 19-2 which can be directly converted to 4-formaldehydepyrazole-2-carboxylate esters 19-3 by Vilsmeier-Haack reaction with POCl$_3$ and DMF. Protecting of 19-3 by using protecting reagent, such as TsCl, CBzCl or (Boc)$_2$O in the presence of a base such as potassium carbonate, sodium carbonate, DIPEA, triethylamine etc., can provide 19-4 which then can be converted to 19-5 and 19-6 as previously descriptions in Schemes 11 and 15. 19-6 can be further converted to 19-10 by deprotection, alkylation and deprotection as descriptions in previous Schemes.

Scheme 19

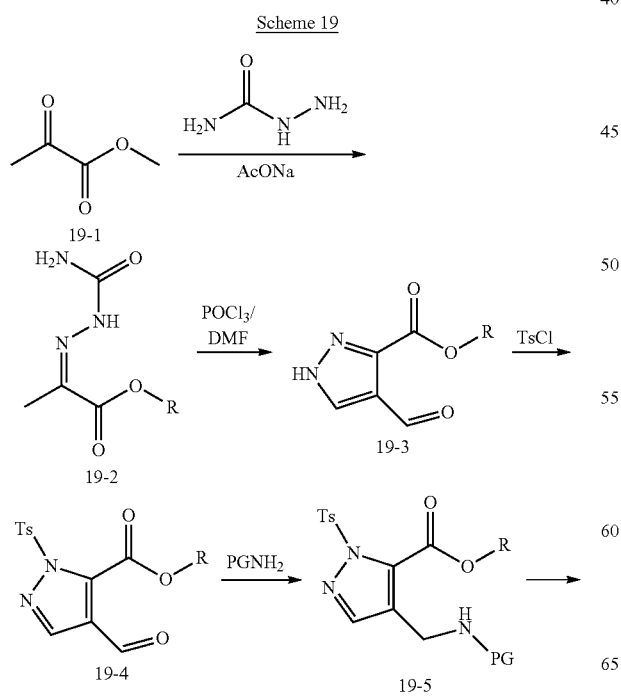

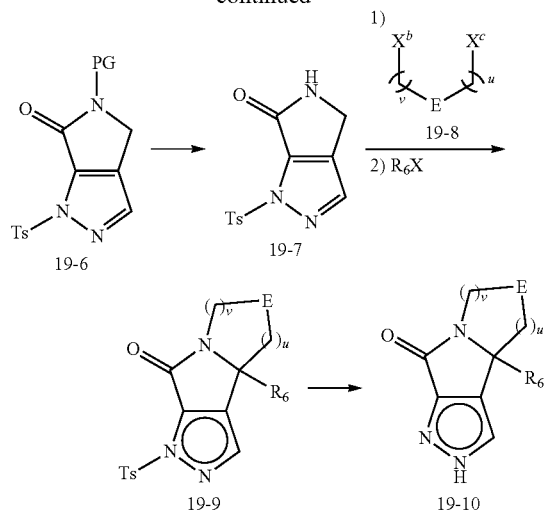

Example 1. 9a-isopropyl-2-(2-((1-(methylsulfonyl)piperidin-4-yl)amino)-5-(trifluoromethyl) pyrimidin-4-yl)-7,8,9,9a-tetrahydrothieno[2,3-a]indolizin-4(6H)-one

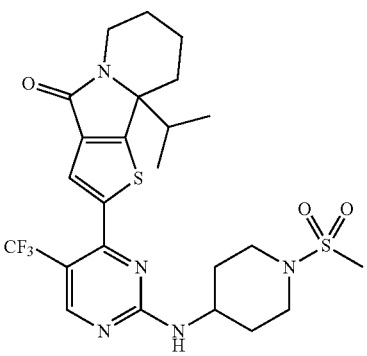 [SMILES: CC(C)C12CCCCN1C(=O)c1cc(-c3nc(NC4CCN(S(C)(=O)=O)CC4)ncc3C(F)(F)F)sc12]

Step 1. (R,E)-2-Methyl-N-(2-methylpropylidene)propane-2-sulfinamide

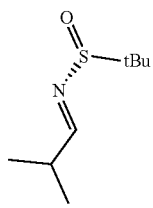

Isobutyraldehyde (0.913 mL, 10.0 mmol) was added to a stirring mixture of (R)-tert-butanesulfinamide (1.21 g, 10.0 mmol), pyridinium p-toluenesulfonate (251 mg, 1.0 mmol) and MgSO$_4$ (6.02 g, 50.0 mmol) in anhydrous DCM (20 mL) at r.t. The reaction mixture was stirred at r.t. overnight, filtered through a pad of Celite® and concentrated. The crude residue was purified by flash chromatography on a silica gel column eluting with EtOAc/heptanes (0-20%) to afford the title compound (1.26 g, 7.19 mmol, 71.9% yield). LCMS calc. for $C_8H_{18}NOS$ [M+H]$^+$: m/z=176.1; Found: 176.0.

Step 2. 2-(1-(((R)-tert-Butylsulfinyl)amino)-2-methylpropyl)thiophene-3-carboxylic Acid

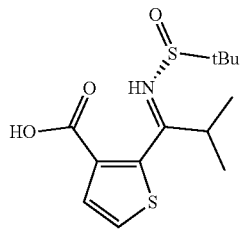

Lithium diisopropylamide (12.6 mL, 12.6 mmol, 1.0 M in THF) was added slowly to a solution of thiophene-3-carboxylic acid (0.77 g, 3.62 mmol) in THF (20 mL) at −60° C. and stirred for 30 min. A solution of (R,E)-2-methyl-N-(2-methylpropylidene)propane-2-sulfinamide (1.26 g, 7.19 mmol) in THF (10 mL) was added slowly to the reaction over 1 h at −60° C. The reaction mixture was allowed to warm to r.t. and stirred for additional 1 h. The reaction mixture was poured into water (100 mL), and extracted with EtOAc (100 mL). The aqueous layer was collected and acidified to pH ~3 using HCl (1 M, aq.), and extracted with EtOAc (100 mL×2). The combined organics were washed with brine, dried over $Na_2SO_4$, filtered, and concentrated to afford the title compound which was used directly in next step without further purification. LCMS calc. for $C_{13}H_{22}NO_3S_2$ [M+H]$^+$: m/z=304.1; Found: 304.0.

Step 3. 2-(1-Amino-2-methylpropyl)thiophene-3-carboxylic Acid

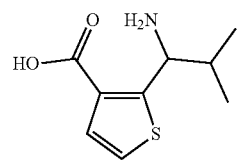

To a solution of 2-(1-(((R)-tert-Butylsulfinyl)amino)-2-methylpropyl)thiophene-3-carboxylic acid (from Step 2) in EtOAc (40 mL) was added conc. HCl (0.93 mL, 11.2 mmol) (12 M, aq.). The reaction mixture was stirred at r.t. for 30 min. The white precipitate formed was collected by filtration and washed with EtOAc. The white solid was dried to afford the title compound (1.50 g, 6.36 mmol, 63.6% yield over two steps) as its HCl salt. LCMS calc. for $C_9H_{14}NO_2S$ [M+H]$^+$: m/z=200.1; Found: 200.0.

Step 4. 6-Isopropyl-5,6-dihydro-4H-thieno[2,3-c]pyrrol-4-one

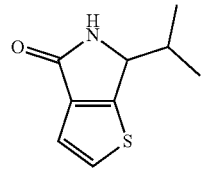

To a solution of 2-(1-Amino-2-methylpropyl)thiophene-3-carboxylic acid hydrochloride salt (400 mg, 1.70 mmol) in DCM (80 mL) was added HATU (968 mg, 2.55 mmol) and triethylamine (0.71 mL, 5.09 mmol). The reaction mixture was stirred at r.t. for 1 h before quenched with water (100 mL). The layers were separated, and the organic layer was washed with brine, dried over $Na_2SO_4$, filtered and concentrated. The crude residue was purified by flash chromatography on a silica gel column eluting with (EtOAc/Hexanes 0-60%) to afford the title compound (290 mg, 1.60 mmol, 94.3% yield). LCMS calc. for $C_9H_{12}NOS$ [M+H]$^+$: m/z=182.1; Found: 182.0.

Step 5. 9a-Isopropyl-7,8,9,9a-tetrahydrothieno[2,3-a]indolizin-4(6H)-one

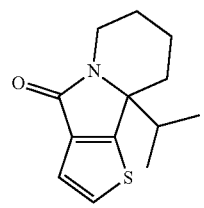 [SMILES: CC(C)C12CCCCN1C(=O)c1ccsc12]

A mixture of 6-isopropyl-5,6-dihydro-4H-thieno[2,3-c]pyrrol-4-one (120 mg, 0.662 mmol) and NaH (79.4 mg, 1.99 mmol, 60% suspension in mineral oil) in a degassed anhydrous DMF (6.6 mL) was stirred at r.t. for 10 min under a nitrogen atmosphere. Then 1,4-diiodobutane (0.105 mL, 0.794 mmol) was added. The reaction mixture was stirred at r.t. for 3 h., quenched with sat. $NH_4Cl$ (aq.), and extracted with EtOAc (25 mL×2). The combined organics were washed with brine, dried over $Na_2SO_4$, filtered, and concentrated. The crude residue was purified by flash chromatography on a silica gel column eluting with EtOAc/heptanes (0-30%) to afford the title compound (55.0 mg, 0.234 mmol, 35.3% yield). LCMS calc. for $C_{13}H_{18}NOS$ [M+H]$^+$: m/z=236.1; Found: 236.0.

Step 6. 2-Bromo-9a-isopropyl-7,8,9,9a-tetrahydrothieno[2,3-a]indolizin-4(6H)-one

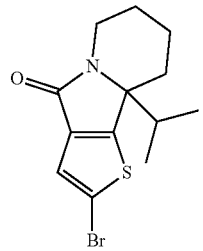 [SMILES: CC(C)C12CCCCN1C(=O)c1cc(Br)sc12]

N-Bromosuccinimide (41.6 mg, 0.23 mmol) was added to a solution of 9a-isopropyl-7,8,9,9a-tetrahydrothieno[2,3-a]indolizin-4(6H)-one (55.0 mg, 0.23 mmol) in acetonitrile (2.3 mL) at r.t. and stirred overnight. The mixture was concentrated. The crude residue was purified by flash chromatography on a silica gel column eluting with EtOAc/heptanes (0-20%) to afford the title compound (70.0 mg, 0.223 mmol, 95.3% yield). $^1$H NMR (600 MHz, CDCl$_3$) δ 7.29 (s, 1H), 4.33 (ddd, J=13.5, 5.5, 1.6 Hz, 1H), 2.81 (td, J=13.3, 3.3 Hz, 1H), 2.47 (hept, J=6.8 Hz, 1H), 2.39-2.30 (m, 1H), 1.78-1.65 (m, 3H), 1.41-1.31 (m, 1H), 1.31-1.20 (m, 1H), 1.12 (d, J=6.8 Hz, 3H), 0.48 (d, J=6.7 Hz, 3H). $^{13}$C NMR (150 MHz, CDCl$_3$) δ 162.20, 156.51, 139.30, 123.29, 115.18, 69.15, 37.24, 34.70, 29.84, 27.33, 25.57, 19.61, 17.49, 15.65. LCMS calc. for C$_{13}$H$_{17}$BrNOS [M+H]$^+$: m/z=314.0, 316.0; Found: 313.9, 315.9.

Step 7. 4-chloro-N-(1-(methylsulfonyl)piperidin-4-yl)-5-(trifluoromethyl)pyrimidin-2-amine

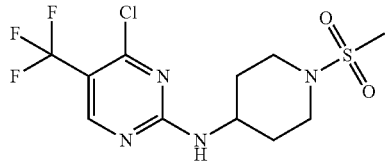 [SMILES: CS(=O)(=O)N1CCC(Nc2ncc(C(F)(F)F)c(Cl)n2)CC1]

Zinc chloride solution (69.1 mL, 1.0 M, 69.1 mmol) in diethyl ether was added to a cooled (with an ice bath) mixture of 2,4-dichloro-5-(trifluoromethyl)pyrimidine (10.0 g, 46.1 mmol) in tert-butanol (100 mL) and DCE (100 mL) under nitrogen. The resulting mixture was stirred at 0° C. for 1 h. Then 1-methylsulfonylpiperidin-4-amine; trifluoroacetic acid (12.8 g, 43.8 mmol) was added and followed by dropwise addition of TEA (9.64 mL, 69.1 mmol). The ice bath was then removed. The reaction mixture was allowed to warm to r.t. heated at 60° C. overnight. After cooling to r.t., the reaction mixture was concentrated. The residue was purified by flash chromatography on a silica gel column eluting with EtOAc/heptanes (0-50%). The desired fractions were collected and concentrated, and further purified by prep HPLC eluting with ACN/H$_2$O (10% to 80% including 0.1% TFA) to afford the title compound (5.1 g) as white solid. LCMS calc. for C$_{11}$H$_{15}$ClF$_3$N$_4$O$_2$S [M+H]$^+$: m/z=359.1; Found: 358.8. $^1$H NMR (300 MHz, Chloroform-d) δ 8.45 (s, 1H), 5.54 (s, 1H), 4.11-3.95 (m, 1H), 3.79 (d, J=11.2 Hz, 2H), 2.97-2.85 (m, 2H), 2.82 (s, 3H), 2.16 (d, J=10.9 Hz, 2H), 1.71-1.62 (m, 3H).

Step 8. 9a-Isopropyl-2-(2-((1-(methylsulfonyl)piperidin-4-yl)amino)-5-(trifluoromethyl) pyrimidin-4-yl)-7,8,9,9a-tetrahydrothieno[2,3-a]indolizin-4(6H)-one A solution of 2-bromo-9a-isopropyl-7,8,9,9a-tetrahydrothieno[2,3-a]indolizin-4(6H)-one (32.0 mg, 0.10 mmol), hexamethylditin (0.042 mL, 0.20 mmol) and tetrakis(triphenylphosphine)palladium(0) (11.8 mg, 0.010 mmol) in 1,4-dioxane (3.4 mL) was heated at 100° C. under a nitrogen atmosphere for 1 h. The reaction mixture was cooled to r.t., and 4-chloro-N-(1-(methylsulfonyl)piperidin-4-yl)-5-(trifluoromethyl)pyrimidin-2-amine (36.5 mg, 0.10 mmol) was added. The reaction mixture was stirred at 100° C. overnight. After the reaction mixture cooled to r.t., a solution of potassium fluoride (23.7 mg, 0.41 mmol) in water (2 mL) was added. The reaction mixture was stirred for 10 min and filtered. The filtrate was purified by prep-HPLC on a C18 column (45-65% MeCN in 0.1% TFA (aq.), pH=2) to afford the title compound (32.0 mg, 0.0476 mmol, 46.8%) as its TFA salt. LCMS calc. for C$_{24}$H$_{31}$F$_3$N$_5$O$_3$S$_2$ [M+H]$^+$: m/z=558.2; Found: 558.0.

Example 2 and Example 3. (9aS)-9a-Isopropyl-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one and (9aR) 9a-Isopropyl-2-(2-((1-(methylsulfonyl)piperidin-4-yl)amino)-5-(trifluoromethyl) pyrimidin-4-yl)-7,8,9, 9a-tetrahydrothieno[2,3-a]indolizin-4(6H)-one

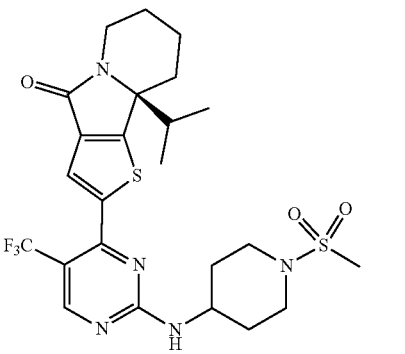

Example 2 or Example 3

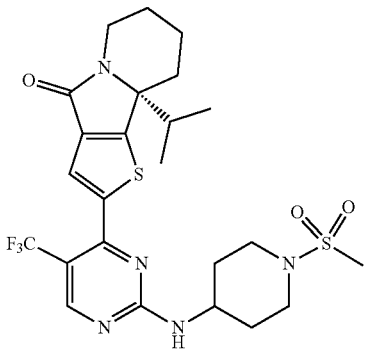

Example 3 or Example 2

The racemic material of 9a-isopropyl-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one (Example 6) was purified by chiral-HPLC Column under Chiral HPLC separation conditions: Phenomenex Lux Cellulose-1, 5 micron, 250×21.2 mm; Mobile Phase: 9:1 Hexanes:Ethanol (denatured w/ 5% ea. MeOH and IPA); Composition/Flow: 30.0 mL/min. The peaks were analyzed by chiral-HPLC. Column: Phenomenex Lux Cellulose-4, 5 micron, 100×4.6 mm; Mobile Phase: A=Hexanes, B=Ethanol (denatured as above); Composition/Flow: 1.0 mL/min, 2-90% B over 5 min, hold 2.75 min (gradient run); Peak 1 (ee: 100%, retention time: $R_t$=6.22 min) was assigned to Example 2 or Example 3, LCMS calc. for $C_{24}H_{31}F_3N_5O_3S_2$ [M+H]$^+$: m/z=558.2; Found: 558.0. and Peak 2 (95%, retention time: $R_t$=6.74 min) was assigned to Example 3 or Example 2, LCMS calc. for $C_{24}H_{31}F_3N_5O_3S_2$ [M+H]$^+$: m/z=558.2; Found: 558.0.

Example 4. 9a-(3-Hydroxypropyl)-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one

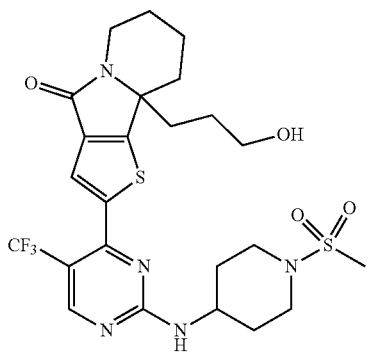 [SMILES: CS(=O)(=O)N1CCC(Nc2ncc(C(F)(F)F)c(-c3cc4c(s3)C3(CCCO)CCCCN3C4=O)n2)CC1]

Step 1. 7,8,9,9a-Tetrahydrothieno[2,3-a]indolizin-4(6H)-one

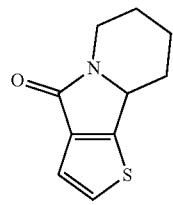 [SMILES: O=C1c2ccsc2C2CCCCN12]

To a mixture of 5,6-dihydro-4H-thieno[2,3-c]pyrrol-4-one (100 mg, 0.72 mmol) and NaH (115 mg, 2.87 mmol, 60% suspension in mineral oil) in a degassed anhydrous DMF (6.0 mL) was stirred at r.t. for 10 min. under a nitrogen atmosphere. Then 1,4-diiodobutane (0.11 mL, 0.86 mmol) was added. The reaction mixture was stirred at r.t. for 3 h., quenched with sat. NH$_4$Cl (aq.), and extracted with EtOAc (25 mL×2). The combined organics were washed with brine, dried over Na$_2$SO$_4$, filtered, and concentrated. The crude residue was purified by flash chromatography on a silica gel column eluting with (0-30% EtOAc/heptanes) to afford the title compound (20.0 mg, 0.10 mmol, 14.4% yield). LCMS calc. for $C_{10}H_{12}NOS$ [M+H]$^+$: m/z=194.1; Found: 194.0.

Step 2. 9a-(3-(Benzyloxy)propyl)-7,8,9,9a-tetrahydrothieno[2,3-a]indolizin-4(6H)-one

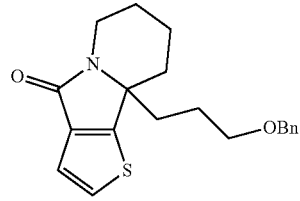 [SMILES: O=C1c2ccsc2C2(CCCOCc3ccccc3)CCCCN12]

To a vial containing 7,8,9,9a-tetrahydrothieno[2,3-a]indolizin-4(6H)-one (20.0 mg, 0.10 mmol) and NaH (12.4 mg, 0.31 mmol, 60% suspension in mineral oil) was added degassed anhydrous DMF (1.0 mL) and stirred at r.t. for 10 min under a nitrogen atmosphere. Next benzyl 3-bromopropyl ether (0.037 mL, 0.21 mmol) was added and the reaction mixture was stirred at r.t. overnight. The reaction was quenched with sat. NH$_4$Cl (aq.). The reaction mixture was extracted with EtOAc (5 mL×2). The combined organics were washed with brine, dried over Na$_2$SO$_4$, filtered, and concentrated. The crude residue was purified by flash chromatography on a silica gel column eluting with EtOAc/heptanes (0-30%) to afford the title compound (26.0 mg, 0.076 mmol, 73.6% yield). LCMS calc. for $C_{20}H_{24}NO_2S$ [M+H]$^+$: m/z=342.2; Found: 342.0.

Step 3. 9a-(3-(Benzyloxy)propyl)-2-bromo-7,8,9,9a-tetrahydrothieno[2,3-a]indolizin-4(6H)-one

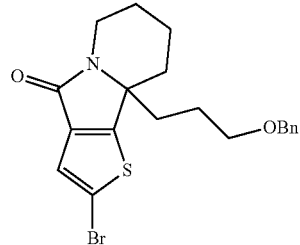 [SMILES: O=C1c2cc(Br)sc2C2(CCCOCc3ccccc3)CCCCN12]

This compound was prepared using procedures analogous to those described for Example 1 Step 6 using 9a-methyl-7,8,9,9a-tetrahydrothieno[2,3-a]indolizin-4(6H)-one to afford the title compound. LCMS calc. for $C_{20}H_{23}BrNO_2S$ [M+H]$^+$: m/z=420.1, 422.1; Found: 419.9, 421.9.

Step 4. 2-Bromo-9a-(3-hydroxypropyl)-7,8,9,9a-tetrahydrothieno[2,3-a]indolizin-4(6H)-one

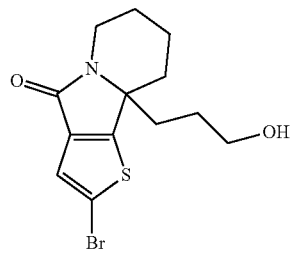 [SMILES: O=C1c2cc(Br)sc2C2(CCCO)CCCCN12]

To a solution of 9a-(3-(benzyloxy)propyl)-2-bromo-7,8,9,9a-tetrahydrothieno[2,3-a]indolizin-4(6H)-one (20.0 mg, 0.048 mmol) in DCM (2.0 mL) at −78° C. was added boron tribromide (0.14 mL, 0.14 mmol) (1.0 M in DCM). The reaction mixture was stirred at r.t. for 30 min before quenched with sat. NaHCO₃ (aq.). The reaction mixture was extracted with EtOAc (10 mL), washed with brine, dried over Na₂SO₄, filtered, and concentrated. The crude residue was purified by flash chromatography on a silica gel column eluting with EtOAc/Hexanes (0-100%) to afford the title compound (15.2 mg, 0.046 mmol, 96.7% yield). LCMS calc. for $C_{13}H_{17}BrNO_2S$ [M+H]⁺: m/z=330.0, 332.0; Found: 329.9, 331.9.

Step 5. 9a-(3-Hydroxypropyl)-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one This compound was prepared using procedures analogous to those described for Example 1 Step 8 using 2-bromo-9a-(3-hydroxypropyl)-7,8,9,9a-tetrahydrothieno[2,3-a]indolizin-4(6H)-one and 4-chloro-N-(1-(methylsulfonyl)piperidin-4-yl)-5-(trifluoromethyl)pyrimidin-2-amine to afford the title compound as its TFA salt. LCMS calc. for $C_{24}H_{31}F_3N_5O_4S_2$ [M+H]⁺: m/z=574.2; Found: 573.9.

Example 5. 9a-(2-Hydroxyethyl)-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one

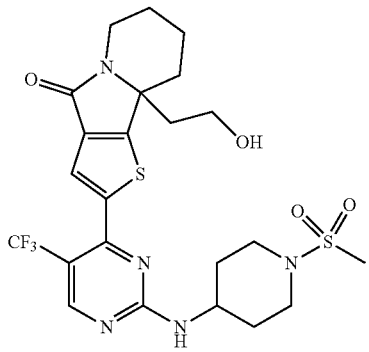 [SMILES: CS(=O)(=O)N1CCC(Nc2ncc(C(F)(F)F)c(-c3cc4c(s3)C3(CCO)CCCCN3C4=O)n2)CC1]

Step 1. 9a-(2-((Tetrahydro-2H-pyran-2-yl)oxy)ethyl)-7,8,9,9a-tetrahydrothieno[2,3-a]indolizin-4(6H)-one

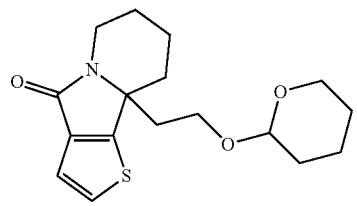 [SMILES: O=C1c2ccsc2C2(CCOC3CCCCO3)CCCCN12]

This compound was prepared using procedures analogous to those described for Example 4 Step 2 using 2-(2-bromoethoxy)tetrahydro-2H-pyran to replace benzyl 3-bromopropyl ether to afford the title compound (33.0 mg, 0.10 mmol, 73.5% yield). LCMS calc. for $C_{17}H_{24}NO_3S$ [M+H]⁺: m/z=322.2; Found: 322.1.

Step 2. 2-Bromo-9a-(2-((tetrahydro-2H-pyran-2-yl)oxy)ethyl)-7,8,9,9a-tetrahydrothieno[2,3-a]indolizin-4(6H)-one

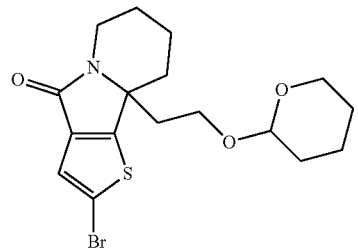 [SMILES: O=C1c2cc(Br)sc2C2(CCOC3CCCCO3)CCCCN12]

This compound was prepared using procedures analogous to those described for Example 1 Step 6 using 9a-methyl-7,8,9,9a-tetrahydrothieno[2,3-a]indolizin-4(6H)-one to afford the title compound. LCMS calc. for $C_{17}H_{23}BrNO_3S$ [M+H]⁺: m/z=400.0, 402.0; Found: 399.9, 401.8.

Step 3. 2-Bromo-9a-(2-hydroxyethyl)-7,8,9,9a-tetrahydrothieno[2,3-a]indolizin-4(6H)-one

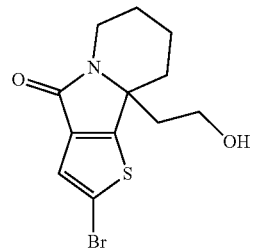 [SMILES: O=C1c2cc(Br)sc2C2(CCO)CCCCN12]

To a solution of 2-bromo-9a-(2-((tetrahydro-2H-pyran-2-yl)oxy)ethyl)-7,8,9,9a-tetrahydrothieno[2,3-a]indolizin-4(6H)-one (41.0 mg, 0.10 mmol) in MeOH (3.0 mL) was added conc. HCl (0.25 mL) (12 M, aq.). The reaction mixture was stirred at r.t. for 1 h before quenched with sat. NaHCO₃ (aq.). The reaction mixture was extracted with EtOAc (10 mL), washed with brine, dried over Na₂SO₄, filtered, and concentrated. The crude residue was purified by flash chromatography on a silica gel column eluting with EtOAc/Hexanes (0-100%) to afford the title compound (11.0 mg, 0.035 mmol, 34.0% yield). LCMS calc. for $C_{12}H_{15}BrNO_2S$ [M+H]⁺: m/z=316.0, 318.0; Found: 315.8, 317.9.

Step 4. 9a-(3-Hydroxyethyl)-2-(2-((1-(methylsulfonyl)piperidin-4-yl)amino)-5-(trifluoromethyl)pyrimidin-4-yl)-7,8,9,9a-tetrahydrothieno[2,3-a]indolizin-4(6H)-one This compound was prepared using procedures analogous to those described for Example 1 Step 8 using 2-bromo-9a-(3-hydroxyethyl)-7,8,9,9a-tetrahydrothieno[2,3-a]indolizin-4(6H)-one and 4-chloro-N-(1-(methylsulfonyl)piperidin-4-yl)-5-(trifluoromethyl)pyrimidin-2-amine to afford the title compound as its TFA salt. LCMS calc. for $C_{23}H_{29}F_3N_5O_4S_2$ [M+H]$^+$: m/z=560.2; Found: 560.0.

Example 6. 2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one

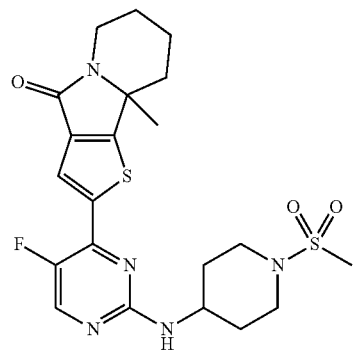 [SMILES: CC12CCCCN1C(=O)c1cc(-c3nc(NC4CCN(S(C)(=O)=O)CC4)ncc3F)sc12]

Step 1. 9a-methyl-7,8,9,9a-tetrahydrothieno[2,3-a]indolizin-4(6H)-one

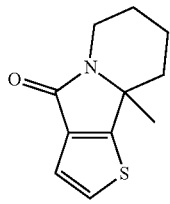

A mixture of 5,6-dihydro-4H-thieno[2,3-c]pyrrol-4-one (90.0 mg, 0.65 mmol) and NaH (104 mg, 2.59 mmol, 60% suspension in mineral oil) in a degassed anhydrous DMF (6.5 mL) was stirred at r.t. for 10 min. under a nitrogen atmosphere. Then 1,4-diiodobutane (0.10 mL, 0.78 mmol) was added and the reaction mixture was stirred at r.t. for 3 h. Additional NaH (51.5 mg, 1.29 mmol, 60% suspension in mineral oil) was added to the reaction, followed by addition of iodomethane (0.097 mL, 1.55 mmol). The reaction was stirred at r.t. overnight, quenched with sat. NH$_4$Cl (aq.) and extracted with EtOAc (25 mL×2). The combined organics were washed with brine, dried over Na$_2$SO$_4$, filtered, and concentrated. The crude residue was purified by flash chromatography on a silica gel eluting with EtOAc/heptanes (0-40%) to afford the title compound (64.0 mg, 0.31 mmol, 47.7% yield). LCMS calc. for $C_{11}H_{14}NOS$ [M+H]$^+$: m/z=208.1; Found: 208.0.

Step 2. 2-Bromo-9a-methyl-7,8,9,9a-tetrahydrothieno[2,3-a]indolizin-4(6H)-one

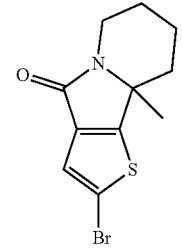

This compound was prepared using procedures analogous to those described for Example 1 Step 6 using 9a-methyl-7,8,9,9a-tetrahydrothieno[2,3-a]indolizin-4(6H)-one to afford the title compound. LCMS calc. for $C_{11}H_{13}BrNOS$ [M+H]$^+$: m/z=286.0, 288.0; Found: 285.8, 287.8.

Step 3. 2-(2-Chloro-5-fluoropyrimidin-4-yl)-9a-methyl-7,8,9,9a-tetrahydrothieno[2,3-a]indolizin-4(6H)-one

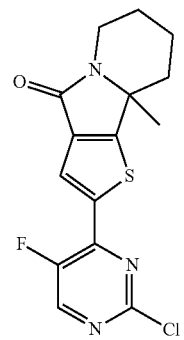 [SMILES: CC12CCCCN1C(=O)c1cc(-c3nc(Cl)ncc3F)sc12]

A solution of 2-bromo-9a-methyl-7,8,9,9a-tetrahydrothieno[2,3-a]indolizin-4(6H)-one (47.0 mg, 0.16 mmol), hexamethylditin (0.068 mL, 0.33 mmol) and tetrakis(triphenylphosphine) palladium(0) (19.5 mg, 0.017 mmol) in 1,4-dioxane (5.5 mL) was stirred at 100° C. under a nitrogen atmosphere for 1 h. The reaction mixture was cooled to r.t., and 2,6-dichloro-5-fluoroacil (68.6 mg, 0.41 mmol) was added. The reaction mixture was stirred at 100° C. overnight and then cooled to r.t. A solution of potassium fluoride (38.2 mg, 0.66 mmol) in water (5.0 mL) was added to the reaction mixture. The resulting mixture was stirred for 10 min. and extracted with EtOAc (15 mL). The organic layer was washed with brine, dried over Na$_2$SO$_4$, filtered, and concentrated. The crude residue was purified by flash chromatography on a silica gel eluting with EtOAc/heptanes (0-35%) to afford the title compound (50.0 mg, 0.15 mmol, 90.1% yield). LCMS calc. for $C_{15}H_{14}ClFN_3OS$ [M+H]$^+$: m/z=338.0, 340.0; Found: 338.0, 339.9.

Step 4. 2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one A solution of 2-(2-chloro-5-fluoropyrimidin-4-yl)-9a-methyl-7,8,9,9a-tetrahydrothieno[2,3-a]indolizin-4(6H)-one (22.0 mg, 0.065 mmol), 1-(methylsulfonyl)-4-piperidinamine (23.2 mg, 0.13 mmol) and N,N-diisopropylethylamine (0.045 mL, 0.26 mmol) in NMP (1.0 mL) was heated at 160° C. under a nitrogen atmosphere for 24 h. The reaction mixture was cooled to r.t., diluted with DMSO and purified by prep-HPLC on a C18 column (34.5-54.5% MeCN in 0.1% TFA (aq.), pH=2) to afford the title compound (16.9 mg, 0.028 mmol, 43.7%) as its TFA salt. $^1$H NMR (400 MHz, CD$_3$OD) δ 8.30 (d, J=3.5 Hz, 1H), 7.92 (d, J=1.5 Hz, 1H), 4.27 (dd, J=13.5, 4.9 Hz, 1H), 3.97-3.88 (m, 1H), 3.72 (d, J=12.2 Hz, 2H), 3.11-3.03 (m, 1H), 2.99 (t, J=10.6 Hz, 2H), 2.87 (s, 3H), 2.25 (d, J=13.1 Hz, 1H), 2.19-2.09 (m, 1H), 1.94-1.78 (m, 3H), 1.73-1.62 (m, 1H), 1.61 (s, 3H), 1.50-1.41 (m, 1H), 1.38-1.28 (m, 1H). LCMS calc. for C$_{21}$H$_{27}$FN$_5$O$_3$S$_2$ [M+H]$^+$: m/z=480.2; Found: 480.1.

Example 7 and Example 8. (9aS)-2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one and (9aR)-2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one Example 8 or Example 7

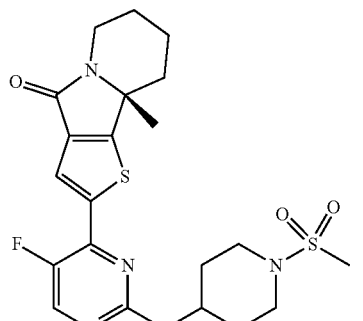

and

Example 7 or Example 8

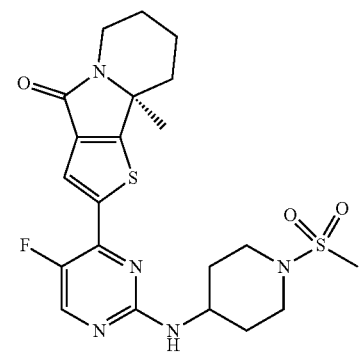

The racemic material of 2-(5-fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one (Example 1) was purified by chiral-HPLC under Chiral HPLC separation conditions: Column: Phenomenex Lux 5 micron Cellulose-1, 250×21.2 mm; Mobile Phase: 60:40 hexanes:EtOH (denatured w/ 5% IPA and 5% MeOH); Composition/Flow: 20 mL/min. The peaks were analyzed by chiral-HPLC. Method: Phenomenex Lux 5 micron Cellulose-1, 100×4.6 mm with hexanes:EtOH=80:20 (denatured) at Flow rate: 1.0 mL/min.

Peak 1 (ee: 100%, retention time: R$_t$=11.20 min) was assigned to Example 7 or Example 8. LCMS calc. for C$_{21}$H$_{27}$FN$_5$O$_3$S$_2$ [M+H]$^+$: m/z=480.2; Found: 480.0. And Peak 2 (ee: 94%, retention time: R$_t$=13.57 min) was assigned to Example 8 or Example 7. LCMS calc. for C$_{21}$H$_{27}$FN$_5$O$_3$S$_2$ [M+H]$^+$: m/z=480.2; Found: 480.0.

Example 9. 2-(5-Fluoro-2-((1-(methylsulfonyl)piperidin-4-yl)amino)pyrimidin-4-yl)-9a-isopropyl-7,8,9,9a-tetrahydrothieno[2,3-a]indolizin-4(6H)-one

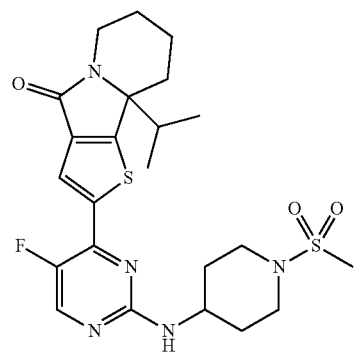 [SMILES: CC(C)C12CCCCN1C(=O)c1cc(-c3nc(NC4CCN(S(C)(=O)=O)CC4)ncc3F)sc12]

This compound was prepared using procedures analogous to those described for Example 6 Step 3 and 4 using 2-bromo-9a-isopropyl-7,8,9,9a-tetrahydrothieno[2,3-a]indolizin-4(6H)-one and 2,6-dichloro-5-fluororacil in Step 3 and 1-(methylsulfonyl)-4-piperidinamine in Step 4 to afford the title compound as its TFA salt. $^1$H NMR (400 MHz, CD$_3$OD) δ 8.31 (d, J=3.5 Hz, 1H), 7.97 (d, J=1.5 Hz, 1H), 4.28 (dd, J=13.7, 5.1 Hz, 1H), 3.99-3.86 (m, 1H), 3.76-3.66 (m, 2H), 3.06-2.93 (m, 3H), 2.87 (s, 3H), 2.69 (p, J=6.9 Hz, 1H), 2.55 (d, J=13.6 Hz, 1H), 2.20-2.08 (m, 2H), 1.93-1.63 (m, 5H), 1.45-1.28 (m, 2H), 1.25 (d, J=6.8 Hz, 3H), 0.49 (d, J=6.7 Hz, 3H). LCMS calc. for C$_{23}$H$_{31}$FN$_5$O$_3$S$_2$ [M+H]$^+$: m/z=508.2; Found: 508.0.

Example 10. 10a-Isopropyl-2-(2-((1-(methylsulfonyl)piperidin-4-yl)amino)-5-(trifluoro-methyl)pyrimidin-4-yl)-6,7,10,10a-tetrahydrothieno[2',3':3,4]pyrrolo[1,2-d][1,4]oxazepin-4(9H)-one

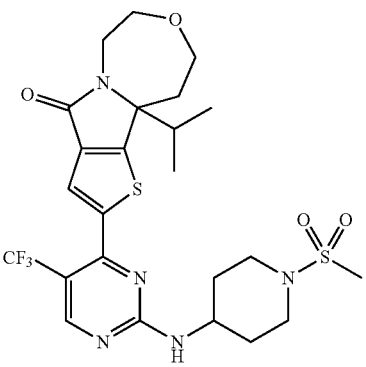 [SMILES: CC(C)C12CCOCCN1C(=O)c1cc(-c3nc(NC4CCN(S(C)(=O)=O)CC4)ncc3C(F)(F)F)sc12]

This compound was prepared using procedures analogous to those described for Example 1 Step 5-6 and Step 8 using bis(2-bromoethyl) ether to replace 1,4-diiodobutane in Step 5 to afford the title compound as its TFA salt. $^1$H NMR (400 MHz, CD$_3$OD) δ 8.60 (d, J=14.5 Hz, 1H), 7.89 (d, J=14.0 Hz, 1H), 4.14-3.95 (m, 2H), 3.91-3.80 (m, 2H), 3.78-3.70 (m, 2H), 3.55 (t, J=11.4 Hz, 1H), 3.37-3.30 (m, 1H), 3.08-2.90 (m, 3H), 2.87 (s, 3H), 2.65-2.49 (m, 1H), 2.49-2.33 (m, 2H), 2.21-2.03 (m, 2H), 1.81-1.61 (m, 2H), 1.25 (d, J=6.6 Hz, 3H), 0.53 (s, 3H). LCMS calc. for C$_{24}$H$_{31}$F$_3$N$_5$O$_4$S$_2$ [M+H]$^+$: m/z=574.2; Found: 574.0.

Example 11. 8a-Isopropyl-2-(2-((1-(methylsulfonyl)piperidin-4-yl)amino)-5-(trifluoro-methyl)pyrimidin-4-yl)-6,7,8,8a-tetrahydro-4H-thieno[2,3-a]pyrrolizin-4-one

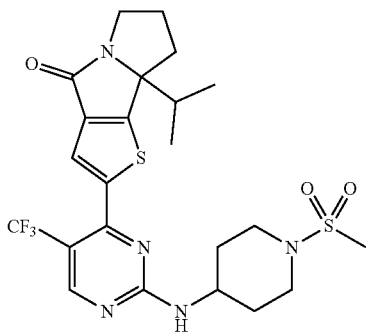 [SMILES: CC(C)C12CCCN1C(=O)c1cc(-c3nc(NC4CCN(S(C)(=O)=O)CC4)ncc3C(F)(F)F)sc12]

This compound was prepared using procedures analogous to those described for Example 1 Step 5-6 and Step 8 using 1,3-dibromopropane to replace 1,4-diiodobutane in Step 5 to afford the title compound as its TFA salt. LCMS calc. for C$_{23}$H$_{29}$F$_3$N$_5$O$_3$S$_2$ [M+H]$^+$: m/z=544.2; Found: 544.0.

Example 12 or Example 13. (8aS)-8a-Isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one and (8aR)-8a-Isopropyl-2-(2-((1-(methylsulfonyl)piperidin-4-yl)amino)-5-(trifluoro-methyl)pyrimidin-4-yl)-6,7,8,8a-tetrahydro-4H-thieno[2,3-a]pyrrolizin-4-one Example 12 or Example 13

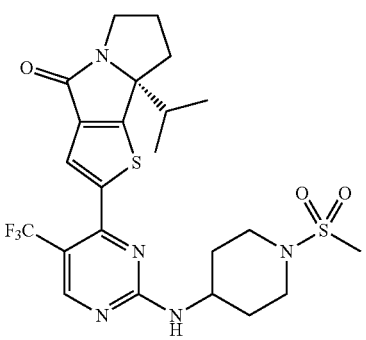

and

Example 13 or Example 12

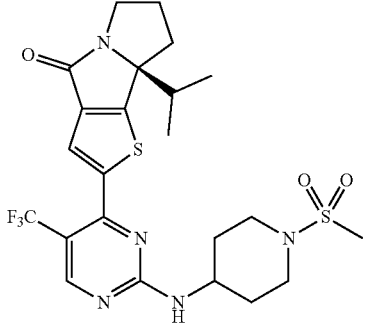

The racemic material of 8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one was purified by chiral-HPLC Column under chiral-HPLC separation conditions: Lux Amylose-1; Mobile Phase: 70:30 Hexanes/Ethanol (Denatured); Composition/Flow: 30 mL/min. The peaks were analyzed by chiral-HPLC. Column: Lux Amylose-1; Mobile Phase: 70:30 Hexanes:Ethanol (denatured); Composition/Flow: 1.0 mL/min; Peak 1 (ee: 100%, retention time: R$_t$=6.38 min) was assigned to Example 12 or Example 13, LCMS calc. for C$_{23}$H$_{29}$F$_3$N$_5$O$_3$S$_2$ [M+H]$^+$: m/z=544.2; Found: 544.0. Peak 2 (ee: 93%, retention time: R$_t$=7.99 min), LCMS calc. for C$_{23}$H$_{29}$F$_3$N$_5$O$_3$S$_2$ [M+H]$^+$: m/z=544.2; Found: 543.9.

Example 14. 8a-Ethyl-2-[2-[(1-methylsulfonylpiperidin-4-yl)amino]-5-(trifluoromethyl) pyrimidin-4-yl]-7,8-dihydro-6H-thieno[2,3-a]pyrrolizin-4-one

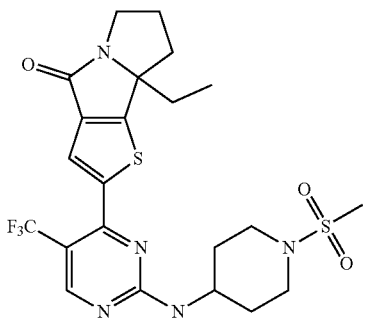

Step 1. 8a-Ethyl-7,8-dihydro-6H-thieno[2,3-a]pyrrolizin-4-one

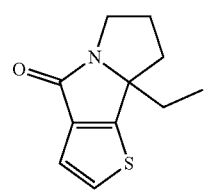

A mixture of 5,6-dihydro-4H-thieno[2,3-c]pyrrol-4-one (200 mg, 1.44 mmol) and NaH (223 mg, 5.75 mmol) in anhydrous DMF (6 mL) under $N_2$ was stirred at r.t. for 15 mins., and then cooled to 0° C. 1,3-Diiodopropane (0.20 mL, 1.72 mmol) was added. The reaction mixture was stirred at r.t. for 3 h. Then iodoethane (269 mg, 1.72 mmol) was added and stirred for 1 h. Additional portions of NaH (1.3 eq.) and iodoethane (1.3 eq.) were added. The reaction was stirred for 1 h., and then poured into cold saturated $NH_4Cl$ solution (6 mL). The mixture was extracted with EtOAc (6 mL×3). The combined organic layers were dried over $Na_2SO_4$, filtered, and concentrated under reduced pressure. The residue was purified by prep-HPLC on C18 column eluting with MeCN/$H_2O$ (10-50% with 0.1% TFA) to give 8a-ethyl-7,8-dihydro-6H-thieno[2,3-a]pyrrolizin-4-one (60.0 mg, 20.1% yield). LCMS calc. for $C_{11}H_{14}NOS$ $[M+H]^+$: m/z=208.1; Found: 208.0.

Step 2. 2-Bromo-8a-ethyl-7,8-dihydro-6H-thieno[2,3-a]pyrrolizin-4-one

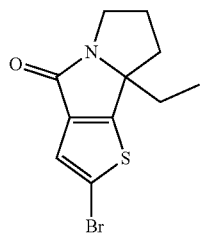

To a mixture of 8a-ethyl-7,8-dihydro-6H-thieno[2,3-a]pyrrolizin-4-one (60.0 mg, 0.29 mmol) and N-bromosuccinimide (56.7 mg, 0.32 mmol) in MeCN (3 mL) was added acetic acid (1 drop). The reaction was stirred at 60° C. for 6 h. The solvent was removed. The residue was purified by flash chromatography on a silica gel eluting with EtOAc/heptane (0-60%) to afford 2-bromo-8a-ethyl-7,8-dihydro-6H-thieno[2,3-a]pyrrolizin-4-one (72.1 mg, 87.2% yield). LCMS calc. for $C_{11}H_{13}BrNOS$ $[M+H]^+$: m/z=285.99/287.99; Found: 285.9/287.9.

Step 3. 8a-Ethyl-2-[2-[(1-methylsulfonylpiperidin-4-yl)amino]-5-(trifluoromethyl) pyrimidin-4-yl]-7,8-dihydro-6H-thieno[2,3-a]pyrrolizin-4-one This compound was prepared using procedures analogous to those described for Example 1 Step 8 using 2-bromo-8a-ethyl-7,8-dihydro-6H-thieno[2,3-a]pyrrolizin-4-one and 4-chloro-N-(1-(methylsulfonyl)piperidin-4-yl)-5-(trifluoromethyl)pyrimidin-2-amine to afford the title compound as its TFA salt. $^1$H NMR (300 MHz, $CD_3OD$) δ 8.57 (d, J=11.2 Hz, 1H), 7.76 (d, J=12.8 Hz, 1H), 4.03 (s, 1H), 3.80-3.65 (m, 3H), 3.28 (s, 1H), 2.98 (q, J=11.5, 10.9 Hz, 2H), 2.85 (d, J=6.6 Hz, 3H), 2.53-2.32 (m, 2H), 2.18 (ddd, J=18.3, 9.1, 5.6 Hz, 3H), 1.97 (d, J=8.4 Hz, 2H), 1.70 (d, J=9.2 Hz, 3H), 0.78 (t, J=7.3 Hz, 3H). LCMS calc. for $C_{22}H_{27}F_3N_5O_3S_2$ $[M+H]^+$: m/z=530.1; Found 529.9.

Example 15. 8a-Ethyl-2-[5-fluoro-2-[(1-methylsulfonylpiperidin-4-yl)amino]pyrimidin-4-yl]-7,8-dihydro-6H-thieno[2,3-a]pyrrolizin-4-one

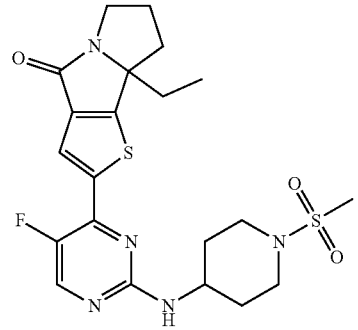 [SMILES: CCC12CCCN1C(=O)c1cc(-c3nc(NC4CCN(S(C)(=O)=O)CC4)ncc3F)sc12]

This compound was prepared using procedures analogous to those described for Example 6 Step 3 & 4 using 2-bromo-8a-ethyl-7,8-dihydro-6H-thieno[2,3-a]pyrrolizin-4-one to replace 2-bromo-9a-methyl-7,8,9,9a-tetrahydrothieno[2,3-a]indolizin-4(6H)-one in Step 3 to afford the title compound as its TFA salt. $^1$H NMR (300 MHz, $CD_3OD$) δ 8.28 (d, J=3.5 Hz, 1H), 7.82 (d, J=1.5 Hz, 1H), 3.89 (td, J=10.5, 5.2 Hz, 1H), 3.70 (dd, J=11.5, 7.2 Hz, 3H), 3.33 (d, J=4.3 Hz, 1H), 3.03-2.91 (m, 2H), 2.86 (s, 3H), 2.49-2.33 (m, 2H), 2.23-2.08 (m, 3H), 2.02-1.91 (m, 2H), 1.77-1.57 (m, 3H), 0.77 (t, J=7.3 Hz, 3H). LCMS calc. for $C_{21}H_{27}FN_5O_3S_2$ $[M+H]^+$: m/z=480.1, Found 479.8.

Example 16. 8a-Ethyl-2-[5-methyl-2-[(1-methylsulfonylpiperidin-4-yl)amino]pyrimidin-4-yl]-7,8-dihydro-6H-thieno[2,3-a]pyrrolizin-4-one

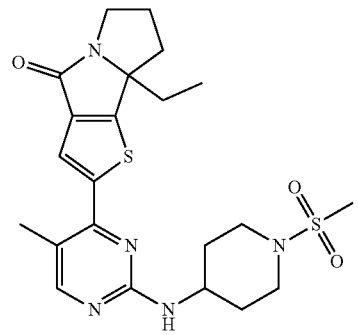 [SMILES: CCC12CCCN1C(=O)c1cc(-c3nc(NC4CCN(S(C)(=O)=O)CC4)ncc3C)sc12]

Step 1. 2-(2-Chloro-5-methyl-1,6-dihydropyrimidin-6-yl)-8a-ethyl-7,8-dihydro-6H-thieno[2,3-a]pyrrolizin-4-one

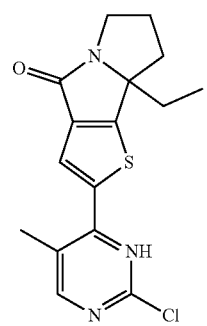 [SMILES: CCC12CCCN1C(=O)c1cc(-c3nc(Cl)ncc3C)sc12]

To a solution of 2-bromo-8a-ethyl-7,8-dihydro-6H-thieno[2,3-a]pyrrolizin-4-one (30.0 mg, 0.10 mmol) in THF (1 mL) was added n-butyllithium (0.105 mL, 0.26 mmol, 2.5 M in hexane) dropwise at −78° C. under N₂. The reaction mixture was stirred at −78° C. for 30 min. and then 2-chloro-5-methylpyrimidine (27 mg, 0.21 mmol) was added. The resulting mixture was stirred at −78° C. for an additional 30 min., and quenched with saturated NH₄Cl solution (3 mL). The mixture was extracted with DCM (3 mL×3). The combined organic layers were washed with brine (5 mL), dried over Na₂SO₄, filtered and concentrated to yield 2-(2-chloro-5-methyl-1,6-dihydropyrimidin-6-yl)-8a-ethyl-7,8-dihydro-6H-thieno[2,3-a]pyrrolizin-4-one (33 mg), which was used for the next reaction without further purification. LCMS calc. for C₁₆H₁₉C₁N₃OS [M+H]⁺: m/z=336.09/338.09; found 335.9/337.9.

Step 2. 2-(2-Chloro-5-methylpyrimidin-4-yl)-8a-ethyl-7,8-dihydro-6H-thieno[2,3-a]pyrrolizin-4-one

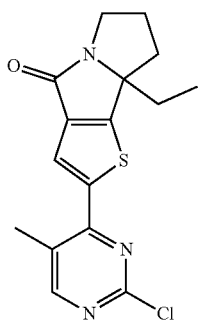 [SMILES: CCC12CCCN1C(=O)c1cc(-c3nc(Cl)ncc3C)sc12]

To a solution of 2-(2-chloro-5-methyl-1,6-dihydropyrimidin-6-yl)-8a-ethyl-7,8-dihydro-6H-thieno[2,3-a]pyrrolizin-4-one (33 mg) in THF (2 mL) was added 2,3 dichloro-5,6-dicyano-p-benzoquinone (22.3 mg, 0.98 mmol). The reaction mixture was stirred at r.t. overnight. The reaction was diluted with DCM (5 mL) and washed with hot 10% K₂CO₃ solution (3 mL) and brine (3 mL), dried over Na₂SO₄, filtered and concentrated. The residue was purified by prep-HPLC on a C18 column eluting with MeCN/H₂O (20-80% with 0.1% TFA) to yield 2-(2-chloro-5-methylpyrimidin-4-yl)-8a-ethyl-7,8-dihydro-6H-thieno[2,3-a]pyrrolizin-4-one (17.3 mg, 52.7% yield). ¹H NMR (300 MHz, CDCl₃) δ 8.45 (s, 1H), 7.74 (s, 1H), 3.79 (d, J=1.7 Hz, 1H), 3.36-3.25 (m, 1H), 2.53 (s, 3H), 2.42-2.33 (m, 2H), 2.18-2.08 (m, 1H), 1.95-1.88 (m, 2H), 1.69 (dt, J=12.4, 10.0 Hz, 1H), 0.83 (t, J=7.4 Hz, 3H). LCMS calc. for C₁₆H₁₇C₁N₃OS [M+H]⁺: m/z=334.08/336.08; found 333.9/335.9.

Step 3. 8a-Ethyl-2-[5-methyl-2-[(1-methylsulfonylpiperidin-4-yl)amino]pyrimidin-4-yl]-7,8-dihydro-6H-thieno[2,3-a]pyrrolizin-4-one This compound was prepared using procedures analogous to those described for Example 6 Step 4 using 2-(2-Chloro-5-methylpyrimidin-4-yl)-8a-ethyl-7,8-dihydro-6H-thieno[2,3-a]pyrrolizin-4-one to afford the title compound as its TFA salt. ¹H NMR (300 MHz, CD₃OD) δ 8.18 (d, J=0.8 Hz, 1H), 7.86 (s, 1H), 4.00 (s, 1H), 3.79-3.67 (m, 3H), 3.35-3.31 (m, 1H), 2.99 (t, J=11.6 Hz, 2H), 2.87 (s, 3H), 2.46 (d, J=0.8 Hz, 4H), 2.43-2.36 (m, 1H), 2.25-2.10 (m, 3H), 1.98 (q, J=7.3 Hz, 2H), 1.80-1.63 (m, 3H), 0.77 (t, J=7.3 Hz, 3H). LCMS calc. for C₂₂H₃₀N₅O₃S₂ [M+H]⁺: m/z=476.18; Found 475.9.

Example 17. 8a-(Hydroxymethyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

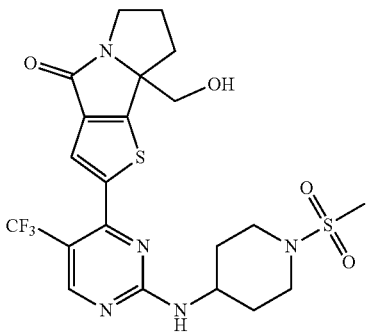 [SMILES: CS(=O)(=O)N1CCC(Nc2ncc(C(F)(F)F)c(-c3cc4c(s3)C3(CO)CCCN3C4=O)n2)CC1]

Step 1. 6,7,8,8a-Tetrahydro-4H-thieno[2,3-a]pyrrolizin-4-one

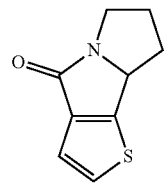 [SMILES: O=C1c2ccsc2C2CCCN12]

A mixture of 5,6-dihydro-4H-thieno[2,3-c]pyrrol-4-one (960 mg, 6.9 mmol) and NaH (662 mg, 27.6 mmol) in anhydrous DMF (45 mL) under N₂ was stirred at r.t. for 15 mins., and then cooled to 0° C. 1,3-Diiodopropane (0.83 mL, 7.24 mmol) was added. The reaction mixture was stirred at r.t. for 3 h, and then poured into cold saturated NH₄Cl solution (6 mL). The mixture was extracted with EtOAc three times. The combined organic layers were dried over Na₂SO₄, filtered, and concentrated under reduced pressure. The residue was purified by prep-HPLC on C18 column eluting with MeCN/H₂O (8-45% with 0.1% TFA) to afford the title compound (455 mg, 36.8% yield). LCMS calc. for C₉H₁₀NOS [M+H]⁺: m/z=180.0; Found: 180.0.

Step 2. 8a-(Bromomethyl)-6,7,8,8a-tetrahydro-4H-thieno[2,3-a]pyrrolizin-4-one

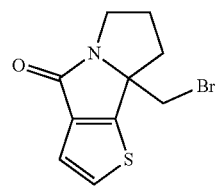 [SMILES: O=C1c2ccsc2C2(CBr)CCCN12]

A mixture of 6,7,8,8a-tetrahydro-4H-thieno[2,3-a]pyrrolizin-4-one (300 mg, 1.67 mmol) and NaH (268 mg, 6.69 mmol) in anhydrous DMF (20 mL) under N₂ was stirred at r.t. for 15 mins., and then cooled to 0° C. Dibromomethane (1.16 mL, 16.7 mmol) was added. The reaction mixture was stirred at r.t. overnight, and then poured into cold saturated NH$_4$Cl solution (6 mL). The mixture was extracted with EtOAc three times. The combined organic layers were dried over Na$_2$SO$_4$, filtered, and concentrated under reduced pressure. The residue was purified by prep-HPLC on C18 column eluting with MeCN/H$_2$O (30-55% with 0.1% TFA) to afford the title compound (226 mg, 49.6% yield). LCMS calc. for C$_{10}$H$_{11}$BrNOS [M+H]$^+$: m/z=274.0/272.0; Found: 273.8/271.8.

Step 3. 8a-(Iodomethyl)-6,7,8,8a-tetrahydro-4H-thieno[2,3-a]pyrrolizin-4-one

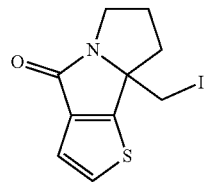 [SMILES: O=C1c2ccsc2C2(CI)CCCN12]

A mixture of 8a-(bromomethyl)-6,7,8,8a-tetrahydro-4H-thieno[2,3-a]pyrrolizin-4-one (80 mg, 0.29 mmol) and NaI (220 mg, 1.47 mmol) in acetone (1.5 mL) was stirred in a sealed tube at 80° C. for 24 h. The reaction was cooled to rt and diluted by water. The mixture was extracted by DCM three times. The combined organic layers were washed with Na$_2$S$_2$O$_3$ solution and dried over Na$_2$SO$_4$, filtered and concentrated under reduced pressure to afford the title compound (88 mg, 94% yield). LCMS calc. for C$_{10}$H$_{11}$INOS [MS+H]$^+$:320.0; Found: 319.8.

Step 4. 8a-(Hydroxymethyl)-6,7,8,8a-tetrahydro-4H-thieno[2,3-a]pyrrolizin-4-one

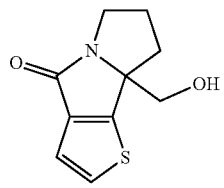 [SMILES: O=C1c2ccsc2C2(CO)CCCN12]

A mixture of 8a-(iodomethyl)-6,7,8,8a-tetrahydro-4H-thieno[2,3-a]pyrrolizin-4-one (60 mg, 0.19 mmol) and AgBF$_4$ (47 mg, 0.24 mmol) in nitromethane (1.3 mL) and DMF (0.52 mL) was stirred at 50° C. for 4 h in a sealed tube under N$_2$. The reaction was cooled to rt. Next MeOH (10 mL) and Na$_2$CO$_3$ (109 mg, 1.03 mmol) was added. The reaction was stirred at rt for 1 h. The reaction was poured into water and extracted with EtOAc three times. The combined organic layers were dried over Na$_2$SO$_4$, filtered, and concentrated under reduced pressure. The residue was purified by prep-HPLC on C18 column eluting with MeCN/H$_2$O (8-55% with 0.1% TFA) to the title compound (35 mg, 89% yield). LCMS calc. for C$_{10}$H$_{12}$NO$_2$S [MS+H]$^+$: 210.1; Found: 210.0.

Step 5. 8a-(Hydroxymethyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 1 Step 6 and 8. LCMS calc. for C$_{21}$H$_{25}$F$_3$N$_5$O$_4$S$_2$ [M+H]$^+$: m/z=532.1; Found 531.9.

Example 18. 8a-(Fluoromethyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

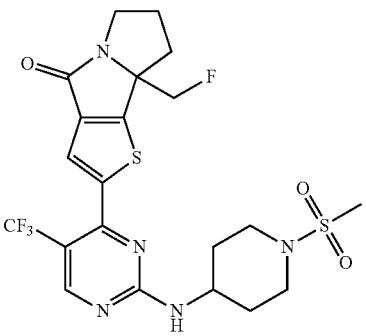 [SMILES: CS(=O)(=O)N1CCC(Nc2ncc(C(F)(F)F)c(-c3cc4c(s3)C3(CF)CCCN3C4=O)n2)CC1]

A solution of 8a-(hydroxymethyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one (8.0 mg, 0.015 mmol) (Example 17) in DCM (2 mL) was cooled to −78° C. A solution of diethylaminosulfur trifluoride (0.0060 mL, 0.045 mmol) in DCM (0.5 mL) was added to the reaction. The reaction mixture was slowly warmed to rt and stirred at rt for 1 h. The reaction was quenched with MeOH and concentrated. The residue was purified by prep-HPLC on C18 column eluting with MeCN/H$_2$O (30-60% with 0.1% TFA) to afford the title compound (7.0 mg, 87% yield) as its TFA salt. LCMS calc. for C$_{21}$H$_{24}$F$_4$N$_5$O$_3$S$_2$ [M+H]$^+$: m/z=534.1; Found: 534.0.

Example 19. 8a-(2-Fluoroethyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

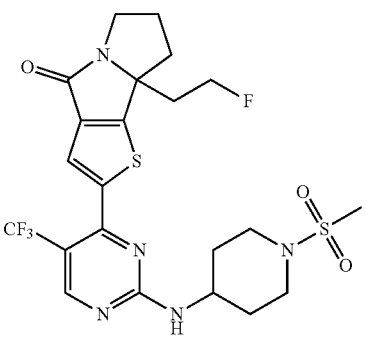 [SMILES: CS(=O)(=O)N1CCC(Nc2ncc(C(F)(F)F)c(-c3cc4c(s3)C3(CCF)CCCN3C4=O)n2)CC1]

This compound was prepared using procedures analogous to those described for Example 14 Step 1-3 using 1-fluoro-2-iodoethane to replace iodoethane in Step 1. LCMS calc. for $C_{22}H_{26}F_4N_5O_3S_2$ [M+H]$^+$: m/z=548.1; Found: 547.9.

Example 20. 8a-Methyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one

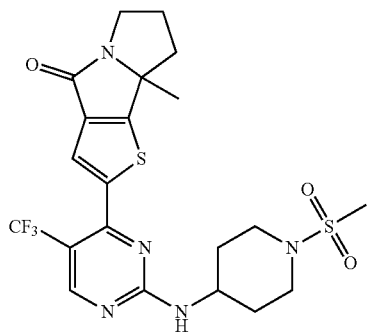 [SMILES: CC12CCCN1C(=O)c1cc(-c3nc(NC4CCN(S(C)(=O)=O)CC4)ncc3C(F)(F)F)sc12]

This compound was prepared using procedures analogous to those described for Example 14 Step 1-3 using iodomethane to replace iodoethane in Step 1. LCMS calc. for $C_{21}H_{25}F_3N_5O_3S_2$ [M+H]$^+$: m/z=516.1; Found: 516.0.

Example 21. 2-(2-((1-(Methylsulfonyl)piperidin-4-yl)amino)-5-(trifluoromethyl)pyrimidin-4-yl)-6,7,8,8a-tetrahydro-4H-thieno[2,3-a]pyrrolizin-4-one

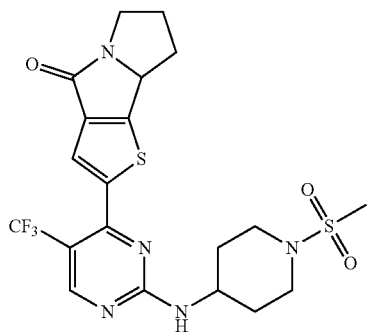 [SMILES: CS(=O)(=O)N1CCC(Nc2ncc(C(F)(F)F)c(-c3cc4c(s3)C3CCCN3C4=O)n2)CC1]

This compound was prepared using procedures analogous to those described for Example 14 Step 1-3. LCMS calc. for $C_{20}H_{23}F_3N_5O_3S_2$ [M+H]$^+$: m/z=502.1; Found: 502.0.

Example 22. 8a-Cyclopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

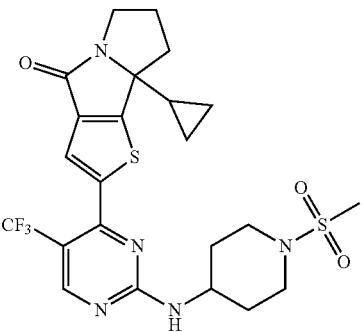 [SMILES: CS(=O)(=O)N1CCC(Nc2ncc(C(F)(F)F)c(-c3cc4c(s3)C3(C5CC5)CCCN3C4=O)n2)CC1]

This compound was prepared using procedures analogous to those described for Example 1 Step 1-8, using cyclopropanecarbaldehyde to replace isobutyraldehyde in Step 1, and 1,3-dibromopropane to replace 1,4-diiodobutane in Step 5. LCMS calc. for $C_{23}H_{27}F_3N_5O_3S_2$ [M+H]$^+$: m/z=542.2; Found: 542.1.

Example 23. 8a-Cyclobutyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

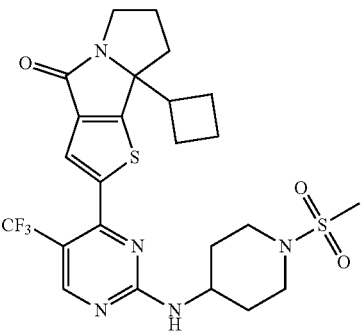 [SMILES: CS(=O)(=O)N1CCC(Nc2ncc(C(F)(F)F)c(-c3cc4c(s3)C3(C5CCC5)CCCN3C4=O)n2)CC1]

This compound was prepared using procedures analogous to those described for Example 1 Step 1-8, using cyclobutanecarbaldehyde to replace isobutyraldehyde in Step 1, and 1,3-dibromopropane to replace 1,4-diiodobutane in Step 5. LCMS calc. for $C_{24}H_{29}F_3N_5O_3S_2$ [M+H]$^+$: m/z=556.2; Found: 555.9.

Example 24. 8a-(3,3-Difluorocyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

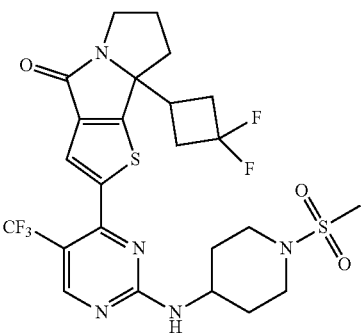 [SMILES: CS(=O)(=O)N1CCC(Nc2ncc(C(F)(F)F)c(-c3cc4c(s3)C3(C5CC(F)(F)C5)CCCN3C4=O)n2)CC1]

This compound was prepared using procedures analogous to those described for Example 1 Step 1-8, using 3,3-difluorocyclobutane-1-carbaldehyde to replace isobutyraldehyde in Step 1, and 1,3-dibromopropane to replace 1,4-diiodobutane in Step 5. LCMS calc. for $C_{24}H_{27}F_5N_5O_3S_2$ [M+H]$^+$: m/z=592.2; Found: 591.9.

Example 25. 8a-(3-Hydroxycyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

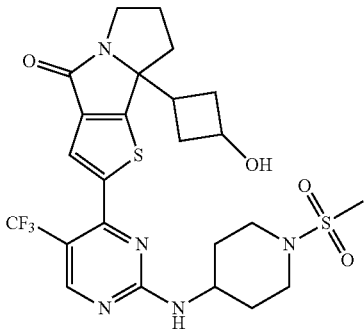 [SMILES: CS(=O)(=O)N1CCC(Nc2ncc(C(F)(F)F)c(-c3cc4c(s3)C3(C5CC(O)C5)CCCN3C4=O)n2)CC1]

Step 1. (3-(Benzyloxy)cyclobutyl)methanol

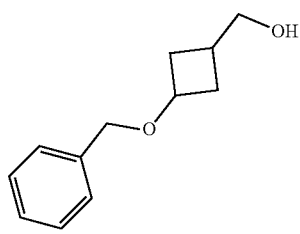 [SMILES: OCC1CC(OCc2ccccc2)C1]

To a solution of 3-phenylmethoxycyclobutane-1-carboxylic acid (10.0 g, 48.5 mmol) in THF (100 mL) was added borane dimethyl sulfide complex (7.37 g, 97.0 mmol) dropwise at 0° C. The reaction mixture was stirred at rt for 1 h, then 60° C. for 3 h. The reaction was cooled to 0° C. and quenched with MeOH, stirred at rt for 30 min. The solvent was removed under reduced pressure. The residue was purified by silica gel chromatography eluting with EtOAc/heptane (0-30%) to afford the title compound (8.40 g, 90.1% yield).

Step 2. 3-(Benzyloxy)cyclobutane-1-carbaldehyde

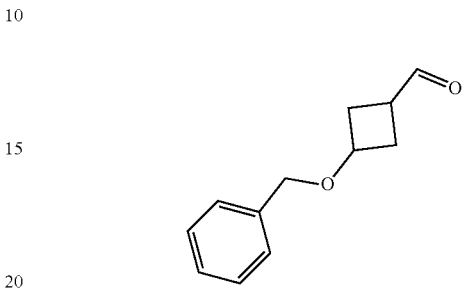

To a solution of (3-phenylmethoxycyclobutyl)methanol (5.0 g, 26.0 mmol) in DCM (50 mL) was added Dess-Martin Periodinane (13.2 g, 31.2 mmol) portion wise. The reaction mixture was stirred at rt for 1 h. The reaction was quenched with saturated NaHCO$_3$ solution (20 mL) and 10% Na$_2$S$_2$O$_3$ solution (20 mL), and stirred at rt for 30 min. The mixture was extracted with DCM (20 mL×3). The combined organic layers were dried over Na$_2$SO$_4$, filtered and concentrated. The residue was purified by silica gel chromatography eluting with EtOAc/heptane (0-20%) to yield the title compound (3.10 g, 62.7% yield).

Step 3. 8a-(3-(Benzyloxy)cyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-on

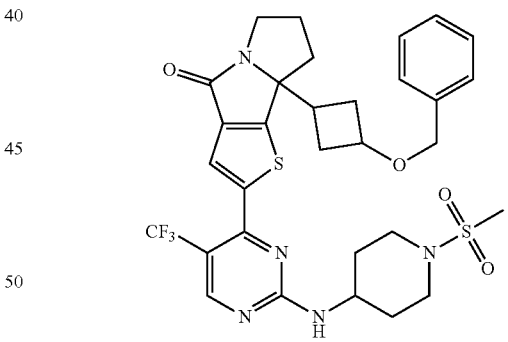

This compound was prepared using procedures analogous to those described for Example 1 Step 1-8, using 3-(benzyloxy)cyclobutane-1-carbaldehyde to replace isobutyraldehyde in Step 1, and 1,3-dibromopropane to replace 1,4-diiodobutane in Step 5. LCMS calc. for $C_{31}H_{35}F_3N_5O_4S_2$ [M+H]$^+$: m/z=662.2; Found: 662.1.

Step 4. 8a-(3-Hydroxycyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one To a solution of 8a-(3-(benzyloxy)cyclobutyl)-2-(2-((1-(methylsulfonyl)piperidin-4-yl)amino)-5-(trifluoromethyl)

pyrimidin-4-yl)-6,7,8,8a-tetrahydro-4H-thieno[2,3-a]pyrrolizin-4-one (19.0 mg, 0.0289 mmol) in DCM (1 mL) was added BCl$_3$ (0.086 mL, 0.086 mmol) (1.0 M in DCM) dropwise at −78° C. The reaction mixture was stirred at −78° C. for 2 h. The reaction was quenched with MeOH (3 mL) and purified by prep-HPLC on C18 column eluting with MeCN/H$_2$O (20-60% with 0.1% TFA) to afford the title compound (3.9 mg, 23% yield) as its TFA salt. LCMS calc. for $C_{24}H_{29}F_3N_5O_4S_2$ [M+H]$^+$: m/z=572.2; Found: 571.9.

Example 26. 8a-(3-Fluorocyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

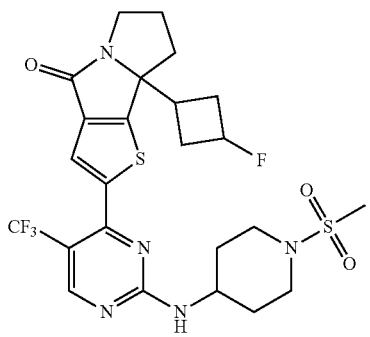 [SMILES: CS(=O)(=O)N1CCC(Nc2ncc(C(F)(F)F)c(-c3cc4c(s3)C3(C5CC(F)C5)CCCN3C4=O)n2)CC1]

This compound was prepared using procedures analogous to those described for Example 18, using Example 25 as starting material. LCMS calc. for $C_{24}H_{28}F_4N_5O_3S_2$ [M+H]$^+$: m/z=574.2; Found: 573.9.

Example 27. 2-(5-Chloro-2-((1-(methylsulfonyl)piperidin-4-yl)amino)pyrimidin-4-yl)-8a-ethyl-6,7,8,8a-tetrahydro-4H-thieno[2,3-a]pyrrolizin-4-one

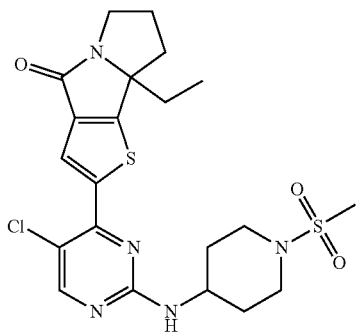 [SMILES: CCC12CCCN1C(=O)c1cc(-c3nc(NC4CCN(S(C)(=O)=O)CC4)ncc3Cl)sc12]

This compound was prepared using procedures analogous to those described for Example 14, Steps 1-2 and Example 6, Steps 3-4, using 2,4,5-trichloropyrimidine to replace 2,6-dichloro-5-fluorouracil in Example 6 Step 3. LCMS calc. for $C_{21}H_{27}ClN_5O_3S_2$ [M+H]$^+$: m/z=496.1; Found: 495.8.

Example 28. 8a-Ethyl-2-(2-((1-(methylsulfonyl)piperidin-4-yl)amino)pyrimidin-4-yl)-6,7,8,8a-tetrahydro-4H-thieno[2,3-a]pyrrolizin-4-one

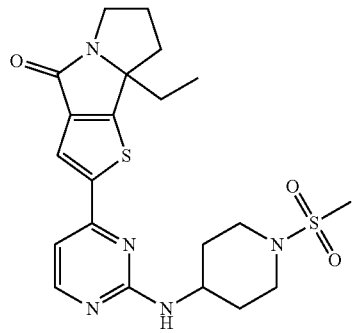 [SMILES: CCC12CCCN1C(=O)c1cc(-c3ccnc(NC4CCN(S(C)(=O)=O)CC4)n3)sc12]

This compound was prepared using procedures analogous to those described for Example 16, Steps 1-3, using 2-chloropyrimidine to replace 2-chloro-5-methylpyrimidine. LCMS calc. for $C_{21}H_{28}N_5O_3S_2$ [M+H]$^+$: m/z=462.2; Found: 462.0.

Example 29. 7-Hydroxy-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

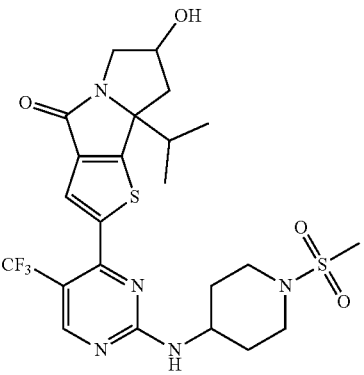 [SMILES: CC(C)C12CC(O)CN1C(=O)c1cc(-c3nc(NC4CCN(S(C)(=O)=O)CC4)ncc3C(F)(F)F)sc12]

Step 1. 8a-Isopropyl-7-methylene-6,7,8,8a-tetrahydro-4H-thieno[2,3-a]pyrrolizin-4-one

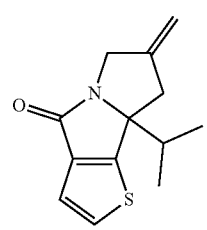 [SMILES: C=C1CN2C(=O)c3ccsc3C2(C(C)C)C1]

This compound was prepared using procedures analogous to those described for Example 1, Steps 5, using 3-chloro- 2-(chloromethyl)prop-1-ene to replace 1,4-diiodobutane. LCMS calc. for $C_{13}H_{16}NOS$ [M+H]$^+$: m/z=234.1; Found: 234.1.

Step 2. 8a-Isopropyl-8,8a-dihydro-4H-thieno[2,3-a] pyrrolizine-4,7(6H)-dione

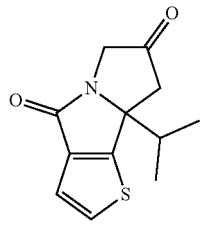 [SMILES: CC(C)C12CC(=O)CN1C(=O)c1ccsc12]

To a solution of 8a-isopropyl-7-methylene-6,7,8,8a-tetrahydro-4H-thieno[2,3-a]pyrrolizin-4-one (50.0 mg, 0.21 mmol) in 1,4-dioxane (2.0 mL) and water (0.5 mL) was added 2,6-lutidine (45.9 mg, 0.43 mmol), OsO$_4$ solution (0.40 mL, 0.032 mmol) and sodium periodate (183 mg, 0.86 mmol). The reaction mixture was stirred at rt overnight. The reaction was diluted with DCM (5 mL) and washed with water (3 mL) and brine (3 mL), dried over Na$_2$SO$_4$, filtered and concentrated. The residue was purified by silica gel chromatography eluting with EtOAc/heptane (0-25%) to yield the title compound (34.0 mg, 0.14 mmol, 67.4% yield). LCMS calc. for $C_{12}H_{14}NO_2S$ [M+H]$^+$: m/z=236.1; Found: 236.0.

Step 3. 8a-Isopropyl-2-(2-((1-(methylsulfonyl)piperidin-4-yl)amino)-5-(trifluoromethyl)pyrimidin-4-yl)-8,8a-dihydro-4H-thieno[2,3-a]pyrrolizine-4,7(6H)-dione

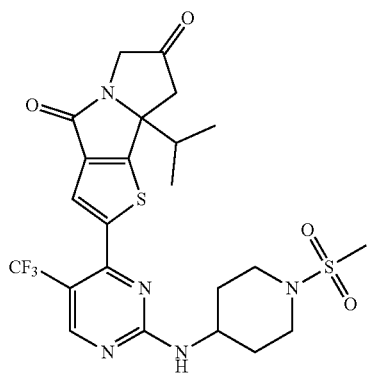 [SMILES: CC(C)C12CC(=O)CN1C(=O)c1cc(-c3nc(NC4CCN(S(C)(=O)=O)CC4)ncc3C(F)(F)F)sc12]

This compound was prepared using procedures analogous to those described for Example 1, Steps 6-8. LCMS calc. for $C_{23}H_{27}F_3N_5O_4S_2$ [M+H]$^+$: m/z=558.2; Found: 557.8.

Step 4. 7-Hydroxy-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one To a solution of 8a-isopropyl-2-(2-((1-(methylsulfonyl) piperidin-4-yl)amino)-5-(trifluoromethyl)pyrimidin-4-yl)-8, 8a-dihydro-4H-thieno[2,3-a]pyrrolizine-4,7(6H)-dione (18.0 mg, 0.032 mmol) in MeOH (1.0 mL) was added NaBH$_4$ (3.66 mg, 0.97 mmol). The reaction mixture was stirred at 0° C. for 1 h. The reaction was diluted with water (1 mL) and MeOH (2 mL) and purified by prep-HPLC on C18 column eluting with MeCN/H$_2$O (20-60% with 0.1% TFA) to afford the title compound (12 mg, 65% yield) as its TFA salt. LCMS calc. for $C_{23}H_{29}F_3N_5O_4S_2$ [M+H]$^+$: m/z=560.2; Found: 560.0.

Example 30. 8a-Isopropyl-7-methoxy-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

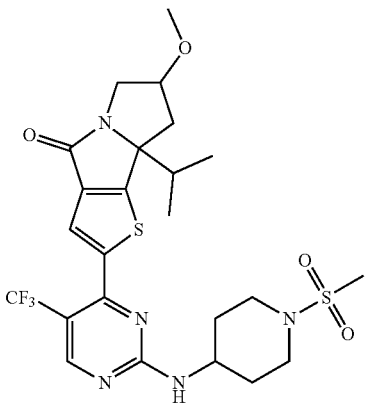 [SMILES: COC1CN2C(=O)c3cc(-c4nc(NC5CCN(S(C)(=O)=O)CC5)ncc4C(F)(F)F)sc3C2(C(C)C)C1]

To a solution of 7-hydroxy-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one (9.0 mg, 0.016 mmol) in MeCN (1 mL) was added iodomethane (3.4 mg, 0.024 mmol) and silver(I) oxide (11.2 mg, 0.048 mmol). The reaction mixture was stirred at 80° C. overnight. The reaction was diluted with MeCN (2 mL) and filtered. The filtrate was purified by prep-HPLC on C18 column eluting with MeCN/H$_2$O (20-80% with 0.1% TFA) to afford the title compound (3.1 mg, 31% yield) as its TFA salt. LCMS calc. for $C_{24}H_{31}F_3N_5O_4S_2$ [M+H]$^+$: m/z=574.2; Found: 574.1.

Example 31. 7-(Hydroxymethyl)-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

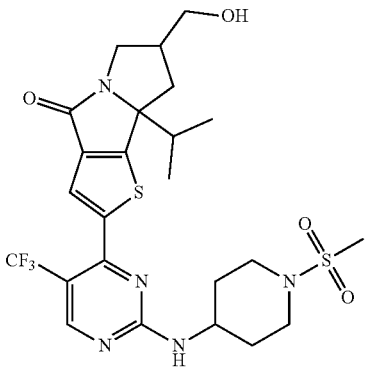 [SMILES: CC(C)C12CC(CO)CN1C(=O)c1cc(-c3nc(NC4CCN(S(C)(=O)=O)CC4)ncc3C(F)(F)F)sc12]

Step 1. 7-(Hydroxymethyl)-8a-isopropyl-6,7,8,8a-tetrahydro-4H-thieno[2,3-a]pyrrolizin-4-one

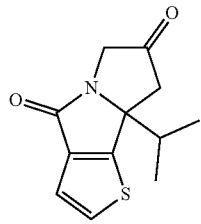 [SMILES: CC(C)C12CC(=O)CN1C(=O)c1ccsc12]

To a solution of 8a-isopropyl-7-methylene-6,7,8,8a-tetrahydro-4H-thieno[2,3-a]pyrrolizin-4-one (35 mg, 0.15 mmol) (Example 29, Step 1) in THF (2 mL) was added borane solution (0.45 mL, 0.45 mmol, 1.0 M in THF) dropwise at 0° C. The reaction mixture was stirred at rt overnight. The reaction was cooled to 0° C. and was added NaOH solution (0.75 mL, 1.5 mmol, 2.0 M aq.) and $H_2O_2$ solution (0.13 mL, 1.5 mmol, 35% aq.). The reaction mixture was stirred at rt for 2 h. The reaction was quenched with $Na_2S_2O_3$ solution (2 mL, 10% aq.) and extracted with DCM (3 mL×3). The combined organic layers were dried over $Na_2SO_4$, filtered and concentrated. The residue was purified by silica gel chromatography eluting with EtOAc/heptane (0-100%) to afford the title compound (21 mg, 0.084 mmol, 56% yield). LCMS calc. for $C_{13}H_{18}NO_2S$ $[M+H]^+$: m/z=252.1; Found: 252.1.

Step 2. 7-(Hydroxymethyl)-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 1, Steps 6-8. LCMS calc. for $C_{24}H_{31}F_3N_5O_4S_2$ $[M+H]^+$: m/z=574.2; Found: 574.1.

Example 32. 8a-Ethyl-7,7-difluoro-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

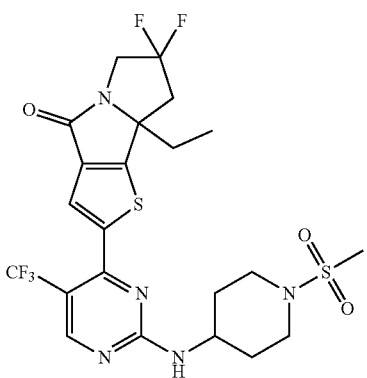 [SMILES: CCC12CC(F)(F)CN1C(=O)c1cc(-c3nc(NC4CCN(S(C)(=O)=O)CC4)ncc3C(F)(F)F)sc12]

Step 1. 8a-Ethyl-8,8a-dihydro-4H-thieno[2,3-a]pyrrolizine-4,7(6H)-dione

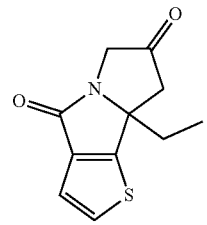

This compound was prepared using procedures analogous to those described for Example 29, Steps 1-2. LCMS calc. for $C_{11}H_{12}NO_2S$ $[M+H]^+$: m/z=222.1; Found: 222.0.

Step 2. 8a-Ethyl-7,7-difluoro-6,7,8,8a-tetrahydro-4H-thieno[2,3-a]pyrrolizin-4-one

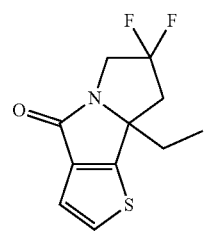 [SMILES: CCC12CC(F)(F)CN1C(=O)c1ccsc12]

This compound was prepared using procedures analogous to those described for Example 18. LCMS calc. for $C_{11}H_{12}F_2NOS$ $[M+H]^+$: m/z=244.1; Found: 244.0.

Step 3. 8a-Ethyl-7,7-difluoro-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 1, Steps 6-8. LCMS calc. for $C_{22}H_{25}F_5N_5O_3S_2$ $[M+H]^+$: m/z=566.1; Found: 566.1.

Example 33. 8a-Ethyl-7-hydroxy-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

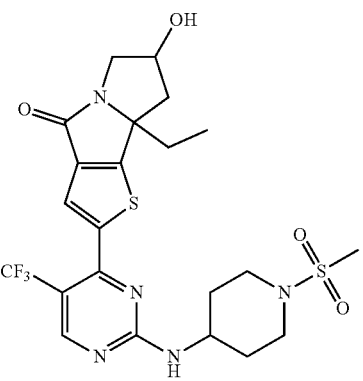 [SMILES: CCC12CC(O)CN1C(=O)c1cc(-c3nc(NC4CCN(S(C)(=O)=O)CC4)ncc3C(F)(F)F)sc12]

Step 1. 8a-Ethyl-2-(2-((1-(methylsulfonyl)piperidin-4-yl)amino)-5-(trifluoromethyl) pyrimidin-4-yl)-8,8a-dihydro-4H-thieno[2,3-a]pyrrolizine-4,7(6H)-dione

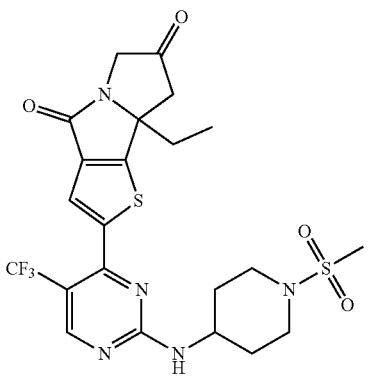 [SMILES: CCC12CC(=O)CN1C(=O)c1cc(-c3nc(NC4CCN(S(C)(=O)=O)CC4)ncc3C(F)(F)F)sc12]

This compound was prepared using procedures analogous to those described for Example 29, Steps 1-3. LCMS calc. for $C_{22}H_{25}F_3N_5O_4S_2$ [M+H]$^+$: m/z=544.1; Found: 544.0.

Step 2. 8a-Ethyl-7-hydroxy-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 29, Step 4. LCMS calc. for $C_{22}H_{27}F_3N_5O_4S_2$ [M+H]$^+$: m/z=546.2; Found: 546.0.

Example 34. 8a-Ethyl-7-hydroxy-7-methyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

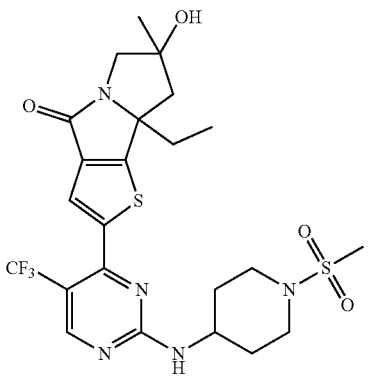 [SMILES: CCC12CC(C)(O)CN1C(=O)c1cc(-c3nc(NC4CCN(S(C)(=O)=O)CC4)ncc3C(F)(F)F)sc12]

To a solution of 8a-ethyl-2-(2-((1-(methylsulfonyl)piperidin-4-yl)amino)-5-(trifluoromethyl)pyrimidin-4-yl)-8,8a-dihydro-4H-thieno[2,3-a]pyrrolizine-4,7(6H)-dione (15.0 mg, 0.028 mmol) (Example 33, Step 1) in THF (1 mL) was added methylmagnesium bromide (0.092 mL, 0.28 mmol, 3.0 M in ether) dropwise at 0° C. The reaction mixture was stirred at rt overnight. The reaction was quenched with MeOH (1 mL) and purified by prep-HPLC on C18 column eluting with MeCN/H$_2$O (20-60% with 0.1% TFA) to afford the title compound (3.0 mg, 18% yield) as its TFA salt. LCMS calc. for $C_{23}H_{29}F_3N_5O_4S_2$ [M+H]$^+$: m/z=560.2; Found: 559.9.

Example 35. 8a-Ethyl-7,7-difluoro-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one

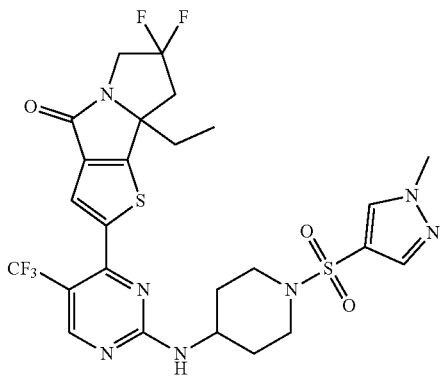 [SMILES: CCC12CC(F)(F)CN1C(=O)c1cc(-c3nc(NC4CCN(S(=O)(=O)c5cnn(C)c5)CC4)ncc3C(F)(F)F)sc12]

Step 1. Tert-butyl 4-((4-chloro-5-(trifluoromethyl)pyrimidin-2-yl)amino)piperidine-1-carboxylate

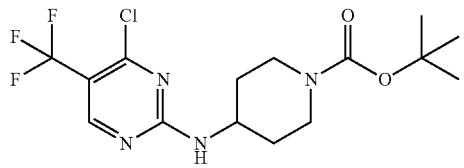 [SMILES: CC(C)(C)OC(=O)N1CCC(Nc2ncc(C(F)(F)F)c(Cl)n2)CC1]

To a solution of 2,4-dichloro-5-(trifluoromethyl)pyrimidine (25.0 g, 115 mmol) in DCE (200 mL)/tert-butanol (200 mL) was added zinc chloride (23.5 g, 173 mmol) at 0° C. The mixture was stirred for 1 h, followed by the dropwise addition of 4-amino-1-boc-piperidine (23.0 g, 115 mmol) and triethylamine (17.5 g, 173 mmol) at 0° C. The mixture was then stirred at 40° C. overnight. LCMS showed that the starting material was consumed. The solvent was removed under reduced pressure. The mixture was then added H$_2$O (200 mL) and extracted with ethyl acetate (200 mL×3). The combined organic layers were dried over Na$_2$SO$_4$, filtered, concentrated. The crude was then slurry washed in MeOH (20 mL) for 30 min, filtered to provide pure title compound (10.5 g, 23.4% yield). LCMS calc. for $C_{15}H_{21}ClF_3N_4O_2$ [M+H]$^+$: m/z=381.1; Found 381.1.

Step 2. 4-Chloro-N-(piperidin-4-yl)-5-(trifluoromethyl)pyrimidin-2-amine

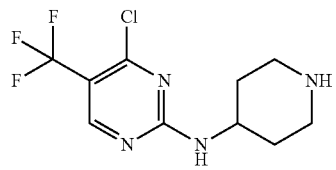 [SMILES: FC(F)(F)c1cnc(NC2CCNCC2)nc1Cl]

To a stirred mixture of tert-butyl 4-[[4-chloro-5-(trifluoromethyl)pyrimidin-2-yl]amino]piperidine-1-carboxylate (1200.0 mg, 3.15 mmol) in DCM (2.5 mL) was added TFA (1.0 mL, 13.07 mmol) dropwise. The mixture was stirred for 1 h. LCMS analysis indicated the reaction was complete. The crude product obtained was used directly without further purification. LCMS calc. for $C_{10}H_{13}ClF_3N_4[M+H]^+$: m/z=281.1; Found 281.2

Step 3. 4-Chloro-N-(1-((1-methyl-1H-pyrazol-4-yl)sulfonyl)piperidin-4-yl)-5-(trifluoromethyl)pyrimidin-2-amine

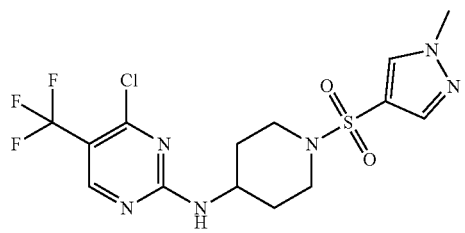 [SMILES: Cn1cc(S(=O)(=O)N2CCC(Nc3ncc(C(F)(F)F)c(Cl)n3)CC2)cn1]

To a solution of 4-chloro-N-piperidin-4-yl-5-(trifluoromethyl)pyrimidin-2-amine (800 mg, 2.83 mmol) in DMA (10.0 mL) was dropwise added 1-methylpyrazole-4-sulfonyl chloride (766 mg, 4.24 mmol) at 0° C., followed by the addition of DIPEA (1.10 g, 8.52 mmol). The mixture was then stirred at rt for 1 h. LCMS showed that the starting material was consumed. The residue was purified by prep-HPLC on a C18 column (10-80% MeCN in 0.1% TFA(aq), pH=2) to yield the title compound (640 mg, 53.3% yield). LCMS calc. for $C_{14}H_{17}ClF_3N_6O_2S$ $[M+H]^+$: m/z=425.1; Found 425.0.

Step 4. 8a-Ethyl-7,7-difluoro-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 1, Step 6 and Step 8, using appropriate intermediates, 8a-ethyl-7,7-difluoro-6,7,8,8a-tetrahydro-4H-thieno[2,3-a]pyrrolizin-4-one (Example 32, Step 2) and 4-chloro-N-(1-((1-methyl-1H-pyrazol-4-yl)sulfonyl)piperidin-4-yl)-5-(trifluoromethyl)pyrimidin-2-amine (Example 35, Step 3). LCMS calc. for $C_{25}H_{27}F_5N_7O_3S_2$ $[M+H]^+$: m/z=632.2; Found: 632.1.

Example 36. 8a-Ethyl-7-hydroxy-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one

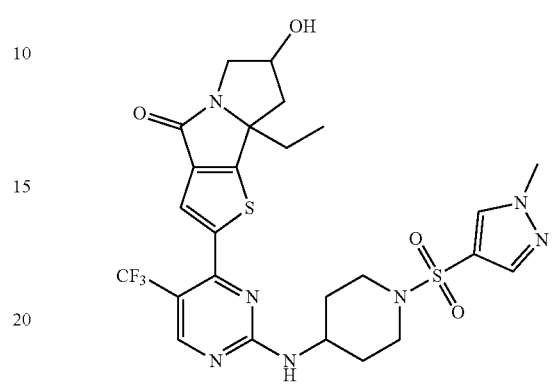

Step 1. 8a-Ethyl-2-(2-((1-((1-methyl-1H-pyrazol-4-yl)sulfonyl)piperidin-4-yl)amino)-5-(trifluoromethyl)pyrimidin-4-yl)-8,8a-dihydro-4H-thieno[2,3-a]pyrrolizine-4,7(6H)-dione

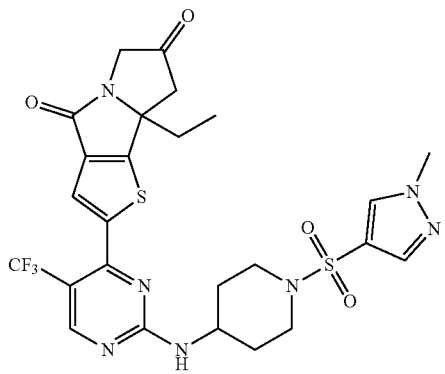 [SMILES: CCC12CC(=O)CN1C(=O)c1cc(-c3nc(NC4CCN(S(=O)(=O)c5cnn(C)c5)CC4)ncc3C(F)(F)F)sc12]

This compound was prepared using procedures analogous to those described for Example 1, Step 6 and Step 8, using appropriate intermediates 8a-ethyl-8,8a-dihydro-4H-thieno[2,3-a]pyrrolizine-4,7(6H)-dione (Example 32, Step 1) and 4-chloro-N-(1-((1-methyl-1H-pyrazol-4-yl)sulfonyl)piperidin-4-yl)-5-(trifluoromethyl)pyrimidin-2-amine (Example 35, Step 3). LCMS calc. for $C_{25}H_{27}F_3N_7O_4S_2[M+H]^+$: m/z=610.2; Found: 609.9.

Step 2. 8a-Ethyl-7-hydroxy-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one This compound was prepared using procedures analogous to those described for Example 29, Step 4. LCMS calc. for $C_{25}H_{29}F_3N_7O_4S_2$ $[M+H]^+$: m/z=612.2; Found: 612.1.

Example 37. 8a-Ethyl-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one

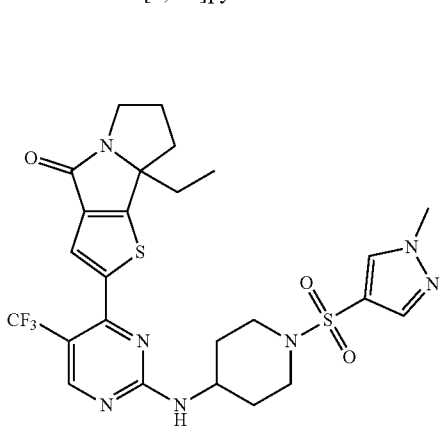

This compound was prepared using procedures analogous to those described for Example 35, Steps 1-4. LCMS calc. for C$_{25}$H$_{29}$F$_3$N$_7$O$_3$S$_2$ [M+H]$^+$: m/z=596.2; Found: 596.1.

Example 38. 8a-Ethyl-7-(methylamino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

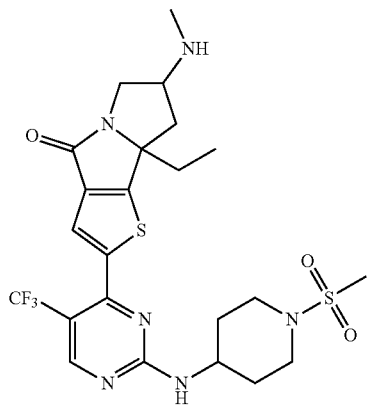 [SMILES: CCC12CC(NC)CN1C(=O)c1cc(-c3nc(NC4CCN(S(C)(=O)=O)CC4)ncc3C(F)(F)F)sc12]

To a solution of 8a-ethyl-2-(2-((1-(methylsulfonyl)piperidin-4-yl)amino)-5-(trifluoromethyl)pyrimidin-4-yl)-8,8a-dihydro-4H-thieno[2,3-a]pyrrolizine-4,7(6H)-dione (Example 33, Step 1) (23.6 mg, 0.043 mmol) in MeOH (1 mL) was added MeNH$_2$ (0.11 mL, 0.22 mmol, 2.0 M solution in THF) and the resulting mixture was stirred at rt for 1 h. Next NaCNBH$_3$ (13.6 mg, 0.217 mmol) was added, and the reaction was stirred at rt overnight. The reaction was quenched with HCl (1.0 M, aq.) and purified by prep-HPLC on C18 column eluting with MeCN/H$_2$O (20-70% with 0.1% TFA) to afford the title compound (16.2 mg, 66.8% yield) as its TFA salt. LCMS calc. for C$_{23}$H$_{30}$F$_3$N$_6$O$_3$S$_2$[M+H]$^+$: m/z=559.2; Found: 559.0.

Example 39. 7-(Dimethylamino)-8a-ethyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

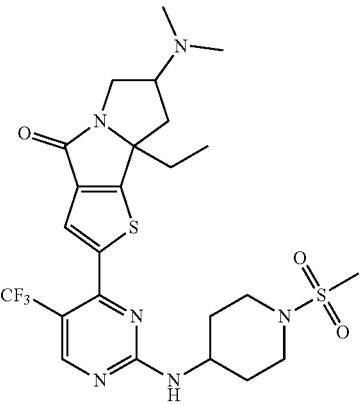 [SMILES: CCC12CC(N(C)C)CN1C(=O)c1cc(-c3nc(NC4CCN(S(C)(=O)=O)CC4)ncc3C(F)(F)F)sc12]

This compound was prepared using procedures analogous to those described for Example 38. LCMS calc. for C$_{24}$H$_{32}$F$_3$N$_6$O$_3$S$_2$ [M+H]$^+$: m/z=573.2; Found: 573.1.

Example 40. 7-Amino-8a-ethyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

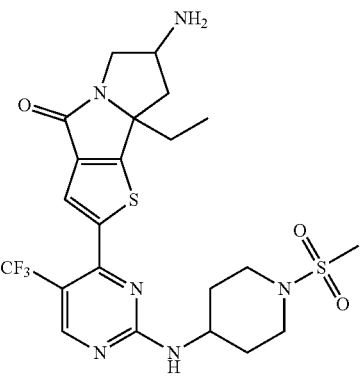 [SMILES: CCC12CC(N)CN1C(=O)c1cc(-c3nc(NC4CCN(S(C)(=O)=O)CC4)ncc3C(F)(F)F)sc12]

Step 1. 8a-Ethyl-7-((4-methoxybenzyl)amino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

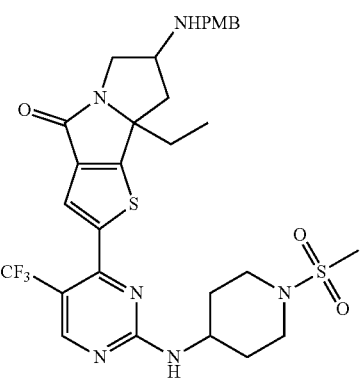

This compound was prepared using procedures analogous to those described for Example 38. LCMS calc. for $C_{30}H_{36}F_3N_6O_4S_2$ [M+H]$^+$: m/z=665.2; Found: 665.1.

Step 2. 7-Amino-8a-ethyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one To a solution of 8a-ethyl-7-((4-methoxybenzyl)amino)-2-(2-((1-(methylsulfonyl) piperidin-4-yl)amino)-5-(trifluoromethyl)pyrimidin-4-yl)-6,7,8,8a-tetrahydro-4H-thieno[2,3-a]pyrrolizin-4-one (18.0 mg, 0.027 mmol) in trifluoroacetic acid (1.0 mL) was added anisole (2.93 mg, 0.027 mmol). The reaction mixture was stirred at 100° C. for 48 h. Then the reaction mixture was concentrated under reduced pressure. The residue was purified by prep-HPLC on C18 column eluting with MeCN/H$_2$O (10-50% with 0.1% TFA) to afford the title compound (3.1 mg, 20% yield) as its TFA salt. LCMS calc. for $C_{22}H_{28}F_3N_6O_3S_2$ [M+H]$^+$: m/z=545.2; Found: 545.2.

Example 41. 8a-Ethyl-7-(ethylamino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

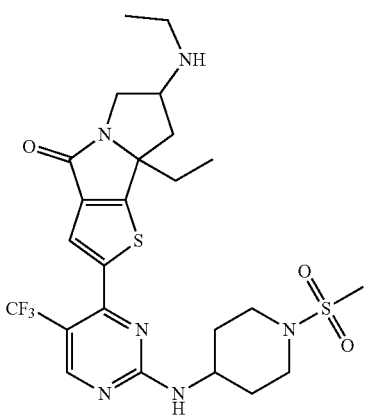

This compound was prepared using procedures analogous to those described for Example 38. LCMS calc. for $C_{24}H_{32}F_3N_6O_3S_2$ [M+H]$^+$: m/z=573.2; Found: 573.3.

Example 42. 8a-Ethyl-7-((methyl-d3)amino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

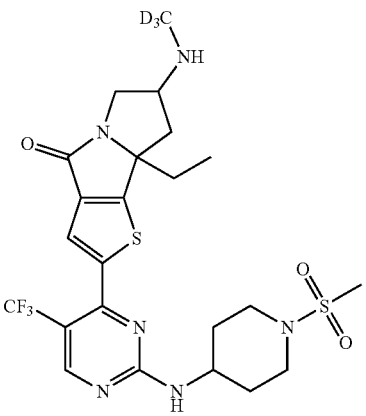 [SMILES: [2H]C([2H])([2H])NC1CN2C(=O)c3cc(-c4nc(NC5CCN(S(C)(=O)=O)CC5)ncc4C(F)(F)F)sc3C2(CC)C1]

This compound was prepared using procedures analogous to those described for Example 38. LCMS calc. for $C_{23}H_{27}D_3F_3N_6O_3S_2$[M+H]$^+$: m/z=562.2; Found: 562.1.

Example 43. 8a-Ethyl-2-(2-(((3R,4S)-3-methyl-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one

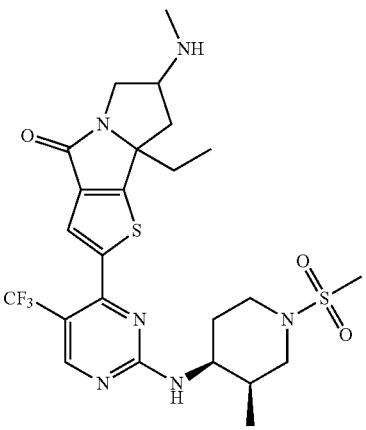 [SMILES: CCC12CC(NC)CN1C(=O)c1cc(-c3nc(N[C@H]4CCN(S(C)(=O)=O)C[C@H]4C)ncc3C(F)(F)F)sc12]

Step 1. Tert-butyl (3R,4S)-4-((4-chloro-5-(trifluoromethyl)pyrimidin-2-yl)amino)-3-methylpiperidine-1-carboxylate

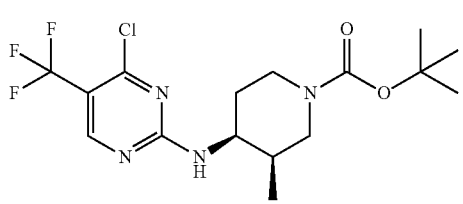 [SMILES: C[C@@H]1CN(C(=O)OC(C)(C)C)CC[C@@H]1Nc1ncc(C(F)(F)F)c(Cl)n1]

This compound was prepared using procedures analogous to those described for Example 35, Step 1. LCMS calc. for $C_{16}H_{23}ClF_3N_4O_2$ [M+H]$^+$: m/z=395.1; Found 395.1.

Step 2. Tert-butyl (3R,4S)-4-((4-(8a-ethyl-4,7-dioxo-6,7,8,8a-tetrahydro-4H-thieno[2,3-a]pyrrolizin-2-yl)-5-(trifluoromethyl)pyrimidin-2-yl)amino)-3-methylpiperidine-1-carboxylate

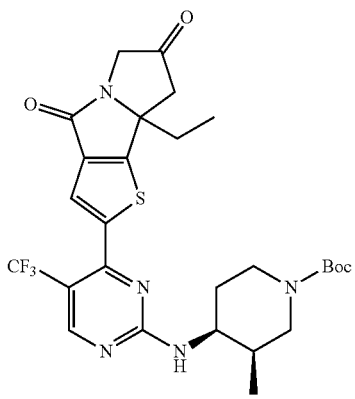 [SMILES: CCC12CC(=O)CN1C(=O)c1cc(-c3nc(N[C@H]4CCN(C(=O)OC(C)(C)C)C[C@H]4C)ncc3C(F)(F)F)sc12]

This compound was prepared using procedures analogous to those described for Example 1, Step 6 and Step 8, using appropriate intermediates from Example 32, Step 1. LCMS calc. for $C_{27}H_{33}F_3N_5O_4S$ [M+H]$^+$: m/z=580.2; Found 580.1.

Step 3. 8a-Ethyl-2-(2-(((3R,4S)-3-methylpiperidin-4-yl)amino)-5-(trifluoromethyl) pyrimidin-4-yl)-8,8a-dihydro-4H-thieno[2,3-a]pyrrolizine-4,7(6H)-dione

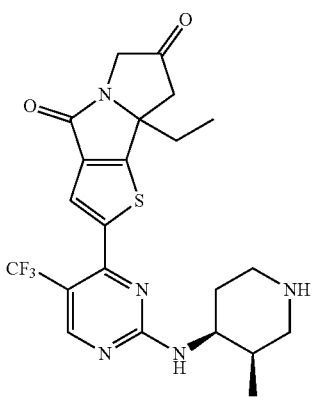 [SMILES: CCC12CC(=O)CN1C(=O)c1cc(-c3nc(N[C@H]4CCNC[C@H]4C)ncc3C(F)(F)F)sc12]

To a solution of tert-butyl (3R,4S)-4-((4-(8a-ethyl-4,7-dioxo-6,7,8,8a-tetrahydro-4H-thieno[2,3-a]pyrrolizin-2-yl)-5-(trifluoromethyl)pyrimidin-2-yl)amino)-3-methylpiperidine-1-carboxylate (74.0 mg, 0.96 mmol) in DCM (2 mL) was added trifluoroacetic acid (2 mL). The reaction mixture was stirred at rt for 2 h and then concentrated under reduced pressure to give the crude title compound (46.0 mg) which was directly used in the next step without further purification. LCMS calc. for $C_{22}H_{25}F_3N_5O_2S$ [M+H]$^+$: m/z=480.2; Found 480.0.

Step 4. 8a-Ethyl-2-(2-(((3R,4S)-3-methyl-1-(methylsulfonyl)piperidin-4-yl)amino)-5-(trifluoromethyl)pyrimidin-4-yl)-8,8a-dihydro-4H-thieno[2,3-a]pyrrolizine-4,7(6H)-dione

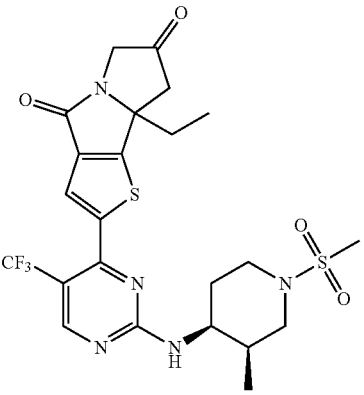 [SMILES: CCC12CC(=O)CN1C(=O)c1cc(-c3nc(N[C@H]4CCN(S(C)(=O)=O)C[C@H]4C)ncc3C(F)(F)F)sc12]

To a solution of 8a-ethyl-2-(2-(((3R,4S)-3-methylpiperidin-4-yl)amino)-5-(trifluoromethyl)pyrimidin-4-yl)-8,8a-dihydro-4H-thieno[2,3-a]pyrrolizine-4,7(6H)-dione (46.0 mg, 0.958 mmol) in DMA (1.0 mL) was added methanesulfonyl chloride (0.00888 mL, 0.12 mmol) at 0° C., followed by the addition of diisopropylethylamine (135 mg, 1.04 mmol). The mixture was then stirred at rt for 3 h. The reaction mixture was diluted with MeCN/H$_2$O and purified by prep-HPLC on C18 column eluting with MeCN/H$_2$O (10-60% with 0.1% TFA) to afford the title compound (35.5 mg, 60.6% yield) as its TFA salt. LCMS calc. for $C_{23}H_{27}F_3N_5O_4S_2$ [M+H]$^+$: m/z=558.2; Found: 558.0.

Step 5. 8a-Ethyl-2-(2-(((3R,4S)-3-methyl-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one This compound was prepared using procedures analogous to those described for Example 38. LCMS calc. for $C_{24}H_{32}F_3N_6O_3S_2$ [M+H]$^+$: m/z=573.2; Found: 573.2.

Example 44. 8a-Ethyl-2-(2-(((3R,4S)-3-methyl-1-((1-methyl-1H-pyrazol-4-yl)sulfonyl) piperidin-4-yl)amino)-5-(trifluoromethyl)pyrimidin-4-yl)-7-(methylamino)-6,7,8,8a-tetrahydro-4H-thieno[2,3-a]pyrrolizin-4-one

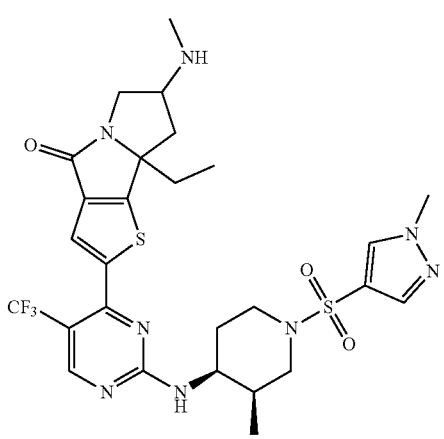 [SMILES: CCC12CC(NC)CN1C(=O)c1cc(-c3nc(N[C@H]4CCN(S(=O)(=O)c5cnn(C)c5)C[C@H]4C)ncc3C(F)(F)F)sc12]

This compound was prepared using procedures analogous to those described for Example 43, Steps 1-5, using 1-methyl-1H-pyrazole-4-sulfonyl chloride to replace methanesulfonyl chloride in Step 4. LCMS calc. for $C_{27}H_{34}F_3N_8O_3S_2$ [M+H]$^+$: m/z=639.2; Found 639.3.

Example 45. 7-Amino-8a-ethyl-2-(2-(((3R,4S)-3-methyl-1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one

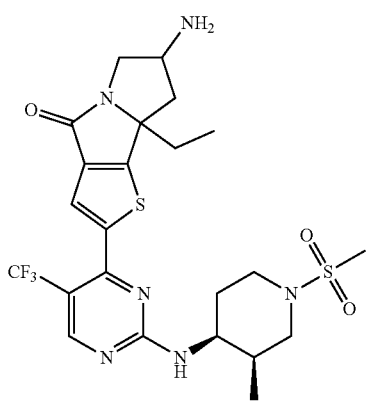 [SMILES: CCC12CC(N)CN1C(=O)c1cc(-c3nc(N[C@H]4CCN(S(C)(=O)=O)C[C@H]4C)ncc3C(F)(F)F)sc12]

This compound was prepared using procedures analogous to those described for Example 43, Steps 1-5, using ammonium hydroxide to replace methylamine in Step 5. LCMS calc. for $C_{23}H_{30}F_3N_6O_3S_2$ [M+H]$^+$: m/z=559.2; Found 559.2.

Example 46. 7-Amino-8a-ethyl-2-(2-(((3R,4S)-3-methyl-1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one

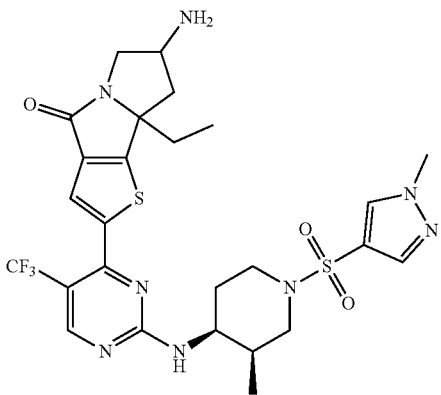 [SMILES: CCC12CC(N)CN1C(=O)c1cc(-c3nc(N[C@H]4CCN(S(=O)(=O)c5cnn(C)c5)C[C@H]4C)ncc3C(F)(F)F)sc12]

This compound was prepared using procedures analogous to those described for Example 43, Steps 1-5, using 1-methyl-1H-pyrazole-4-sulfonyl chloride to replace methanesulfonyl chloride in Step 4 and using ammonium hydroxide to replace methylamine in Step 5. LCMS calc. for $C_{26}H_{32}F_3N_8O_3S_2$[M+H]$^+$: m/z=625.2; Found 625.2.

Example 47. 8a-Ethyl-2-(2-(((3R,4R)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one

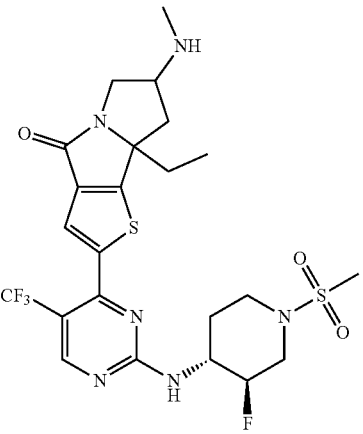 [SMILES: CCC12CC(NC)CN1C(=O)c1cc(-c3nc(N[C@@H]4CCN(S(C)(=O)=O)C[C@H]4F)ncc3C(F)(F)F)sc12]

Step 1. Tert-butyl (3R,4R)-4-((4-chloro-5-(trifluoromethyl)pyrimidin-2-yl)amino)-3-fluoropiperidine-1-carboxylate

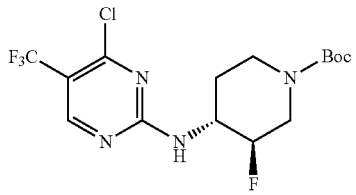 [SMILES: CC(C)(C)OC(=O)N1CC[C@@H](Nc2ncc(C(F)(F)F)c(Cl)n2)[C@H](F)C1]

This compound was prepared using procedures analogous to those described for Example 35, Step 1. $^1$H NMR (300 MHz, CDCl$_3$) δ 8.46 (s, 1H), 5.65-5.60 (m, 1H), 4.50-4.25 (m, 3H), 4.00-3.90 (m, 1H), 3.10-3.00 (m, 2H), 2.25-2.00 (m, 1H), 1.48 (s, 9H).

Step 2. 8a-Ethyl-2-(2-(((3R,4R)-3-fluoro-1-(methylsulfonyl)piperidin-4-yl)amino)-5-(trifluoromethyl) pyrimidin-4-yl)-7-(methylamino)-6,7,8,8a-tetrahydro-4H-thieno[2,3-a]pyrrolizin-4-one This compound was prepared using procedures analogous to those described for Example 43, Steps 2-5. LCMS calc. for $C_{23}H_{29}F_4N_6O_3S_2$ [M+H]$^+$: m/z=577.2; Found 577.2.

Example 48. 8a-Ethyl-2-(2-(((3R,4S)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one

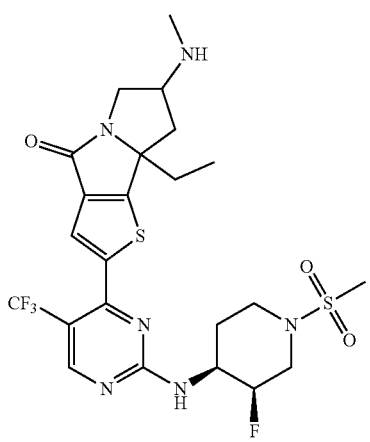 [SMILES: CCC12CC(NC)CN1C(=O)c1cc(-c3nc(N[C@H]4CCN(S(C)(=O)=O)C[C@H]4F)ncc3C(F)(F)F)sc12]

Step 1. Tert-butyl (3R,4S)-4-((4-chloro-5-(trifluoromethyl)pyrimidin-2-yl)amino)-3-fluoropiperidine-1-carboxylate

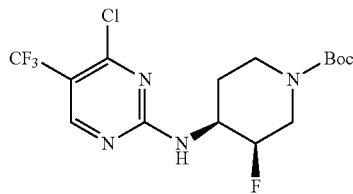 [SMILES: CC(C)(C)OC(=O)N1CC[C@H](Nc2ncc(C(F)(F)F)c(Cl)n2)[C@H](F)C1]

This compound was prepared using procedures analogous to those described for Example 35, Step 1. $^1$H NMR (300 MHz, CDCl$_3$) δ 8.45 (s, 1H), 5.90-5.80 (m, 1H), 4.85-4.70 (m, 1H), 4.50-4.40 (m, 1H), 4.30-4.20 (m, 1H), 3.15-2.80 (m, 2H), 1.90-1.80 (m, 2H), 1.48 (s, 9H).

Step 2. 8a-Ethyl-2-(2-(((3R,4S)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one This compound was prepared using procedures analogous to those described for Example 43, Steps 2-5. LCMS calc. for C$_{23}$H$_{29}$F$_4$N$_6$O$_3$S$_2$ [M+H]$^+$: m/z=577.2; Found 577.2.

Example 49. 8a-Ethyl-2-(2-((1-((1-methyl-1H-pyrazol-4-yl)sulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one

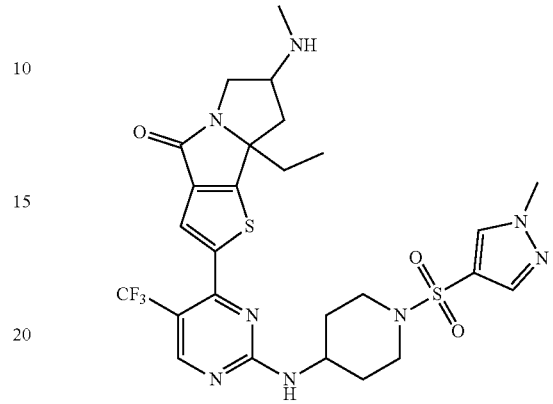

This compound was prepared using procedures analogous to those described for Example 38, using appropriate intermediate from Example 36, Step 1. LCMS calc. for C$_{26}$H$_{32}$F$_3$N$_8$O$_3$S$_2$ [M+H]$^+$: m/z=625.2; Found: 625.3.

Example 50. 7-(Dimethylamino)-8a-ethyl-2-(2-((1-((1-methyl-1H-pyrazol-4-yl)sulfonyl) piperidin-4-yl)amino)-5-(trifluoromethyl)pyrimidin-4-yl)-6,7,8,8a-tetrahydro-4H-thieno[2,3-a]pyrrolizin-4-one

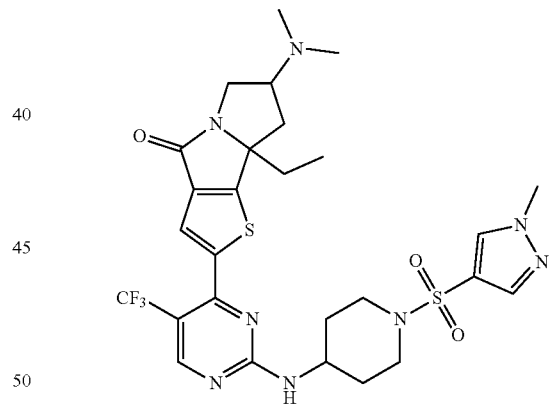

This compound was prepared using procedures analogous to those described for Example 49. LCMS calc. for C$_{27}$H$_{34}$F$_3$N$_8$O$_3$S$_2$ [M+H]$^+$: m/z=639.2; Found: 639.3.

Example A—Enzymatic Activity and Cytotoxicity Studies

CDK2/CyclinE2 Enzymatic Activity Assay

The inhibitory activity of compounds was evaluated in vitro using TR-FRET assay with white 384-well low volume microplate (Greiner Bio-One). CDK2/Cyclin E2 catalyzed phosphorylation of peptide in the presence and absence of compounds was measured and used in IC$_{50}$ determination. Recombinant protein complex CDK2/Cyclin E2, expressed from insect cell, was purchased from ProQinase. Testing compounds were dissolved in DMSO at 1 mM and tested in 9-dose $IC_{50}$ mode. The reaction mixture was prepared by mixing CDK2/CyclinE2 (1 nM final), ULight-4E-BP1 (50 nM final, Perkinelmer, TRF0128-D), and ATP (1 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E) to make a 9.9 µL of reaction mixture. After 20 minutes preincubation at room temperature, 0.1 µL $MgCl_2$ (10 mM final) was added to initiate the reaction. Following a 45 minute incubation at 37° C., the reaction was stopped by addition of 2 µL of quenching buffer consisting of Lance detection buffer (Perkinelmer CR97-100C), LANCE Ultra Europium-anti-P-4E-BP1 (Perkinelmer, TRF0216-D), EDTA, and incubate at room temperature for additional 60 minutes in the dark. The reaction signal was measured by Envision multimode plate reader (PerkinElmer, 2102-0010). $IC_{50}$ values were determined by fitting the data to the standard 4 parameters with Hill Slope using GraphPad Prism software.

CDK4/CyclinD1 Enzymatic Activity Assay

The inhibitory activity of compounds was evaluated in vitro using TR-FRET assay with white 384-well low volume microplate (Greiner Bio-One). CDK4/Cyclin D1 catalyzed phosphorylation of peptide in the presence and absence of compounds was measured and used in $IC_{50}$ determination. Recombinant protein complex CDK4/Cyclin D1, expressed from insect cell, was purchased from ProQinase. Testing compounds were dissolved in DMSO at 1 mM and tested in 9-dose $IC_{50}$ mode. The reaction mixture was prepared by mixing CDK4/CyclinD1 (1 nM final), ULight-4E-BP1 (100 nM final, Perkinelmer, TRF0128-D), and ATP (2 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by the dispenser (TECAN D300E) to make a 9.9 µL of reaction mixture. After 20 minutes preincubation at room temperature, 0.1 µL $MgCl_2$ (10 mM final) was added to initiate the reaction. Following a 45 minute incubation at 37° C., the reaction was stopped by addition of 2 µL of quenching buffer consisting of Lance detection buffer (Perkinelmer CR97-100C), LANCE Ultra Europium-anti-P-4E-BP1 (Perkinelmer, TRF0216-D), EDTA, and incubated at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software.

CDK6/CyclinD1 Enzymatic Activity Assay

The inhibitory activity of compounds was evaluated in vitro using TR-FRET assay with white 384-well low volume microplate (Greiner Bio-One). CDK6/CyclinD1 catalyzed phosphorylation of peptide in the presence and absence of compounds was measured and used in $IC_{50}$ determination. Recombinant protein complex CDK6/CyclinD1 expressed from insect cell, was purchased from ProQinase. Testing compounds were dissolved in DMSO at 1 mM and tested in a 9-dose $IC_{50}$ mode. The reaction mixture was prepared by mixing CDK6/CyclinD1 (1 nM final), ULight-4E-BP1 (100 nM final, Perkinelmer, TRF0128-D), and ATP (1 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E) to make a 9.9 µL of reaction mixture. After 20 minutes preincubation at room temperature, 0.1 µL $MgCl_2$ (10 mM final) was added to initiate the reaction. Following a 40 minute incubation at 37° C., the reaction was stopped by addition of 2 µL of quenching buffer consisting of Lance detection buffer (Perkinelmer CR97-100C), LANCE Ultra Europium-anti-P-4E-BP1 (Perkinelmer, TRF0216-D), EDTA, and incubate at room temperature for additional 60 minutes in the dark. The reaction signal was measured by Envision multimode plate reader (PerkinElmer, 2102-0010). $IC_{50}$ values were determined by fitting the data to the standard 4 parameters with Hill Slope using GraphPad Prism software.

Cell Proliferation Studies in OVCAR3 Cells

Cell proliferation studies were conducted in OVCAR3 adenocarcinoma cell line. Cells were maintained in RPMI (Corning, Catalog #: 10-040-CV) supplemented with 10% v/v FBS (Gibco, Catalog #: 26140-079), 1% v/v Penicillin Streptomycin (Gibco, Catalog #15140-122) Cells were seeded in 384-well plates at a density of 250 cells/well. Compounds dissolved in DMSO were plated in quadruplicate using a digital dispenser (D300E, Tecan) and tested with a 9-point 3-fold serial dilution. Cells were incubated for 10 days in a 37° C. active humidified incubator at 5% $CO_2$. A media exchange and second compound addition were performed on day 5. Cell viability was measured using the ATP-Lite 1-Step Luminescence reagent (Perkin Elmer, Catalog #: 6016731) as per manufacturer's instructions. Luminescence signal was measured with a multimode plate reader (Envision 2105, Perkin Elmer). Raw data files were imported to Dotmatics Screening Ultra for $IC_{50}$ analysis. Luminescence values were normalized to both background and DMSO controls to obtain a percentage of viable cells relative to DMSO vehicle control.

pRB ICW Assay in OVCAR3 Cells

OVCAR3 cells were maintained in RPMI (Corning, Catalog #: 10-040-CV) supplemented with 10% v/v FBS (Gibco, Catalog #: 26140-079), 1% v/v Penicillin Streptomycin (Gibco, Catalog #15140-122.) OVCAR3 cells grown at log phase were trypsinized, counted, and resuspended in fresh medium to reach a final density of 6.7e4 cells/mL and 75 µL of culture were dispensed into a 384-well plate (Falcon, cat #353962) using a Multidrop Combi dispenser (Thermo Scientific). The next day, compounds were dispensed as a 9-point, ½ log serial dilution using a Tecan digital dispenser (D300e), and cells were incubated with compound for 2 hours in a humidified incubator at 37° C. A reference compound at a final concentration of 10 µM was used as a control for maximum inhibition. Each compound was tested in duplicates for each experiment. At the end of the incubation, 25 µL of 16% paraformaldehyde (Electron Microscopy, cat #15710) was slowly added to each well and the plate was incubated at room temperature (RT) for 30 minutes to fix cells. Cells were then permeabilized by incubating with 50 µL/well of wash buffer (lx PBS with 0.1% Triton X-100) 5×5 minutes, followed by 1 hour blocking with 30 µL/well of Odyssey blocking buffer (Li—COR, cat #927-40000), at RT. Anti-phosphor RB antibody (Cell signaling 8516S) was diluted 1:1000 in Odyssey blocking buffer and 20 µL was added to all wells and incubated overnight in 4° C. with gently rocking. The next day, cells were washed 5×5 min with 50 µL/well of wash buffer, followed with 1 hour incubation with secondary antibody and DRAQ5 diluted in Odyssey blocking buffer (1:500 dilution for secondary antibody and 1:2000 dilution for DRAQ5), 5×5 min washes, and one last wash with water. Plates were dried in 37° C. oven for 5 minutes and scanned using Li—COR Odyssey CLx imaging system to acquire intensities at 700 and 800 nm channels.

The IC$_{50}$ values are summarized below in Table 1.

TABLE 1

| | IC$_{50}$ Values | | |
|---|---|---|---|
| Example | CDK2_E1 IC$_{50}$ (nM) | CDK4_D1 IC$_{50}$ (nM) | OVCAR3 p-RB ICW IC$_{50}$ (nM) |
| 1 | +++ | +++ | ++ |
| 2 or 3 | +++ | +++ | — |
| 3 or 2 | +++ | +++ | ++ |
| 4 | +++ | +++ | — |
| 5 | +++ | +++ | — |
| 6 | +++ | +++ | +++ |
| 7 or 8 | +++ | +++ | +++ |
| 8 or 7 | +++ | +++ | ++ |
| 9 | +++ | — | — |
| 10 | +++ | +++ | ++ |
| 11 | +++ | +++ | ++ |
| 12 or 13 | +++ | +++ | ++ |
| 13 or 12 | +++ | +++ | — |
| 14 | +++ | +++ | +++ |
| 15 | +++ | +++ | +++ |
| 16 | +++ | +++ | +++ |
| 17 | +++ | +++ | ++ |
| 18 | +++ | +++ | ++ |
| 19 | +++ | +++ | +++ |
| 20 | +++ | +++ | +++ |
| 21 | +++ | +++ | ++ |
| 22 | +++ | +++ | +++ |
| 23 | +++ | +++ | ++ |
| 24 | +++ | +++ | ++ |
| 25 | +++ | +++ | +++ |
| 26 | +++ | +++ | ++ |
| 27 | +++ | +++ | +++ |
| 28 | ++ | ++ | — |
| 29 | +++ | +++ | +++ |
| 30 | +++ | +++ | ++ |
| 31 | +++ | +++ | +++ |
| 32 | +++ | +++ | +++ |
| 33 | +++ | +++ | +++ |
| 34 | +++ | +++ | +++ |
| 35 | +++ | +++ | +++ |
| 36 | +++ | +++ | +++ |
| 37 | +++ | +++ | +++ |
| 38 | +++ | +++ | +++ |
| 39 | +++ | +++ | +++ |
| 40 | +++ | +++ | +++ |
| 41 | +++ | +++ | +++ |
| 42 | +++ | +++ | +++ |
| 43 | +++ | +++ | ++ |
| 44 | +++ | +++ | +++ |
| 45 | +++ | +++ | +++ |
| 46 | +++ | +++ | +++ |
| 47 | +++ | +++ | +++ |
| 48 | +++ | +++ | +++ |
| 49 | +++ | +++ | +++ |
| 50 | +++ | +++ | +++ |

In Table 1, a "+" denotes an IC$_{50}$ value of >500 nM;

a "++" denotes an IC$_{50}$ value of 100 nM < IC$_{50}$ ≤ 500 nM;

a "+++" denotes an IC$_{50}$ value of IC$_{50}$ ≤ 100 nM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed:

1. A compound of Formula I:

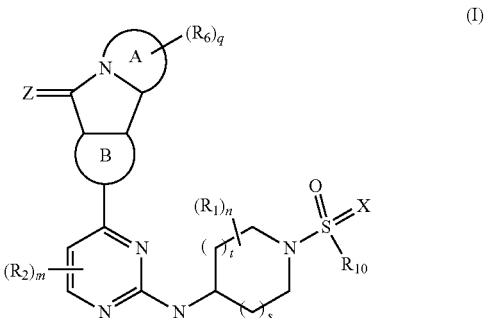

or a pharmaceutically acceptable salt or solvate or N-oxide thereof, wherein
ring A is a 4-9-membered cycloalkyl or heterocycloalkyl ring;
ring B is a 5-membered heteroaryl selected from:

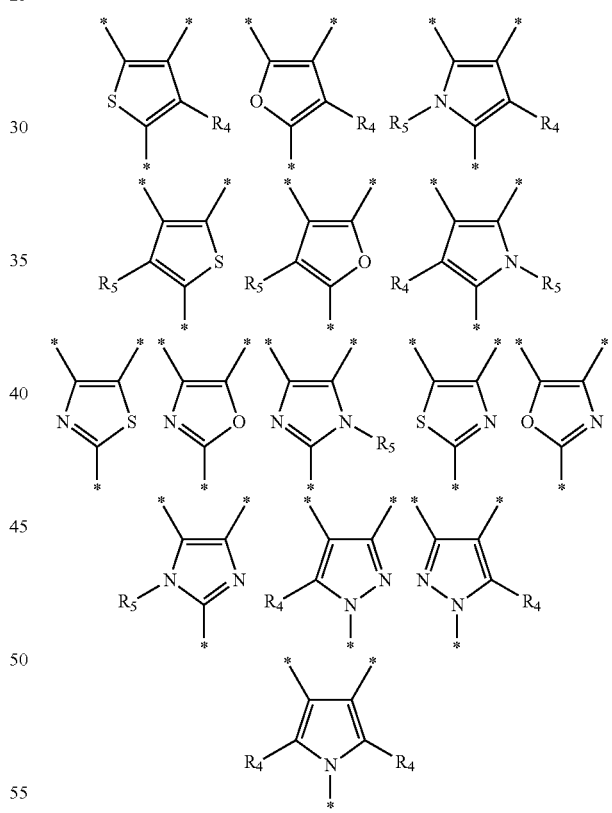

Z is O, S, NR$^b$, NOR$^b$ or N—CN,
m is 0, 1 or 2;
n is 0, 1, 2, 3, 4, 5, 6, 7, 8 or 9;
s is 0, 1, 2 or 3;
t is 0, 1, 2 or 3;
q is 0, 1, 2, 3, 4, 5, 6, 7, 8 or 9;
each R$_1$, when present, is independently H, D, halogen, —OH, —CN, —NO$_2$, oxo, —C$_1$-C$_6$alkyl, C$_{1-6}$alkoxide, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^c$)(OR$^d$) or —S(O)$_2$R$^b$;

or two R$^1$ together with the carbon atom(s) to which they are both attached at same carbon or different carbons, form a carbocyclic or heterocyclic group;

each R$_2$ is independently H, D, halogen, C$_1$-C$_8$ alkoxide, C$_1$-C$_8$ alkyl, haloalkoxide, SF$_5$, or CN, wherein the C$_{1-8}$alkyl may be optionally substituted with D, halogen, —OH, —CN, or cycloalkyl;

each R$_4$ is independently H, D, halogen, CN, —C$_2$-C$_6$alkenyl, —C$_2$-C$_6$alkynyl, C$_1$-C$_8$ alkoxide, C$_1$-C$_8$ alkyl, haloalkyl, C$_1$-C$_8$ hydroxylalkyl, or C$_3$-C$_8$ cycloalkyl or C$_3$-C$_8$ heteroycloalkyl;

each R$^a$ is independently H, D, —C(O)R$^b$, —C(O)OR$^c$, —C(O)NR$^c$R$^d$, —C(=NR)NR$^b$R$^c$, —C(=NOR$^b$)NR$^b$R$^c$, —C(=NCN)NR$^b$R$^c$, —P(OR$^c$)$_2$, —P(O)OR$^c$R$^b$, —S(O)$_2$R$^b$, —S(O)$_2$NR$^c$R$^d$, SiR$_3$, —C$_1$-C$_{10}$alkyl, —C$_2$-C$_{10}$ alkenyl, —C$_2$-C$_{10}$ alkynyl, C$_0$-C$_1$alk-aryl, cycloalkyl, cycloalkenyl, C$_0$-C$_1$alk-heteroaryl, heterocycloalkyl, or heterocycloalkenyl;

each R$^b$, is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl;

each R$^c$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, C$_1$alk-aryl, heteroaryl, cycloalkyl, cycloalkenyl, C$_1$alk-heteroaryl, heterocycloalkyl, or heterocycloalkenyl;

each R$^d$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, C$_1$alk-aryl, heteroaryl, cycloalkyl, cycloalkenyl, C$_1$alk-heteroaryl, heterocycloalkyl, or heterocycloalkenyl;

or R$^c$ and R$^d$, together with the atoms to which they are both attached, form a monocyclic or multicyclic heterocycloalkyl, or a monocyclic or multicyclic heterocyclo-alkenyl group;

R$_5$ is H, OR$^b$, C$_{1-4}$alkyl, wherein the C$_{1-4}$alkyl may be optionally substituted with at least one of D, halogen, —OH, —CN or an amine, cycloalkyl, heterocycloalkyl; and each R$_6$, when present, is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^a$R$^d$, —NR$^a$R$^c$, —C(O)R$^b$, —OC(O)R$^b$, —C(O)OR, —C(O)NR$^c$R$^d$, —S(O)R$^b$, —S(O)$_2$NR$^c$R$^d$, —S(O)(=NR)R$^b$, —SF$_5$, —P(O)R$^a$R$^b$, —P(O)(OR$^b$)(OR$^b$), —B(OR$^c$)(OR$^d$) or —S(O)$_2$R$^b$; wherein said that —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl is optionally substituted by 1-6 R groups selected from H, D, halogen, —OH, —CN, —OR$^a$, —SR$^a$, —NR$^c$R$^d$, —NR$^a$R$^c$, —C(O)R$^b$, —OC(O)R$^b$, —C(O)OR, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^c$)(OR$^d$) or —S(O)$_2$R$^b$;

or two R$_6$ groups together with the atom(s) to which they attached (same atom or different atoms) can form a spirocyclic group, multicyclic heterocycloalkyl, or a multicyclic cycloalkyl group;

X is O or NR$^5$; and

R$_{10}$ is H, D, —NR$^c$R$^d$, —NR$^a$R$^c$, C$_{1-6}$alkyl, C$_{3-7}$cycloalkyl, C$_{4-7}$heterocycloalkyl, C$_{3-7}$cycloalkylalkyl, C$_{4-7}$heterocycloalkylalkyl, aryl, heteroaryl, arylalkyl, heteroarylalkyl, or haloalkyl; wherein said that C$_{1-6}$alkyl, C$_{3-7}$cycloalkyl, C$_{4-7}$heterocycloalkyl, C$_{3-7}$cycloalkylalkyl, C$_{4-7}$heterocycloalkylalkyl, aryl, heteroaryl, arylalkyl and heteroarylalkyl is optionally substituted by 1-6 R selected from H, D, halogen, —OH, —CN, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$.

2. The compound of claim 1, that is a compound of formula II:

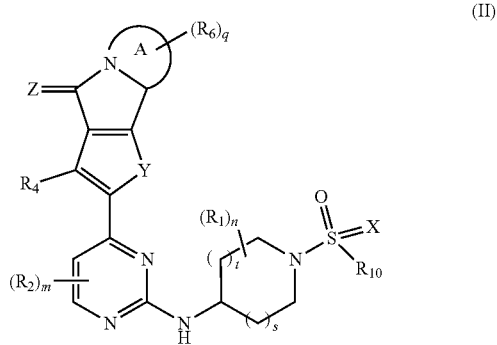

or a pharmaceutically acceptable salt or solvate or N-oxide thereof; wherein Y=S, O, NR$^5$.

3. The compound of claim 1, wherein q is 0, 1, 2, 3, 4, 5, 6, 7 or 8.

4. The compound of claim 1, wherein Z is O.

5. The compound of claim 1, wherein R$_4$ is H, D, Me, halogen or haloalkyl.

6. The compound of claim 1, wherein R$_5$ is H, D or Me.

7. The compound of claim 1, wherein n is 0, 1 or 2.

8. The compound of claim 1, wherein m is 0, 1 or 2.

9. The compound of claim 1, that is a compound of formula III:

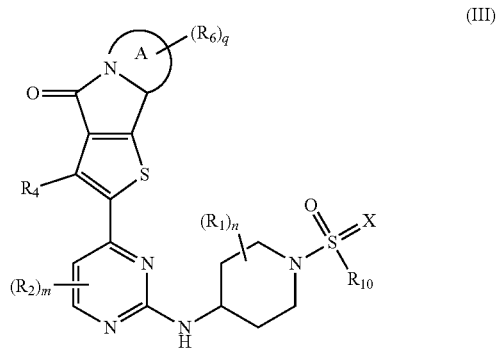

or a pharmaceutically acceptable salt or solvate or N-oxide thereof.

10. The compound of claim 1, that is a compound of formula IV:

(IV)

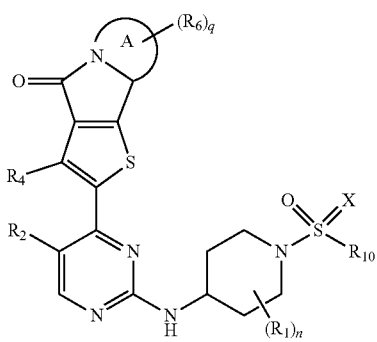

or a pharmaceutically acceptable salt or solvate or N-oxide thereof.

11. The compound of claim 1, that is a compound of formula V, formula VI, formula VII, or formula VIII:

(V)

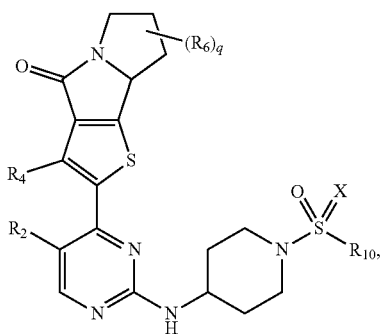

(VI)

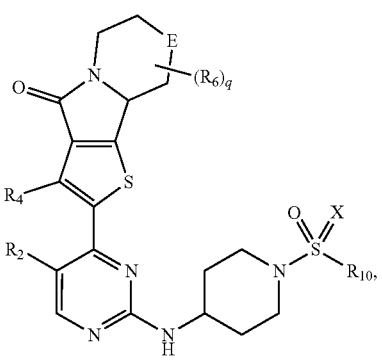

(VII)

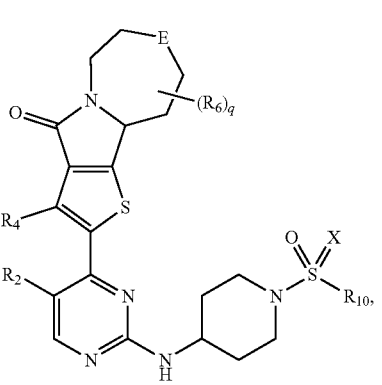

(VIII)

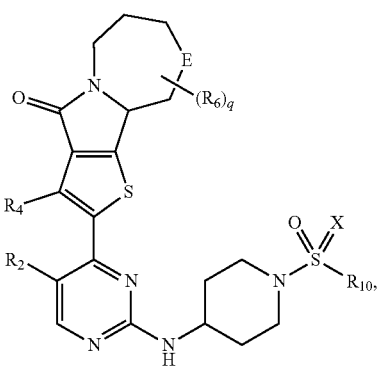

or a pharmaceutically acceptable salt thereof; wherein E is bond, $C(R^a)_2$, $NR^a$, —O—, —S—, SO, $SO_2$, $SO_2NR^a$, —C(=O)$NR^a$—, $NR^aC$(=O)$NR^a$, or $NR^aS(O)_2NR^a$.

12. The compound of claim 1, that is a compound of formula IX, formula X, formula XI, formula XII, formula XIII, formula XIV, formula XV, formula XVI, formula XVII or formula XVIII:

(IX)

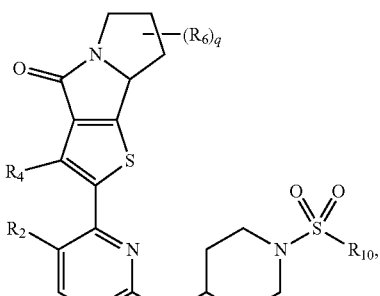

(X)

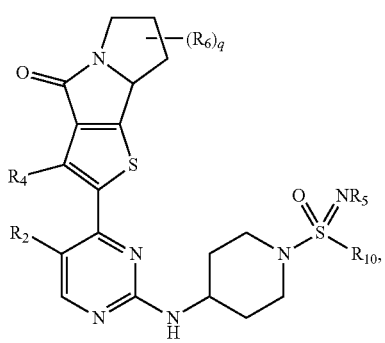

(XI)

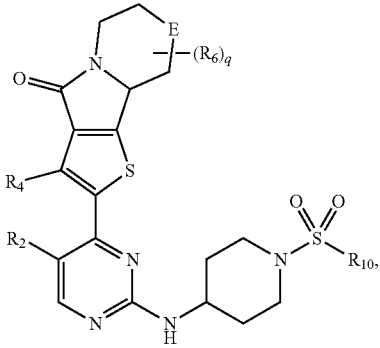

(XII)

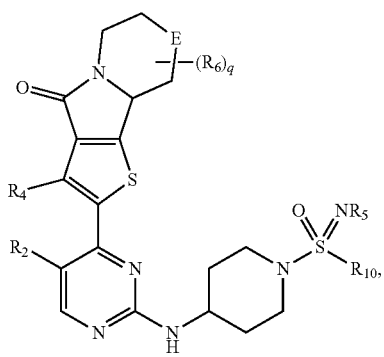

(XIII)

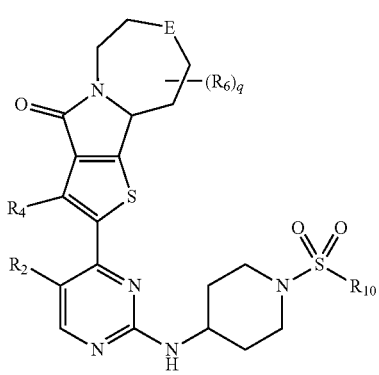

(XIV)

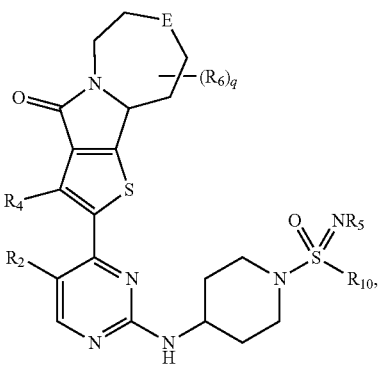

(XV)

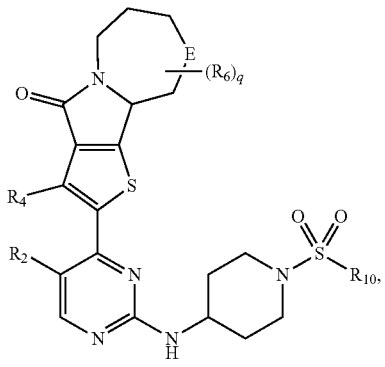

(XVI)

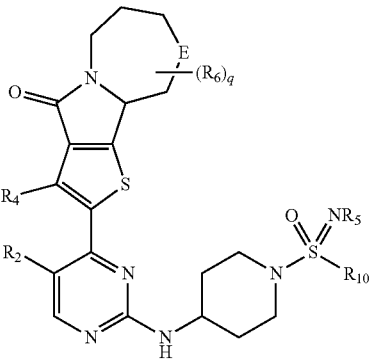

or a pharmaceutically acceptable salt or solvate or N-oxide thereof; wherein

E is bond, $C(R^a)_2$, $NR^a$, —O—, —S—, SO, $SO_2$, $SO_2NR^a$, —C(=O)$NR^a$—, $NR^aC(=O)NR^a$, or $NR^aS(O)_2NR^a$;

$R_4$ is H, D, Me, or haloalkyl; and each q is independently 0, 1, 2 or 3.

13. The compound of claim 1, that is a compound of formula XVII, formula XVIII, formula XIX, formula XX, formula XXI, or formula XXII:

(XVII)

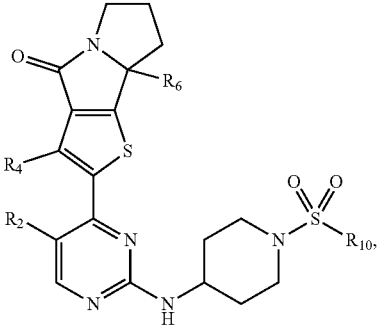

(XVIII)

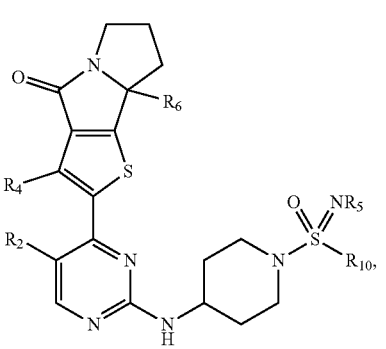

(XIX)

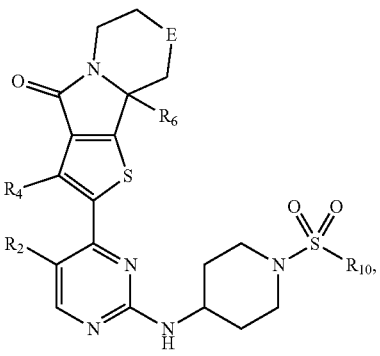

-continued

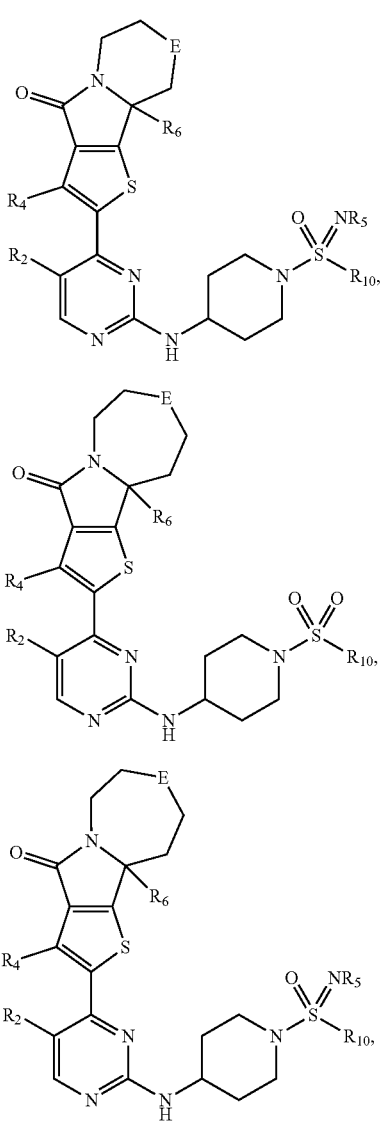

(XX)

(XXI)

(XXII)

or a pharmaceutically acceptable salt or solvate or N-oxide thereof; wherein

E is bond, $C(R^a)_2$, $NR^a$, —O—, —S—, SO, $SO_2$, $SO_2NR^a$, —C(=O)$NR^a$—, $N^aC$(=O)$NR^a$, or $NR^aS(O)_2NR^a$;

$R_4$ is H, D, Me, or haloalkyl; and $R_6$ is H, D, optional substituted $C_{1-6}$ alkyl, optional substituted $C_{3-6}$ cycloalkyl, or optional substituted $C_{3-6}$ heterocycloalkyl.

14. The compound of claim 1 that is:
9a-isopropyl-2-(2-((1-(methylsulfonyl)piperidin-4-yl)amino)-5-(trifluoromethyl) pyrimidin-4-yl)-7,8,9,9a-tetrahydrothieno[2,3-a]indolizin-4(6H)-one;
(9aS)-9a-isopropyl-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;
(9aR) 9a-Isopropyl-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;
9a-(3-hydroxypropyl)-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;
9a-(2-hydroxyethyl)-2-(2-((1-(methylsulfonyl)piperidin-4-yl)amino)-5-(trifluoro-methyl) pyrimidin-4-yl)-7,8,9,9a-tetrahydrothieno[2,3-a]indolizin-4(6H)-one;
2-(5-fluoro-2-((1-(methylsulfonyl)piperidin-4-yl)amino) pyrimidin-4-yl)-9a-methyl-7,8,9,9a-tetrahydrothieno[2,3-a]indolizin-4(6H)-one;
(9aS)-2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one;
(9aR)-2-(5-Fluoro-2-((1-(methylsulfonyl)piperidin-4-yl)amino)pyrimidin-4-yl)-9a-methyl-7,8,9,9a-tetrahydrothieno[2,3-a]indolizin-4(6H)-one;
2-(5-Fluoro-2-((1-(methylsulfonyl)piperidin-4-yl)amino) pyrimidin-4-yl)-9a-isopropyl-7,8,9,9a-tetrahydrothieno[2,3-a]indolizin-4(6H)-one;
10a-Isopropyl-2-(2-((1-(methylsulfonyl)piperidin-4-yl)amino)-5-(trifluoromethyl) pyrimidin-4-yl)-6,7,10,10a-tetrahydrothieno[2',3':3,4]pyrrolo[1,2-d][1,4]oxazepin-4(9H)-one;
8a-Isopropyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
(8aS)-8a-Isopropyl-2-(2-((1-(methylsulfonyl)piperidin-4-yl)amino)-5-(trifluoro-methyl) pyrimidin-4-yl)-6,7,8,8a-tetrahydro-4H-thieno[2,3-a]pyrrolizin-4-one;
(8aR)-8a-Isopropyl-2-(2-((1-(methylsulfonyl)piperidin-4-yl)amino)-5-(trifluoro-methyl) pyrimidin-4-yl)-6,7,8,8a-tetrahydro-4H-thieno[2,3-a]pyrrolizin-4-one;
8a-Ethyl-2-[2-[(1-methylsulfonylpiperidin-4-yl)amino]-5-(trifluoromethyl) pyrimidin-4-yl]-7,8-dihydro-6H-thieno[2,3-a]pyrrolizin-4-one;
8a-Ethyl-2-[5-fluoro-2-[(1-methylsulfonylpiperidin-4-yl)amino]pyrimidin-4-yl]-7,8-dihydro-6H-thieno[2,3-a]pyrrolizin-4-one;
8a-Ethyl-2-[5-methyl-2-[(1-methylsulfonylpiperidin-4-yl)amino]pyrimidin-4-yl]-7,8-dihydro-6H-thieno[2,3-a]pyrrolizin-4-one;
or a pharmaceutically acceptable salt thereof.

15. The compound of claim 1 that is:
8a-(Hydroxymethyl)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
8a-(Fluoromethyl)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
8a-(2-Fluoroethyl)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
8a-Methyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;
2-(2-((1-(Methylsulfonyl)piperidin-4-yl)amino)-5-(trifluoromethyl)pyrimidin-4-yl)-6,7,8,8a-tetrahydro-4H-thieno[2,3-a]pyrrolizin-4-one;
8a-Cyclopropyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
8a-Cyclobutyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;
8a-(3,3-Difluorocyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;
8a-(3-Hydroxycyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-(3-Fluorocyclobutyl)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

2-(5-Chloro-2-((1-(methylsulfonyl)piperidin-4-yl)amino)pyrimidin-4-yl)-8a-ethyl-6,7,8,8a-tetrahydro-4H-thieno[2,3-a]pyrrolizin-4-one;

8a-Ethyl-2-(2-((1-(methylsulfonyl)piperidin-4-yl)amino)pyrimidin-4-yl)-6,7,8,8a-tetrahydro-4H-thieno[2,3-a]pyrrolizin-4-one;

7-Hydroxy-8a-isopropyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Isopropyl-7-methoxy-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

7-(Hydroxymethyl)-8a-isopropyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7,7-difluoro-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-hydroxy-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-hydroxy-7-methyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7,7-difluoro-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7-hydroxy-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-7-(methylamino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-(Dimethylamino)-8a-ethyl-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-Amino-8a-ethyl-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-(ethylamino)-2-(2-((1-(methylsulfonyl)piperidin-4-yl)amino)-5-(trifluoromethyl) pyrimidin-4-yl)-6,7,8,8a-tetrahydro-4H-thieno[2,3-a]pyrrolizin-4-one;

8a-Ethyl-7-((methyl-d3)amino)-2-(2-((1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-(((3R,4S)-3-methyl-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-(((3R,4S)-3-methyl-1-((1-methyl-1H-pyrazol-4-yl)sulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

7-Amino-8a-ethyl-2-(2-(((3R,4S)-3-methyl-1-(methylsulfonyl)piperidin-4-yl)amino)-5-(trifluoromethyl)pyrimidin-4-yl)-6,7,8,8a-tetrahydro-4H-thieno[2,3-a]pyrrolizin-4-one;

7-Amino-8a-ethyl-2-(2-(((3R,4S)-3-methyl-1-((1-methyl-1H-pyrazol-4-yl)sulfonyl) piperidin-4-yl)amino)-5-(trifluoromethyl)pyrimidin-4-yl)-6,7,8,8a-tetrahydro-4H-thieno[2,3-a]pyrrolizin-4-one;

8a-Ethyl-2-(2-(((3R,4R)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-(((3R,4S)-3-fluoro-1-(methylsulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

8a-Ethyl-2-(2-((1-((1-methyl-1H-pyrazol-4-yl)sulfonyl)piperidin-4-yl)amino)-5-(trifluoromethyl)pyrimidin-4-yl)-7-(methylamino)-6,7,8,8a-tetrahydro-4H-thieno[2,3-a]pyrrolizin-4-one;

7-(Dimethylamino)-8a-ethyl-2-(2-((1-((1-methyl-1H-pyrazol-4-yl)sulfonyl)piperidin-4-yl)amino)-5-(trifluoromethyl)pyrimidin-4-yl)-6,7,8,8a-tetrahydro-4H-thieno[2,3-a]pyrrolizin-4-one;

or a pharmaceutically acceptable salt thereof.

16. A pharmaceutical composition comprising a compound according to claim 1, or a pharmaceutically acceptable salt thereof, and a pharmaceutically acceptable excipient.

17. A method for treating a disorder mediated by CDK2 and CDK4 and CDK6 in a patient in need thereof, comprising administering to said patient a compound according to claim 1, or a pharmaceutically acceptable salt thereof, or a pharmaceutical composition comprising the compound.

18. The method according to claim 17, wherein the disorder is a cancer.

19. The method according to claim 18, wherein the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

20. The method according to claim 19, wherein the breast cancer is HR+/HER2– or HR+/HER2+ advanced or metastatic breast cancer; and the malignant brain tumors are glioblastoma, astrocytoma, or pontine glioma.

21. The method according to claim 17, wherein the patient is administered the pharmaceutical composition.

22. The method according to claim 17, wherein the administration is oral administration.

23. The method according to claim 17, further comprising administering an additional therapeutic agent to the patient that is a PRMT5 inhibitor, a HER2 kinase inhibitor, an aromatase inhibitor, an estrogen receptor antagonist or an alkylating agent.

24. The method according to claim 23, wherein the aromatase inhibitor is letrozole; wherein the estrogen receptor antagonist is fulvestrant; or wherein the alkylating agent is temozolomide.

* * * * *